US011357979B2

(12) United States Patent
Evans et al.

(10) Patent No.: US 11,357,979 B2
(45) Date of Patent: Jun. 14, 2022

(54) SYSTEMS AND METHODS FOR SENSING AND STIMULATION

(71) Applicant: Lungpacer Medical Inc., Vancouver (CA)

(72) Inventors: Douglas G. Evans, Downingtown, PA (US); Viral S. Thakkar, Chester Springs, PA (US)

(73) Assignee: Lungpacer Medical Inc., Vancouver (CA)

( * ) Notice: Subject to any disclaimer, the term of this patent is extended or adjusted under 35 U.S.C. 154(b) by 118 days.

(21) Appl. No.: 16/874,839

(22) Filed: May 15, 2020

(65) Prior Publication Data

US 2020/0360690 A1 Nov. 19, 2020

Related U.S. Application Data

(60) Provisional application No. 62/848,739, filed on May 16, 2019.

(51) Int. Cl.
*A61N 1/36* (2006.01)
*A61B 5/091* (2006.01)
(Continued)

(52) U.S. Cl.
CPC .......... *A61N 1/3601* (2013.01); *A61N 1/3611* (2013.01); *A61N 1/3614* (2017.08);
(Continued)

(58) Field of Classification Search
CPC ... A61N 1/3601; A61N 1/3611; A61N 1/3614
See application file for complete search history.

(56) References Cited

U.S. PATENT DOCUMENTS 1,693,734 A 12/1928 Waggoner
2,532,788 A 12/1950 Sarnoff
(Continued)

FOREIGN PATENT DOCUMENTS

CN 1652839 A 8/2005
CN 102143781 A 8/2011
(Continued)

OTHER PUBLICATIONS

International Search Report in International Application No. PCT/US2020/033057, dated Aug. 20, 2020 (2 pages).
(Continued)

*Primary Examiner* — Amanda K Hulbert
*Assistant Examiner* — Philip C Edwards
(74) *Attorney, Agent, or Firm* — Bookoff McAndrews, PLLC

(57) ABSTRACT

A system for stimulating body tissue may include a stimulation lead, sensors, and a control unit. The stimulation lead may include one or more energy sources. The control unit may include a processor and non-transitory computer readable medium, and an interface (e.g., touch screen interface) for receiving user inputs and communicating information to the user. The sensors may be configured to provide impedance measurements to the control unit. The control unit may calculate lung gas distributions and/or generate an image modeling lung gas distributions. Stimulation delivered by the stimulation may be adjusted based on the impedance measurements.

20 Claims, 26 Drawing Sheets

(51) Int. Cl.
*A61M 16/00* (2006.01)
*A61B 5/08* (2006.01)

(52) U.S. Cl.
CPC ..... *A61N 1/36171* (2013.01); *A61N 1/36175* (2013.01); *A61B 5/082* (2013.01); *A61B 5/0809* (2013.01); *A61B 5/091* (2013.01); *A61M 16/0057* (2013.01); *A61M 2205/054* (2013.01)

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | Barchilon |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,143,872 A | 3/1979 | Havstad et al. |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | McCormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | DiMarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,165,133 A | 12/2000 | Rapoport |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,249,708 B1 | 6/2001 | Nelson et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |

(56) References Cited

U.S. PATENT DOCUMENTS

| | | |
|---|---|---|
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,080,645 B2 | 7/2006 | Genger et al. |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,167,751 B1 | 1/2007 | Whitehurst et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van Venroo et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |

(56) References Cited

U.S. PATENT DOCUMENTS

| | | |
|---|---|---|
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,511,303 B2 | 8/2013 | Djupesland |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,144,680 B2 | 9/2015 | Kaula et al. |
| 9,149,642 B2 | 10/2015 | McCabe et al. |
| 9,168,377 B2 | 10/2015 | Hoffer |
| 9,174,046 B2 | 11/2015 | Francois et al. |
| 9,199,075 B1 | 12/2015 | Westlund |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,468,755 B2 | 10/2016 | Westlund |
| 9,474,894 B2 | 10/2016 | Mercanzini et al. |
| 9,485,873 B2 | 11/2016 | Shah et al. |
| 9,498,625 B2 | 11/2016 | Bauer |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,239 B2 | 4/2017 | Francois et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,349 B2 | 8/2017 | Westlund et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,132 B2 | 5/2018 | Francois et al. |
| 9,956,396 B2 | 5/2018 | Young et al. |
| 9,968,785 B2 | 5/2018 | Hoffer et al. |
| 9,968,786 B2 | 5/2018 | Bauer |
| 9,987,488 B1 | 6/2018 | Gelfand et al. |
| 9,999,768 B2 | 6/2018 | Gelfand et al. |
| 10,022,546 B2 | 7/2018 | Hoffer et al. |
| 10,035,017 B2 | 7/2018 | Thakkar et al. |
| 10,039,920 B1 | 8/2018 | Thakkar et al. |
| 10,195,429 B1 | 2/2019 | Thakkar et al. |
| 10,293,164 B2 | 5/2019 | Nash et al. |
| 10,300,270 B2 | 5/2019 | Gelfand et al. |
| 10,315,035 B2 | 6/2019 | Bauer |
| 10,335,592 B2 | 7/2019 | Bauer et al. |
| 10,369,361 B2 | 8/2019 | Bauer et al. |
| 10,391,314 B2 | 8/2019 | Hoffer et al. |
| 10,406,366 B2 | 9/2019 | Westlund et al. |
| 10,406,367 B2 | 9/2019 | Meyyappan |
| 10,413,203 B2 | 9/2019 | Saha et al. |
| 10,448,995 B2 | 10/2019 | Olson |
| 10,493,271 B2 | 12/2019 | Bauer |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0125786 A1 | 7/2003 | Gliner et al. |
| 2003/0195571 A1 | 10/2003 | Burnes et al. |

(56) References Cited

U.S. PATENT DOCUMENTS

| | | |
|---|---|---|
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288729 A1* | 12/2005 | Libbus ................ A61N 1/3601 607/42 |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0024222 A1 | 10/2006 | Bradley et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2009/0318993 A1 | 12/2009 | Eidenschink et al. |
| 2010/0022950 A1 | 1/2010 | Anderson et al. |
| 2010/0036451 A1 | 2/2010 | Hoffer |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0034977 A1 | 2/2011 | Janik et al. |
| 2011/0060381 A1 | 3/2011 | Ignagni et al. |
| 2011/0077726 A1 | 3/2011 | Westlund et al. |
| 2011/0093032 A1 | 4/2011 | Boggs, II et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1* | 1/2013 | Karamanoglu .... A61N 1/36139 607/42 |

(56) References Cited

U.S. PATENT DOCUMENTS

| | | |
|---|---|---|
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0202448 A1 | 7/2015 | Hoffer et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De La Rama et al. |
| 2015/0374991 A1 | 12/2015 | Morris et al. |
| 2016/0001072 A1 | 1/2016 | Gelfand et al. |
| 2016/0129244 A1 | 5/2016 | Westlund |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021163 A1 | 1/2017 | Westlund et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326354 A1 | 11/2017 | Westlund et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |
| 2018/0256440 A1 | 9/2018 | Francois et al. |
| 2018/0280692 A1 | 10/2018 | Gelfand et al. |
| 2018/0326209 A1 | 11/2018 | Gelfand et al. |
| 2019/0247656 A1 | 8/2019 | Bauer |
| 2019/0255322 A1 | 8/2019 | Bauer et al. |
| 2019/0351229 A1 | 11/2019 | Westlund et al. |

FOREIGN PATENT DOCUMENTS

| | | |
|---|---|---|
| CN | 102762250 A | 10/2012 |
| EP | 0993840 A1 | 4/2000 |
| EP | 1304135 A2 | 4/2003 |
| EP | 0605796 B1 | 8/2003 |
| EP | 2489395 A1 | 8/2012 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | WO-9407564 A2 | 4/1994 |
| WO | WO-9508357 A1 | 3/1995 |
| WO | WO-9964105 A1 | 12/1999 |
| WO | WO-9965561 A1 | 12/1999 |
| WO | WO-0100273 A1 | 1/2001 |
| WO | WO-02058785 A1 | 8/2002 |
| WO | WO-03005887 A2 | 1/2003 |
| WO | WO-03094855 A1 | 11/2003 |
| WO | WO-2005018524 A2 | 3/2005 |
| WO | WO-2006063339 A2 | 6/2006 |
| WO | WO-2006110338 A1 | 10/2006 |
| WO | WO-2006115877 A1 | 11/2006 |
| WO | WO-2007053508 A1 | 5/2007 |
| WO | WO-2008092246 A1 | 8/2008 |
| WO | WO-2008094344 A1 | 8/2008 |
| WO | WO-2009006337 A1 | 1/2009 |
| WO | WO-2009134459 A2 | 11/2009 |
| WO | WO-2010029842 A1 | 3/2010 |
| WO | WO-2010148412 A1 | 12/2010 |
| WO | WO-2011094631 A1 | 8/2011 |
| WO | WO-2011158410 A1 | 12/2011 |
| WO | WO-2012106533 A2 | 8/2012 |
| WO | WO-2013131187 A1 | 9/2013 |
| WO | WO-2013188965 A1 | 12/2013 |
| WO | WO-2014008171 A1 | 1/2014 |
| WO | WO-2015075548 A1 | 5/2015 |
| WO | WO-2015109401 A1 | 7/2015 |
| WO | WO-2019154834 A1 | 8/2019 |
| WO | WO-2019154837 A1 | 8/2019 |
| WO | WO-2019154839 A1 | 8/2019 |

OTHER PUBLICATIONS

Antonica A., et al., "Vagal Control of Lymphocyte Release from Rat Thymus," Journal of the Autonomic Nervous System, Elsevier, vol. 48(3), Aug. 1994, pp. 187-197.

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.

Borovikova L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.

Borovikova L.V., et al., "Vagus Nerve Stimulation Attenuates the Systemic Inflammatory Response to Endotoxin," Nature, Macmillan Magazines Ltd, vol. 405, May 25, 2000, pp. 458-462.

Chinese Search Report for Application No. CN2013/80023357.5, dated Jul. 24, 2015.

Co-pending U.S. Appl. No. 15/606,867, filed May 26, 2017.

(56) References Cited

OTHER PUBLICATIONS

Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.
Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.
De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.
Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.
Escher, Doris J.W. et al., "Clinical Control of Respiration by Transvenous Phrenic Pacing," American Society for Artificial Internal Organs: Apr. 1968—vol. 14—Issue 1—pp. 192-197.
European Search Report for Application No. 13758363, dated Nov. 12, 2015.
European Search Report for Application No. EP17169051.4, dated Sep. 8, 2017, 7 pages.
Extended European Search Report for Application No. 14864542.7, dated Jun. 2, 2017, 8 pages.
Extended European Search Report for Application No. 15740415.3, dated Jul. 7, 2017.
Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.
Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Huffman, William J. et al., "Modulation of Neuroinflammation and Memory Dysfunction Using Percutaneous Vagus Nerve Stimulation in Mice," Brain Stimulation, 2018.
Ishii, K. et al., "Effects of Bilateral Transvenous Diaphragm Pacing on Hemodynamic Function in Patients after Cardiac Operations," J. Thorac. Cardiovasc. Surg., 1990.
Japanese Office Action in corresponding Japanese Application No. 2014-560202, dated Dec. 6, 2016, 4 pages.
Japanese Office Action in corresponding Japanese Application No. 2014-560202, dated Oct. 17, 2017, 5 pages.
Kawashima K., et al., "Extraneuronal Cholinergic System in Lymphocytes," Pharmacology & Therapeutics, Elsevier, vol. 86, 2000, pp. 29-48.
Levine S., et al., "Rapid disuse atrophy of diaphragm fibers in mechanically ventilated humans," New England Journal of Medicine, 2008, vol. 358, pp. 1327-1335.
Lungpacer: Therapy, News.< http://lungpacer.com>. Accessed Dec. 27, 2016.
Madretsma, G.S., et al., "Nicotine Inhibits the In-vitro Production of Interleukin 2 and Tumour Necrosis Factor-α by Human Mononuclear Cells," Immunopharmacology, Elsevier, vol. 35 (1), Oct. 1996, pp. 47-51.
Marcy, T.W. et al., "Diaphragm Pacing for Ventilatory Insufficiency," Journal of Intensive Care Medicine, 1987, vol. 2 (6), pp. 345-353.
Meyyappan R., "Diaphragm Pacing during Controlled Mechanical Ventilation: Pre-Clinical Observations Reveal a Substantial Improvement in Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," Pace, Blackwell Publishing, Inc, vol. 30(1), Jan. 2007, pp. S215-S218.
Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing, Master of Science Coursework project", Simon Fraser University, Mar. 2013.
Sarnoff, S.J. et al., "Electrophrenic Respiration," Science, 1948, vol. 108, p. 482.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.
Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.
Scheinman R.I., et al., "Role of Transcriptional Activation of IκBα in Mediation of Immunosuppression by Glucocorticoids," Science, vol. 270, Oct. 13, 1995, pp. 283-286.
Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.
Steinlein, O., "New Functions for Nicotinic Acetylcholine Receptors?," Behavioural Brain Research, vol. 95, 1998, pp. 31-35.

(56) References Cited

OTHER PUBLICATIONS

Sternberg E.M., (Series Editor) "Neural-Immune Interactions in Health and Disease," The Journal of Clinical Investigation, vol. 100 (11), Dec. 1997, pp. 2641-2647.

Sykes., A.P., et al., "An Investigation into the Effect and Mechanisms of Action of Nicotine in Inflammatory Bowel Disease," Inflammation Research, vol. 49, 2000, pp. 311-319.

Toyabe S., et al., "Identification of Nicotinic Acetylcholine Receptors on Lymphocytes in the Periphery as well as Thymus in Mice," Immunology, vol. 92, 1997, pp. 201-205.

Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.

Wanner, A. et al., "Trasvenous Phrenic Nerve Stimulation in Anesthetized Dogs," Journal of Applied Physiology, 1973, vol. 34 (4), pp. 489-494.

Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.

Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

Whaley K., et al., "C2 Synthesis by Human Monocytes is Modulated by a Nicotinic Cholinergic Receptor," Nature, vol. 293, Oct. 15, 1981, pp. 580-582 (and reference page).

PCT Search Report dated Oct. 26, 2018 for PCT Application No. PCT/IB2018/000603, 7 pages.

PCT Search Report and Written Opinion dated Oct. 17, 2018 for PCT Application No. PCT/US2018/043661, 13 pages.

\* cited by examiner

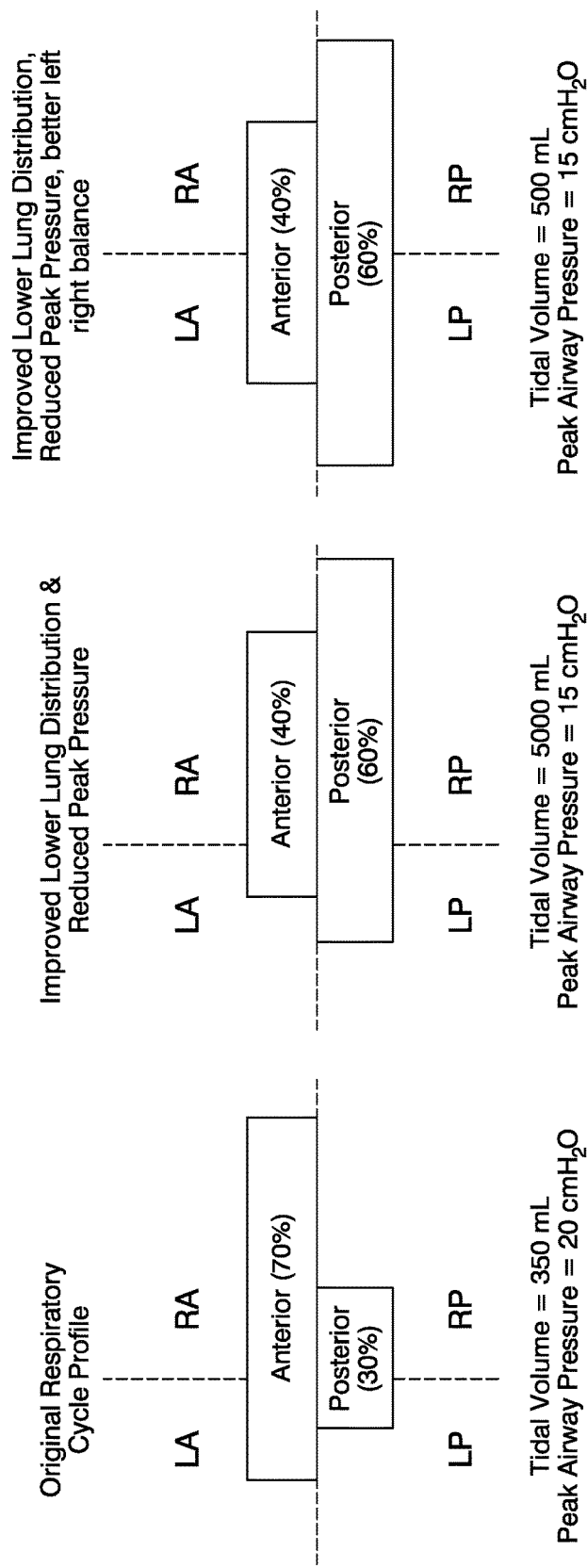
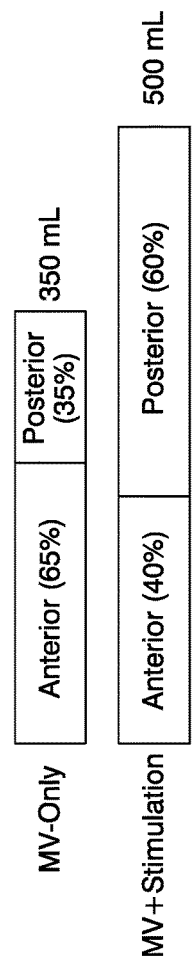
FIG. 18A
FIG. 18B
FIG. 18C
FIG. 18D

SYSTEMS AND METHODS FOR SENSING AND STIMULATION

CROSS-REFERENCE TO RELATED APPLICATION

This application claims priority to U.S. Provisional Application No. 62/848,739, filed on May 16, 2019, which is hereby incorporated by reference in its entirety.

TECHNICAL FIELD

The embodiments of this disclosure generally relate to methods and devices (including systems) for sensing and delivering stimulation. More specifically, the present disclosure is directed to methods and systems for sensing and delivering stimulation to nerves and/or muscles.

BACKGROUND

Patients in hospital Intensive Care Units (ICUs) may experience impairment in their ability to breathe volitionally due to their underlying disease condition and require positive pressure mechanical ventilation (PPMV) and/or other means of External Respiratory Support, collectively ERS, to provide ventilatory assistance. ERS is often used in combination with sedation in the ICU to provide artificial ventilation for these critically ill individuals. Additionally, many patients undergoing surgery under general anesthesia, for example in hospital Operating Rooms (ORs), or procedures requiring anesthesia or sedation, for example in hospital Emergency Rooms (ERs), commonly require ERS for ventilatory assistance while anesthetized or sedated.

Although mechanical ventilation is a life-sustaining modality, when combined with sedation or anesthesia it interferes with active contraction of the diaphragm. Prolonged totally controlled mechanical ventilation can result in the complete absence of neural activation and mechanical activity of the diaphragm and has been shown to induce muscle atrophy, proteolysis, and reactive oxygen species liberation, leading to rapid losses in diaphragmatic function, a syndrome known as Ventilator-Induced Diaphragmatic Dysfunction (VIDD). These patients are also known to experience higher levels of lung, brain, heart and other organ injury. They are also at higher risk of other comorbidities including infection and sepsis, and each day on ERS increases the risk of death.

Approximately 15 million ICU patients require mechanical ventilation annually. Further, approximately a third of those patients will require prolonged weaning to overcome ventilator dependency. Most patients who require diaphragm weaning exhibit diaphragmatic atrophy and dysfunction. Overall, patients requiring mechanical ventilation end up with prolonged and lengthy ICU/hospital stays, higher healthcare costs, poor long-term functional outcomes, and increased respiratory complications and mortality.

Most methods of ERS provide means of gas exchange that differ from natural respiration. When positive pressure ventilation is used, ventilator induced lung injury (VILI) occurs readily, in the form of high volume injury known as barotrauma and a low volume injury known as atelectasis. These non-natural methods of breathing can lead to changes in the total volume of air provided to a patient's lungs and also shift the distribution of the air between various lung regions (e.g. anterior, posterior, left, right, upper, lower, etc.). It is believed the pulmonary stretch receptors, in patients receiving certain types of ERS such as positive pressure ventilation, provide aberrant signals to the brain leading to inflammatory and other processes which affect multiple organs and can induce further injury such ventilator induced brain injury (VIM) which leads to cognitive impairment. Because the diaphragm muscle typically assists with pre-loading venous blood into the heart, and the high pressure of positive pressure ventilators increases thoracic pressure, the hearts of MV patients with inactive diaphragms can be susceptible to over-work injury. Patients are also susceptible to a higher incidence of ventilator-acquired pneumonia and nosocomial infections (VAP) and sepsis.

The onset of VIDD, VILI, VAP, VIBI, and other ERS-induced injuries are rapid, leading to slower patient recovery, increased risk for further complications, prolonged ventilator dependence, longer stays in the ICU, escalating hospitalization costs, and a risk of death which increases with each additional day on mechanical ventilation.

SUMMARY

Embodiments of the present disclosure relate to, among other things, systems, devices, and methods for providing respiratory support. Embodiments include applying stimulation to one or more anatomical targets. Embodiments of the systems and methods described herein, may be used with alternatives and/or supplements to MV and/or may incorporate ERS, such as, for example, stimulation of respiratory nerves and/or respiratory muscles. Each of the embodiments disclosed herein may include one or more of the features described in connection with any of the other disclosed embodiments.

Embodiments of the present disclosure relate to, among other things, systems, devices, and methods for applying stimulation to tissue. Embodiments of the systems and methods described herein, may be used with alternatives and/or supplements to external respiratory support, such as, for example, stimulation of respiratory nerves and/or respiratory muscles. Each of the embodiments disclosed herein may include one or more of the features described in connection with any of the other disclosed embodiments.

In one example, a method of stimulating tissue may comprise delivering a first stimulation (which may comprise a first value of a stimulation parameter) to tissue via a stimulation device, measuring an impedance of lung tissue, based on the impedance, determining a second value of the stimulation parameter of a second stimulation, wherein the second value is different than the first value; and delivering the second stimulation to tissue via the stimulation device.

Any of the methods disclosed herein may include any of the following features. The method may further comprise calculating a lung gas parameter based on the impedance, and/or comparing the lung gas parameter to a pre-determined lung gas parameter. Determining the second value may include calculating the second value based on the lung gas parameter. The lung gas parameter may correspond to an air distribution between the posterior and anterior regions of the lungs, an air distribution between the superior and inferior regions of the lungs, an air distribution between the left and right lungs, and/or one or more lung volumes. Delivering the first stimulation, delivering the second stimulation, or both, may include delivering electrical stimulation. Delivering the second stimulation may include delivering stimulation to a phrenic nerve, and/or delivering stimulation that causes contraction of a respiratory muscle. The impedance may be measured via one or more sensors placed on or in the patient. The stimulation device may include at least one electrode and methods herein may include positioning the stimulation device within a patient such that the at least one electrode is proximate a phrenic nerve.

An exemplary method for stimulating tissue may include measuring a bioelectrical impedance, determining a first value of a lung gas parameter based on the impedance, comparing the first value to a pre-determined value of the lung gas parameter, determining one or more stimulation parameters based on the comparison of the first value to the pre-determined value, and delivering a stimulation signal, including the one or more stimulation parameters to tissue. The lung gas parameter may correspond to a distribution of air between portions of lungs.

Any of the methods disclosed herein may include any of the following features. The method may further comprise, determining a first lung volume, prior to delivering the stimulation signal, and determining a second lung volume, after delivering the stimulation signal. Each of the first lung volume and the second lung volume may be a volume of an inferior region or an anterior region of a lung. The stimulation parameter may include a duration, a pulse width, a frequency, an amplitude, or a combination thereof. The stimulation signal may be delivered via at least one electrode and the bioelectrical impedance may be measured via the at least one electrode. Comparing the first value to the pre-determined value of the lung gas parameter may include comparing the first value to a pre-determined range of values. Delivering the stimulation signal may cause a contraction of a respiratory muscle. The bioelectrical impedance may be a first bioelectrical impedance, the stimulation signal may be a first stimulation signal, and the one or more stimulation parameters are first stimulation parameters, and the method may further comprise measuring a second bioelectrical impedance, determining a second value of the lung gas parameter based on the second bioelectrical impedance, comparing the second value to the first value or the pre-determined value, determining one or more second stimulation parameters, based on the comparison of the second value to the first value or the pre-determined value, and/or delivering a second stimulation including the one or more second stimulation parameters.

An example system for stimulating tissue may comprise a stimulation device, an impedance sensor, and a control unit configured to: receive an impedance signal from the impedance sensor, determine a first value of a lung gas parameter based on the impedance signal, the lung gas parameter corresponding to a distribution of air between portions of lungs; compare the first value to a pre-determined value of the lung gas parameter, determine one or more stimulation parameters based on the comparison of the first value to the pre-determined value, and deliver a stimulation signal, including the one or more stimulation parameters, to tissue, via the stimulation device.

Any of the systems or methods disclosed herein may include any of the following features. The system may further comprise an external respiratory support device. The impedance sensor may be part of an array of impedance sensors, and the array may be configured to be affixed to an exterior of the patient. The control unit may be further configured to generate an image corresponding to the distribution of air between portions of lungs.

BRIEF DESCRIPTION OF THE DRAWINGS

The accompanying drawings, which are incorporated in and constitute a part of this specification, illustrate non-limiting embodiments of the present disclosure and together with the description serve to explain the principles of the disclosure.

FIGS. 18A-18D illustrate graphic depictions of lung gas volume distributions varying in response to respiratory muscle stimulation, according to one or more embodiments;

DETAILED DESCRIPTION

Figure 1:
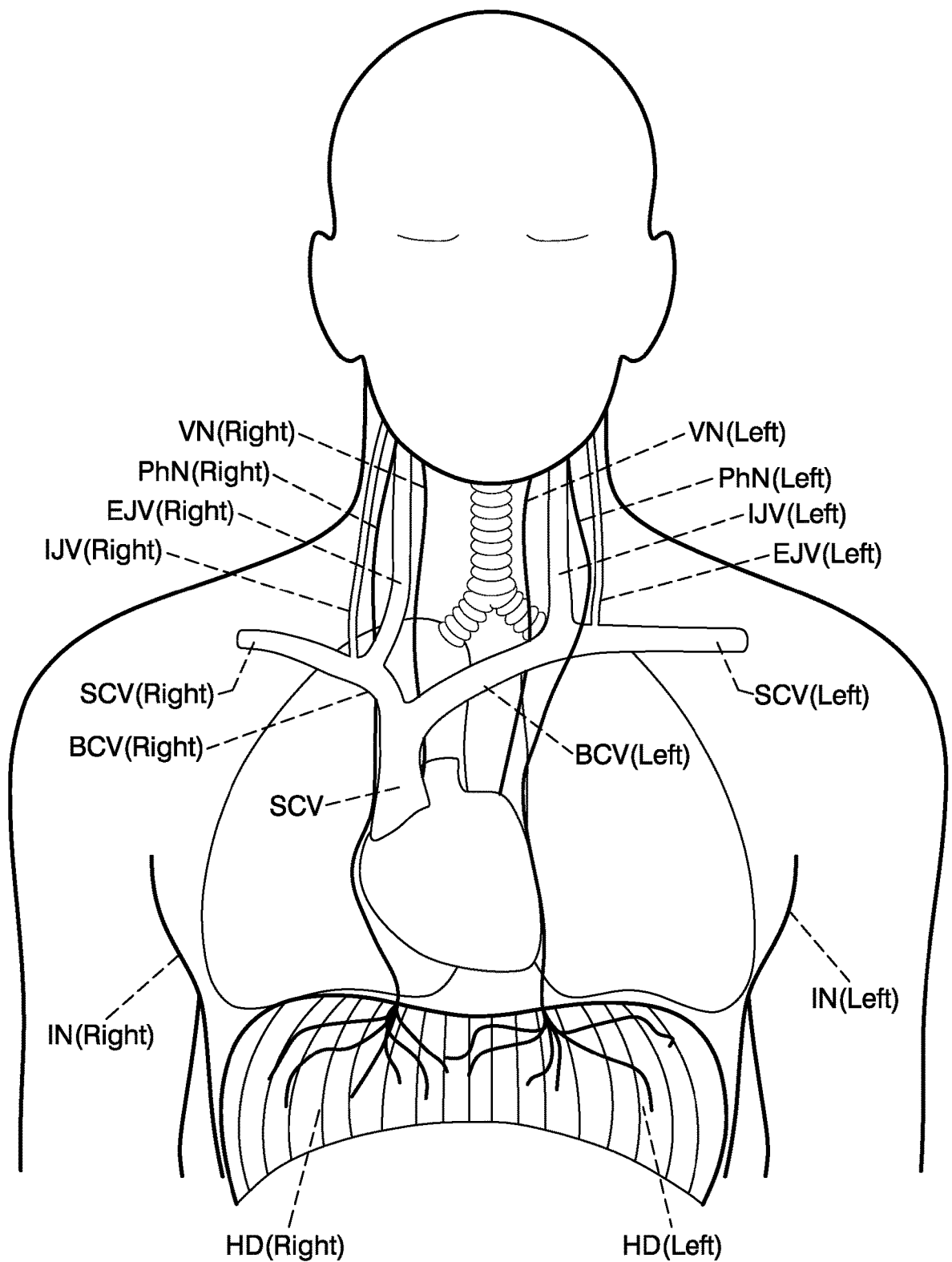
FIG. 1 illustrates the anatomy of selected tissues, blood vessels, nerves, and organs in a person's head, neck, and torso, according to one or more embodiments.

Phrenic nerve stimulation, diaphragm muscle pacing, and transcutaneous stimulation have been considered to help exercise the patient's respiratory muscles (e.g. diaphragm, intercostals, abdominal, etc.) to address the issues referred to above. Various systems and methods for sensing, stimulating, and/or and providing respiratory support are described herein. It should be understood that any component, step, or process of a described method or component or element of a described system may be used in combination with any other component, step, or process of a method or component or element of a system described within.

In general, all publications and patent applications mentioned in this specification are herein incorporated by reference in their entirety to the same extent as if each individual publication or patent application was specifically indicated to be incorporated by reference. For example, embodiments of the present disclosure may be used in combination with one or more systems, catheters, apparatuses, and electrodes described in U.S. Pat. Nos. 8,571,662, 9,242,088, 9,333,363, 9,776,005, 10,039,920, 10,293,164, U.S. Pat. Pub. 2015/0045810, U.S. Pat. Pub. 2019/0001126, U.S. Pat. Pub. 2019/0175908, U.S. Pat. Pub. 2019/0038894, and/or U.S. Pat. Pub. 2020/0147364; the disclosures of all of which are hereby incorporated by reference.

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative, rather than a restrictive, sense.

The different embodiments of the various medical device components may be combined and used together in any logical arrangement. Furthermore, individual features or elements of any described embodiment may be combined with or used in connection with the individual features or elements of other embodiments. The various embodiments may further be used in different contexts than those specifically described herein. For example, the disclosed electrode structures may be combined or used in combination with various deployment systems known in the art for various diagnostic and/or therapeutic applications.

For purposes of this disclosure, muscles of respiration (respiratory muscles) may refer to any muscles that can contribute to, or participate in, inhalation, exhalation, coughing or any other activity for moving air into or out of a human being. In general, these muscles aid the expansion and contraction/compression of the thoracic cavity, abdominal region, or other areas associated with respiration. Examples of respiratory muscles include the diaphragm, intercostal muscles, and accessory muscles (sternocleidomastoid, scalene muscles (anterior, middle and posterior scalene)). Other exemplary muscles of respiration include serratus anterior, pectoralis major and pectoralis minor, trapezius, latissimus dorsi, erector spinae, ilocostalis lumborum, quadratus lumborum, serratus posterior superior, serratus posterior inferior, levatores costarum, transversus thoracic, levator lavii superioris alaeque nasi and sublavius muscles. Other respiratory muscles, such as those that support exhalation, include the abdominal wall muscles (rectus abdominis, transverse abdominis, external oblique muscle and internal oblique muscle) as well as the internal intercostal muscles. The respiratory muscle stimulation systems and apparatuses described herein may be used to activate any of these or other related respiratory muscles.

One or more methods described herein may use electrical stimulation to induce contraction of the respiratory muscles using energy sources, such as, for example, electrodes which can be placed external or inside the patient. External or implanted controllers (e.g. a pacemaker-like device) may be used to manage the delivery of the energy.

In some embodiments, a respiratory muscle stimulation device activates muscle contraction by stimulating one or more phrenic nerves. The two phrenic nerves, which control activation of the diaphragm, run through the thorax, along the left and right sides of the heart, and then to the diaphragm. Phrenic nerve stimulation may be performed by electrically stimulating one or both phrenic nerves to control the patient's respiratory muscle (e.g., diaphragm and/or one or more other respiratory muscles). In some embodiments, stimulation of one or more phrenic nerves may induce a respiratory cycle.

In some embodiments, an easy-to-place minimally invasive device is designed to stimulate a respiratory muscle of patients, to provide a more natural method of respiration, to reduce injury to the body, and facilitate patients regaining independent breathing.

In some embodiments, devices and systems may include a respiratory muscle activator, a lung gas distribution sensor, and a controller to adjust the parameters of the muscle activator to improve/maintain an optimal gas balance in various regions of a patient's lungs.

In at least one embodiment, a respiratory therapy system may be configured for managing the distribution of gas (e.g., air) in regions of a patient's lungs. The system may comprise a control unit, a stimulation array, and/or a plurality of impedance or other gas distribution (e.g. ultrasonic, MRI, CT, etc.) sensors. The control unit may be configured to manage the performance of the respiratory therapy system. Further, the control unit may be configured to receive a bioelectrical impedance or other gas distribution signal, analyze the bioelectrical impedance or gas distribution signal, determine a lung gas parameter value (e.g., an approximate air distribution between the posterior and anterior regions of the lungs, an air distribution between the left and right sides of the lung, a volume, and/or a pressure), and/or comparing the lung gas parameter value to a lung gas parameter desired value (e.g., a predetermined value). The control unit may also be configured to adjust a stimulation parameter if a measured lung gas parameter value deviates from a desired lung gas parameter value.

The stimulation array may be configured to deliver energy via energy sources known in the art (e.g. electrical, ultrasonic, electromagnetic, etc.). The delivery of energy by the stimulation array may cause contraction of a respiratory muscle. The stimulation array may be functionally connected to the control unit. The stimulation array may comprise electrodes, electrodes placed externally to a subject, electrodes placed internally to a subject, or electrodes placed externally to a subject and electrodes placed internally to a subject. The stimulation array may include a linear array of electrodes or a two-dimensional array of electrodes. In addition, or alternatively, the stimulation may comprise energy sources other than electrodes (e.g. transducers, electromagnetic coils, lasers, etc.). The stimulation array may include, be disposed on, or be electrically connected to a catheter, needle, and/or transcutaneous or subcutaneous lead. The stimulation array may comprise an array for stimulation of a respiratory muscle on the right side of the patient, an array for stimulation of a respiratory muscle on the left side of the patient, or both. In some embodiments, the stimulations levels for the array for stimulation of a respiratory muscle on the right side of the patient and the array for stimulation of a respiratory muscle on the left side of the patient may be independently controlled.

The plurality of impedance or other gas distribution sensors may be configured to acquire a bioelectrical impedance signal from the patient. The impedance sensors may be functionally connected to the control unit. The impedance sensors may comprise electrodes, electrodes placed externally to a subject, electrodes placed internally to a subject, or electrodes placed externally to a subject and electrodes placed internally to a subject. In some embodiments, at least one impedance sensor is positioned external to a subject, and at least one impedance sensor is positioned below the skin of the subject. The impedance sensors may also be configured to stimulate respiratory muscles. In some embodiments, impedance sensors placed internally to the subject and impedance sensors placed externally to the subject may transmit stimulation to control portions of an inhalation phase and an exhalation phase.

In some embodiments, the system may be configured to reduce signaling from a pulmonary stretch receptor to reduce at least one of atelectasis, barotrauma, VILI, and/or VIBI. The system may further comprise an external positive pressure respiratory device for moving gas into the lungs of the patient. The system may detect the action of the positive pressure respiratory device with a sensor or may be functionally connected with the positive pressure respiratory device. In some embodiments, the controller may manage input from the impedance sensors and the external respiratory support device to adjust the stimulation energy to improve the gas balance in a subject's lungs. The system may further include at least one physiological sensor, functionally connected to the control unit, for obtaining patient physiological data relating to at least one of tidal volume, a lung volume (e.g., a volume of a lung region), respiratory pressure, respiratory rate, work of breathing, $CO_2$ saturation, oxygen saturation, temperature, blood pressure, heart rate, blood oxygen levels, motion, movement, and/or brain activity.

In some embodiments, devices and systems may include a respiratory muscle activator, an external respiratory support device, a lung gas distribution sensor, and/or a controller. The controller may be configured to adjust the parameters of the muscle activator and external respiratory support device to improve/maintain a beneficial gas balance in various regions of the patient's lungs during one or more respiratory cycles.

Devices and systems may be configured to manage the disruption of accumulated mucus, fluids, and other lung secretions. In some embodiments, devices and systems may include a stimulation array for delivering energy. The delivered energy may cause contraction of one or more respiratory muscles at a frequency, intensity, and specified waveform designed to expose, dislodge, disrupt, liberate, and/or transport accumulated mucus, fluids, and/or other secretions in a patient's lungs so they can be readily removed from a patient.

In some embodiments, devices and systems may be configured to open lower/inferior/distal/posterior lung regions so that accumulated mucus, fluids, and/or other secretions are exposed, dislodged, disrupted, liberated, transported, and/or otherwise acted upon so they can be readily removed from a patient. In some aspects, the tidal volumes of a patient may increase over time.

Clearance of secretions and mucus from the lungs in healthy individuals is accomplished primarily by the body's normal mucociliary action, coughing, and the active movement of an individual's body. Under physiologically normal conditions, these mechanisms are efficient at dislodging and removing secretions, mucus, contaminants, and/or other fluid built-up in the lungs (collectively referred to respiratory secretions). Impairment of the normal mucociliary clearance system, sedentary or bedridden periods of time, or hypersecretion of respiratory mucus can result in an accumulation of mucus and debris in the lungs. For patients receiving external respiratory support such as positive pressure mechanical ventilation, the issue can worsen further as the pressure from the ventilator forces secretions into the lower/posterior lung regions, as these lower lobe regions typically collapse over time (e.g. atelectasis), trapping secretions and harmful bacteria, and the patient's situation may be further complicated by the inability to cough.

Chest physiotherapy is often clinically effective and is typically a part of standard medical practice to enhance respiratory mucus dislodgement/transport. Chest physiotherapy often includes mechanical manipulation of the chest, external vibratory action, and directed cough. Some have attempted to develop devices to help mechanically dislodge accumulated lung secretions. However, as mentioned previously, the lower/posterior regions of many patients collapse (e.g. atelectasis), trapping secretions, and standard methodologies (e.g., those involving forced air or positive airway pressure) have not been effective at disrupting or loosening these materials.

The respiratory muscle stimulation systems described herein may be used to both open the lower/posterior lung regions and provide the added benefit of loosening respiratory secretions. The secretion disruption capability may be implemented anytime during the respiratory cycle (e.g., during the inhalation, exhalation, etc.). By using stimulation on either or both inspiratory muscles and expiratory muscles or abdominal muscles, coordinated contractions at desired frequencies can be used to loosen these secretions. Stimulation can be focused on one side versus another, for example on the right side, depending on the patient situation.

In one or more embodiments, a method for managing clearance of accumulated mucus and other respiratory secretions (e.g., using a respiratory therapy system) may comprise stimulating an inspiratory muscle (e.g. diaphragm muscle) to contract at a frequency, intensity, and specified waveform suitable to open the lower/posterior lung regions and expose, dislodge, disrupt, liberate, and/or transport accumulated respiratory secretions. After respiratory secretions are exposed, dislodged, disrupted, liberated, and/or transported, they may be readily removed from a subject. The inspiratory muscle may be stimulated via, for example, a stimulation array configured to deliver energy. The stimulation array may be functionally connected to a control unit, and the control unit may be configured for managing the performance of the respiratory therapy system. The stimulation array may comprise an array for stimulation of a respiratory muscle on the right side of the patient, an array for stimulation of a respiratory muscle on the left side of the patient, or both. In some embodiments, the stimulations levels for the array for stimulation of a respiratory muscle on the right side of the patient and the array for stimulation of a respiratory muscle on the left side of the patient may be independently controlled.

In some embodiments, a method for managing clearance of accumulated mucus and other respiratory secretions (e.g., using the respiratory therapy system) may comprise increasing gas distribution in the lower/posterior lungs during or after treatment. The tidal volume of breaths during or after treatment may increase. The inspiratory muscle may be a diaphragm muscle and/or an intercostal muscle. The method may further include stimulating an expiratory muscle. In some embodiments, at least one impedance sensor is used to monitor the lung gas distribution by region. The method may include using an air flow sensor, a pressure sensor, and/or a volume sensor. In some embodiments, the method further includes using an external positive pressure respiratory device to move gas into the lungs of the subject.

In some embodiments, a mechanically ventilated subject may be weaned faster after respiratory secretion mobilization and/or may have an increased tidal volume. The respiratory therapy system used with exemplary methods may either detect the action of the positive pressure respiratory device with a sensor, or may be functionally connected with the positive pressure respiratory device. The system may further include at least one physiological sensor, functionally connected to the control unit, for obtaining patient physiological data relating to at least one of tidal volume, lung volume (e.g., a volume of a lung region), respiratory pressure, respiratory rate, work of breathing, $CO_2$ saturation, oxygen saturation, temperature, blood pressure, heart rate, blood oxygen levels, and/or brain activity.

In some embodiments, a respiratory therapy system configured to manage the disruption of accumulated mucus and other lung secretions may comprise a control unit for managing the performance of the respiratory therapy system, a stimulation array, and/or a stimulation algorithm. The stimulation array may be functionally connected to a control unit, and the control unit may be configured for managing the performance of the respiratory therapy system. The stimulation array may comprise an array for stimulation of a respiratory muscle on the right side of the patient, an array for stimulation of a respiratory muscle on the left side of the patient, or both. In some embodiments, the stimulations levels for the array for stimulation of a respiratory muscle on the right side of the patient and the array for stimulation of a respiratory muscle on the left side of the patient may be independently controlled.

The stimulation algorithm may include one or more waveforms configured to activate an inspiratory muscle (e.g. diaphragm muscle, intercostal, abdominal, etc.) to contract at a frequency, intensity, and specified waveform to open the lower/posterior lung regions. The contraction of the inspiratory muscle may expose, dislodged, disrupt, liberate, and/or transport respiratory secretions so they can be readily removed from a patient.

The respiratory therapy system configured to manage the disruption of accumulated mucus and other lung secretions may further include an impedance or other lung sensor to determine a lung function parameter. The controller may include an algorithm configured to receive data on a lung function parameter and communicate the lung function parameter to a user. In some embodiments, the controller may analyze a bioelectrical impedance signal and determine changes in air distribution between the posterior and anterior regions of the lungs. This determination may be communicated to the user.

In some embodiments, a minimally invasive device may be configured to stimulate a respiratory muscle of a patient. The device may include an array of energy emitters and an anchoring system for securing the device. The device may also be configured such that stimulation energy can be provided to a target nerve and/or one or more muscles over extended periods of time.

In some embodiments, a respiratory therapy system may comprise a control unit, one or more energy emitters, a delivery cannula, an orientation means, one or more anchors, and/or a sensor for determining a lung gas parameter. The control unit may be configured to manage the performance of the respiratory system. The control unit may be configured to receive a signal from the sensor, analyze the signal from the sensor, determine a lung gas parameter value (e.g., an approximate air distribution between the posterior and anterior regions of the lungs, an air distribution between the left and right sides of the lungs, a volume [e.g., tidal volume, regional lung volume, etc.], and/or a pressure [e.g., MIP, MEP, Peak Pressure, Plateau Pressure, Pressure-Time-Product, etc.], and/or comparing the lung gas parameter value to a lung gas parameter desired value (e.g., a predetermined value, a calculated value, etc.). The control unit may also be configured to adjust a stimulation parameter if a measured lung gas parameter value deviates from a desired lung gas parameter value.

The one or more energy emitters (e.g., stimulation array) may be configured to delivery energy to cause contraction of a respiratory muscle. The one or more energy emitters may be functionally connected to the control unit. The delivery cannula may be configured to guide the one or more energy emitters (e.g., stimulation array) to target tissue. The delivery cannula may comprise an elongated cannula with at least one lumen or channel for receipt of the one or more energy emitters. The delivery cannula may include one or more stimulation windows along the distal portion of the cannula from which energy can be emitted to stimulate a target. The orientation means may be in contact with the delivery cannula, the one or more energy emitters, or both the delivery cannula and the one or more energy emitters. The orientations means may allow for the energy emitters to align with the windows of the delivery cannula. The one or more anchors may be coupled to the one or more energy emitters and may be configured to secure the one or more energy emitters in a tissue location proximate to target tissue.

In some embodiments, a method for stimulating a respiratory nerve in the body of a patient may comprise placing a respiratory muscle stimulation device such that a distal portion of the device (e.g., a lead body) is proximate to a target nerve, and a proximal portion of the stimulation device is external to the patient, supplying electrical energy to the distal portion of the device to stimulate a portion of the target nerve, detecting a response resulting from stimulation of a respiratory nerve, anchoring the lead to the patient so as to mitigate movement of the lead, supplying electrical energy to the distal portion of the device to cause a contraction of a respiratory muscle, and/or contracting the respiratory muscle for a suitable number of times over at least two days. Such methods may increase strength of the respiratory muscle or mitigate the loss of strength of the muscle.

Methods may further include placing a delivery cannula, the delivery cannula comprising an elongated cannula with at least one lumen or channel for receipt of the one or more energy emitters. The delivery cannula may also include one or more stimulation windows along the distal portion of the cannula from which energy can be emitted to stimulate a target. The proximal portion of the respiratory muscle stimulation device may include an orientation means. The orientation means may be in contact with the delivery cannula, the lead body, one or more electrodes on the distal portion of the respiratory muscle stimulation device, or a combination thereof. The orientations means may indicate a preferred orientation with respect to the skin of a patient or preferred location (e.g. left or right, up or down, distal or proximal, etc.).

In some embodiments, the distal portion of the device includes a flexible lead which comprises directional electrodes. The directional electrodes may create an electrical field which, at a given longitudinal location and radial distance in the vicinity of a stimulating electrode, varies in strength depending on the circumferential angular position in relation to the longitudinal axis of the flexible lead. Positioning the respiratory muscle stimulation device may include inserting the flexible lead through a split, peelable cannula delivery system into the body of a patient, removing the split, peelable cannula delivery system from the body of the patient, and creating a longitudinal channel or opening in the split, peelable cannula delivery system such that the flexible lead can be separated from the split, peelable cannula delivery system. In some embodiments, a portion of the lead body changes from a first compact geometric configuration (e.g., prior to placement in the body) to a second geometric configuration (e.g., after placement in the body). The second geometric configuration may be less compact than the first geometric configuration.

In one or more embodiments, a system may include a percutaneous lead including an energy source (e.g., electrodes that dissipate electrical charge, or other energy sources that emit energy of some form including electrical, ultrasound, optical, thermal, or chemical). The energy source may be electrically connected to at least one other energy source. The system may further include a control unit that is in communication with the percutaneous lead to manage the delivery of energy. The control unit may be in communication with one or more sensors to control the desired results by varying the amount of energy delivered. The one or more sensors (e.g., nerve, $O_2$, $CO_2$, motion, airway flow, airway pressure, impedance, EIT, EIS, EMG, ECG, EKG, and/or cognitive function, etc.) may provide feedback to the control unit on the physiological condition of the patient and/or environmental factors and/or the status of external respiratory support device(s).

The system may be configured to deliver energy to cause the contraction of a respiratory muscle. Additionally, or in the alternative, the system may be configured to deliver energy to the vagus nerve to reduce inflammation or sepsis, and/or to favorably change cardiac rhythm. The system may additionally be configured to stimulate any other nerve or muscle.

In some embodiments, the percutaneous lead may include a patch or collar that is placed on the surface of the skin. In other embodiments, the system includes a patch or collar, configured to be placed on skin, that includes a microelectrode energy source of sensors. The lead, patch, or collar may include a chip for identification of the product, preventing unauthorized use, and/or transmit data back to a central data processing location (e.g., where data for more than one patient is processed).

In some embodiments, the percutaneous lead may have an anti-microbial coating and/or a reversible anchoring mechanism (e.g., that prevents lead movement) that can be deployed. In some embodiments, components of a system may communicate via a wireless connection, a Bluetooth connection, or a sonar connection.

In some embodiments, a system may include a structure with multiple energy sources (e.g., electrodes that dissipate energy), a mechanical ventilator, a control unit connected to the energy sources of the structure, and one or more sensors. The control unit and one or more sensors may be similar to control units and sensors described herein. For example, the control unit may be connected to sensors to control synchronization of phrenic nerve stimulation with mechanically ventilated breaths. The system may receive data from the sensors (e.g., motion, airway flow, pressure, EMG, central venous pressure, impedance, etc.). The structure may be configured to be placed on a patient so that the energy source is proximate a phrenic nerve. For example, the structure may be placed transvascularly, transcutaneously, on skin, or transesophageally. In some embodiments, energy delivery by the system may be triggered manually by user action (e.g., button, voice command, touch screen, etc.). In other embodiments, the data received from the sensors may inform the control unit of stimulation parameters (e.g., stimulation timing). The data that informs the control unit of stimulation parameters may include data received from sensors such as motion sensors, airway flow sensors, airway pressure sensors, EMG, EKG, tidal volume sensors, work of breathing sensors, external mechanical work of breathing sensors, $O_2$ level sensors, $CO_2$ level sensors, blood gas sensors, heart rate sensors, and/or stretch receptor signal sensors.

In some embodiments, the system may map the most efficient optimal energy source and/or energy sources which produce undesired effects, based on data received from one or more sensors. The structure may include an antimicrobial coating, a chip, an RFID, a zone that can be viewed better via ultrasound, and/or one or more electrodes placed such that one or more nerves can be stimulated from different directions. In some embodiments, stimulating the nerves from different directions and/or with any stimulation train profile described herein, may reduce fatigue of an associated respiratory muscle. In some embodiments, signals received by the system from the patient module (e.g., lead, electrode, patch) may be transmitted wirelessly through Wi-Fi, Bluetooth, RF, and/or sonar.

In some exemplary methods, one or more previously described structures may be placed proximate to the phrenic nerve or vagus nerve. The structure may be placed percutaneously and/or through the neck. Anatomical landmarks and ultrasound imaging may facilitate placement of the structure. In some embodiments, placement of the structure may be confirmed based on patient reaction (e.g., response to delivered energy), data from one or more sensors (e.g., pressure, volume, impedance, nerve activity), manual palpation, and/or visualization of the diaphragm (e.g., x-ray, fluoroscopy, ultrasound, CT, MRI). Such methods may reconstruct diaphragm strength, prevent diaphragm atrophy, sustain breathing of a patient, and/or prevent lung injury of a patient. The methods may use any device, system, or structure described herein, including those comprising flexible circuits, anchors, delivery cannulas, imaging technology, flexible delivery cannulas, strain relief holes, and/or electrodes.

Respiratory muscle stimulation may be performed either by activating a muscle directly or via stimulation of a related nerve, e.g. (phrenic nerve). Stimulation may include delivery of electrical, ultrasound, magnetic, chemical, or other type of energy known in the art. The energy sources used for stimulation may be placed in close proximity to the nerves, in a blood vessel (delivering energy through the vessel wall), percutaneous, nerve cuffs, transdermal (delivering energy through the skin), or implanted in muscles or adjacent tissues directly.

FIG. 1 illustrates the anatomy of the neck and chest and the relative locations of the left and right phrenic nerves (PhN), vagus nerves (VN), internal jugular veins (IJV), external jugular veins (EJV), brachiocephalic veins (BCV), subclavian veins (SCV), superior vena cava (SVC) and intercostal nerves (IN). The phrenic nerves originate from cervical spinal roots C3, C4 and C5. The left phrenic nerve extends to the left hemidiaphragm (HD) and the right phrenic nerve extends to the right hemidiaphragm (HD). The left phrenic nerve runs posterior to the left subclavian vein, enters the thorax via the superior thoracic aperture & pierces and innervates the inferior surface of the diaphragm. The right phrenic nerve passes anteriorly over the lateral part of the right subclavian artery, courses along the superior vena cava and the pericardium of the right atrium of the heart, pierces the diaphragm at the inferior vena cava opening & innervates the inferior surface of the diaphragm.

Figure 2:
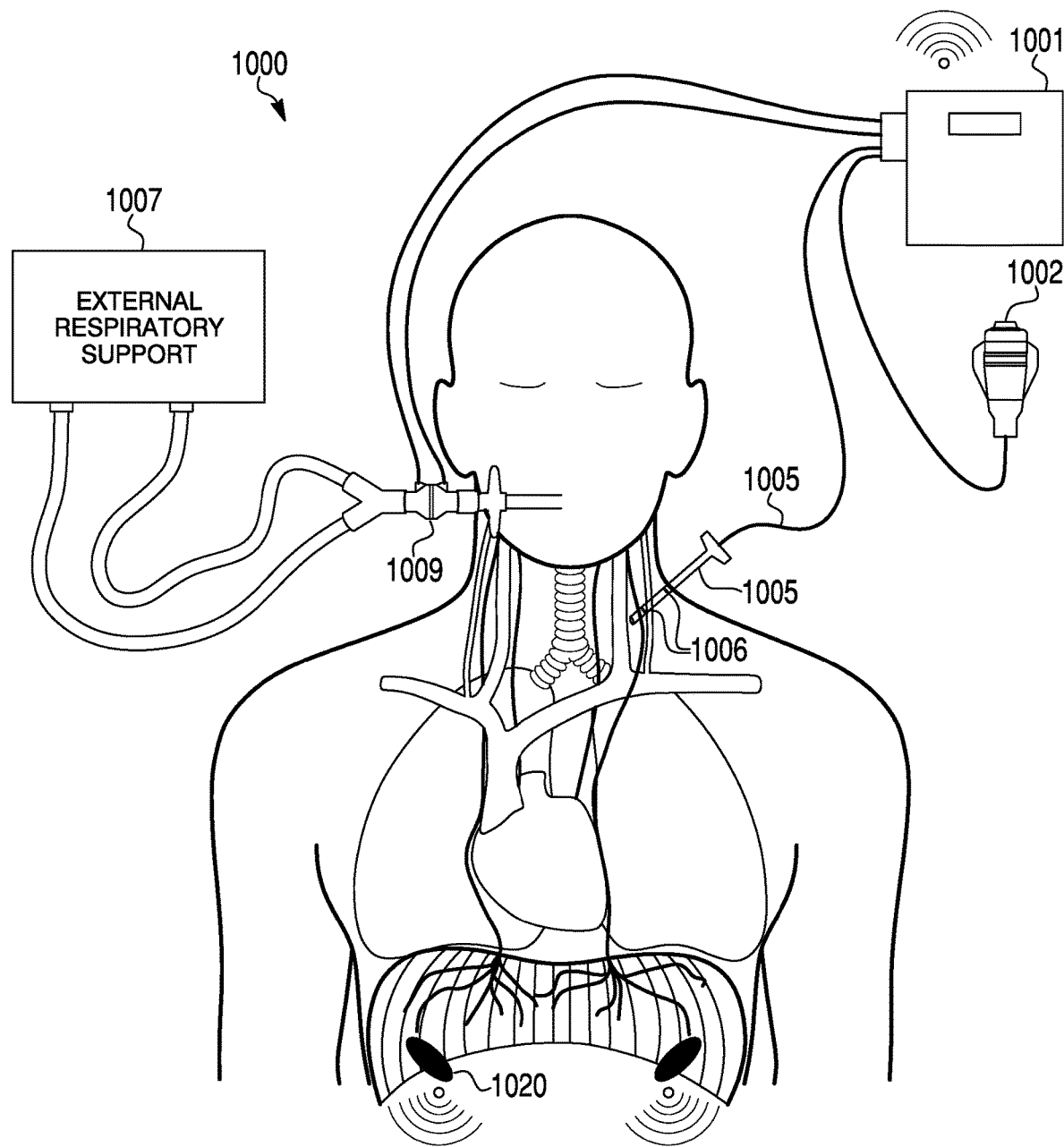
FIG. 2 illustrates the anatomy of selected tissues, blood vessels, nerves, and organs in a person's head, neck, and torso, along with an exemplary respiratory muscle stimulation system, according to one or more embodiments.

FIG. 2 illustrates a medical system 1000 that includes a transcutaneous nerve stimulation lead 1005 and a control unit 1001. The stimulation lead 1005 may include a plurality of energy sources 1006. The energy sources 1006 may be configured to emit, transfer, divert, and/or deliver energy (e.g., electrical energy, magnetic energy, ultrasound, etc.). The lead 1005 may be placed proximate any target nerve or muscle. In some instances, the lead 1005 may be placed in the vicinity of two nerves, such as the left phrenic and vagus nerves. In some instances, two or more leads 1005 may be placed. Each lead 1005 may be operably connected (e.g., hardwired, wireless, etc.) to a control unit 1001. The control unit 1001 may be programmed to perform any of the functions described herein in connection with the system. In some embodiments, the control unit 1001 may be functionally connected (e.g. hardwired, Wi-Fi, RF, etc.) to a remote (e.g., handheld, etc.) controller 1002 to allow a patient or health professional to control operation of the control unit 1001 at a distance from the control unit 1001. The controller 1002 may include a handheld device 1002, as illustrated in FIG. 2. In some examples, the controller 1002 may include a footswitch/pedal, a voice-activated, touch-activated, or pressure-activated switch, or any other form of a remote actuator. The control unit 1001 may include a touch screen and may be supported by a cart, such as the cart shown in FIG. 8. The system may further comprise an external respiratory support device 1007, such as, for example, a mechanical ventilator.

The controller 1002 (e.g., a remote and/or handheld controller) may include buttons that can be pressed by a patient or other user to control breathing patterns. In other examples, a remote controller 1002 may be in the form of a smartphone, tablet, watch or suitable input device. In one example, the controller 1002 may allow a user (e.g., the patient or a healthcare professional) to initiate a sigh breath, which may cause a greater volume of air to enter the patient's lungs than in a previous breath. A sigh breath may result when energy sources 1006 (e.g., electrodes) of lead 1005 are directed to stimulate one or more of the phrenic nerves at a higher level than a normal breath (e.g., a stimulation train having a longer duration of stimulation or having pulses with a higher amplitude, pulse width, or frequency). Higher amplitude stimulation pulses can recruit additional nerve fibers, which in turn can engage additional muscle fibers to cause stronger and/or deeper muscle contractions. Extended pulse widths or extended durations of the stimulation train can deliver stimulation over longer periods of time to extend the duration of the muscle contractions. In the case of respiratory muscle stimulation, a longer duration of a stimulation train with multiple energy pulses has the potential to help expand the lower lung lobes by providing greater or extended negative pressure around the outside of the lungs. Such negative pressure has the potential to help prevent or mitigate a form of low pressure lung injury known as atelectasis. The increased stimulation of the one or more respiratory muscles, for example via phrenic nerve stimulation, may result in a more forceful contraction of the muscle (e.g. diaphragm, intercostal, etc.), causing the patient to inhale a greater volume of air, thereby providing a greater amount of oxygen to the patient. Sigh breaths may increase patient comfort.

In other examples, buttons (e.g., on controller 1002 or control unit 1001) may allow the patient or other user to start and stop stimulation therapy, or to increase or decrease stimulation parameters, including stimulation charge (product of amplitude and pulse width), frequency of pulses in a stimulation train, or breath rate. LED indicators or a small LCD screen (not shown) on the controller may provide other information to guide or inform the operator regarding the stimulation parameters, the feedback from the system sensors, or the condition of the patient. Various set points may be established, and if system information or patient data are detected outside of the pre-determined set points, the system can alarm or otherwise inform a healthcare practitioner (e.g. screen notification, text messages, alarms, etc.).

In some embodiments, the control unit 1001 of the system may be implanted in the patient (not shown), along with the stimulation lead 1005. The implanted system may further include a remote controller and a programmer (not shown) that communicates with control unit 1001 wirelessly. In this embodiment, each of the programmer, control unit 1001, and remote controller 1002 may include a wireless transceiver so that each component can communicate wirelessly with each other. Each of the components can use wireless communication (e.g., Wi-Fi, Bluetooth, RF, Z Wave, etc.) to communicate information, for example to a central data storage center or to a data analysis center.

The control unit 1001 may include all of the electronics, software, and functioning logic necessary to perform the functions described herein. Implanting the control unit 1001 may allow the lead 1005 to function as a permanent breathing pacemaker. A programmer may allow the patient or health professional to modify or otherwise program the nerve stimulation or sensing parameters.

Figure 7:
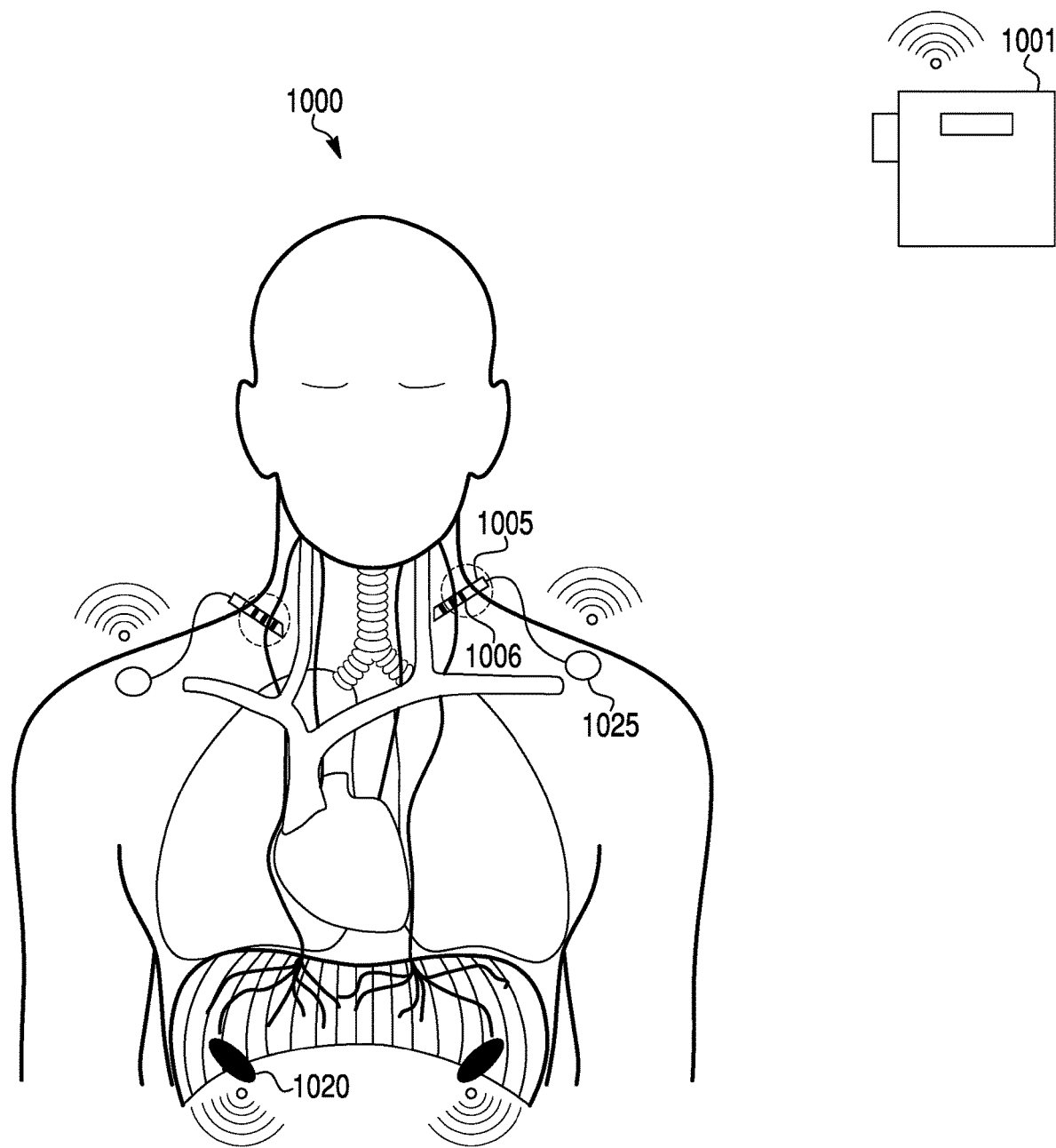
FIGS. 7-9B illustrate the anatomy of selected tissues, blood vessels, nerves, and organs in a person's head, neck, and torso, along with exemplary respiratory muscle stimulation systems, according to some embodiments.

In some embodiments, systems may include a control unit 1001 which is portable (see, e.g., FIG. 7). The portable control unit 1001 may include all of the functionality of control unit of FIG. 2, but it may be carried by a patient or other user to provide the patient with more mobility. In addition to carrying the control unit 1001, the patient can wear the control unit 1001 on a belt, on other articles of clothing, or around his/her neck, for example. In other examples, the control unit 1001 may be mounted to a patient's bed to minimize the footprint of the system in the area around the patient, or to provide portable muscle stimulation in the event a bed-ridden patient needs to be transported or moved to another location.

In further examples, a muscle activation lead 1005 may be placed into and advanced through tissue or through other vessels providing access to the locations adjacent the target nerve(s) (e.g., phrenic nerves), such as: the subclavian, superior vena cava, jugular (see, e.g., FIGS. 9A and 9B), axillary, cephalic, cardiophrenic, brachial or radial veins. In addition, leads 1005 or other stimulation array (e.g. transdermal, etc.) may use other forms of stimulation energy, such as ultrasound, optical, magnetic, to activate the target nerves. In some examples, the system may target other respiratory muscles (e.g., intercostal, abdominal, etc.) either in addition to, or alternatively to, the diaphragm. The energy may be delivered via one or more methods, including transvascular, subcutaneous, nerve cuffs, transdermal stimulation, or other techniques known in the field.

It may be desirable to optimize the way in which external respiratory support 1007 is provided to the patient. In some instances, it may be desirable to ultimately reduce or eliminate the need for a patient to receive external respiratory support 1007. External respiratory support 1007 in FIG. 2 can consist of any device or methods to help manage safe blood gas (e.g., $CO_2$, $O_2$, etc.) levels and or reduce the work of breathing of a patient. Some non-limiting examples include mechanical ventilation, non-invasive ventilation (NIV), CPAP, BiPAP, high-flow oxygen/gas, nasal cannula oxygenation/gas, DPS (Synapse, Avery, etc.), ECCO2, and ECMO.

Mechanical ventilation is the term for artificial ventilation where mechanical means is used to assist or replace spontaneous breathing. This may involve a machine called a ventilator. Mechanical ventilation is considered "invasive" if it involves any instrument penetrating through the mouth (such as an endotracheal tube) or the skin (such as a tracheostomy tube). There are two main types: positive pressure ventilation, where air (or another gas mix) is forced into the trachea via positive pressure, and negative pressure ventilation, where air is drawn into (e.g. sucked into) the lungs (e.g. iron lung, etc.). There are many modes of mechanical ventilation. Mechanical ventilation may be used when the patient's spontaneous ventilation is unable to provide effective gas exchange in the lungs.

Ventilation can also be provided via a laryngeal mask airway (e.g. laryngeal mask), which is designed to keep a patient's airway open during anesthesia or unconsciousness. It is often referred to as a type of supraglottic airway. A laryngeal mask is composed of an airway tube that connects to an elliptical mask with a cuff which is inserted through the patient's mouth, down the windpipe, and once deployed forms an airtight seal on top of the glottis (unlike tracheal tubes which pass through the glottis) to provide a secure or stable airway.

Non-invasive ventilation (NIV) is the use of airway support administered through a face (e.g. oral, nasal, nasal-oral) mask/cannula instead of an endotracheal tube. Inhaled gases are given with positive end-expiratory pressure often with pressure support or with assist control ventilation at a set tidal volume and rate. It is termed "non-invasive" because it is delivered with a mask that is tightly fitted to the face, but without a need for tracheal intubation.

Continuous positive airway pressure (CPAP) is a form of positive airway pressure ventilation, which applies mild air pressure on a continuous basis to keep the airways continuously open in people who are able to breathe spontaneously on their own but may require a level of pressure support. It is an alternative to positive end-expiratory pressure (PEEP). Both modalities may stent the lungs' alveoli open and therefore help recruit more of the lung's surface area for ventilation. PEEP generally refers to devices that impose positive pressure only at the end of the exhalation. CPAP devices generally apply a continuous positive airway pressure throughout the breathing cycle, although some systems do vary pressure during a breathing cycle or over a period of time. Thus, the ventilator itself does not cycle during CPAP, typically no additional pressure above the level of CPAP is provided, and patients must initiate each breath on their own.

Bi-level Positive Airway Pressure (BiPAP) therapy is very similar in function and design to CPAP. BiPAP devices can also be set to include a breath timing feature that measures the amount of breaths per minute a person should be taking. If the time between breaths exceeds the set limit, the machine can force the person to breathe temporarily, increasing the air pressure. The main difference between BiPAP and CPAP machines is that BiPAP machines generally have two or more pressure settings: the prescribed pressure for inhalation (ipap), and a lower pressure for exhalation (epap). The dual settings allow the patient to get more air in and out of their lungs.

Extracorporeal membrane oxygenation (ECMO), which is also known as extracorporeal life support (ECLS), is an extracorporeal technique to provide prolonged cardiac and respiratory support to patients whose heart and lungs are unable to provide an adequate amount of gas exchange. The technology for ECMO is similar to that used during cardiopulmonary bypass, which is typically used to provide shorter-term support. During ECMO, blood is removed from the person's body and passed through a device which removes carbon dioxide and provides oxygen to red blood cells. Long term ECMO patients can often develop respiratory muscle weakness because of muscle inactivity and other causes.

Each of these devices/systems, and any others known in the art, which can be used to manage blood gas levels are collectively referred to as external respiratory support 1007.

In some embodiments, the stimulation device, array, lead 1005, or components of the lead 1005 or parts of the system, for example, electrodes, can also monitor physiological variables of the subject by virtue of their placement in or on the patient's body. In embodiments where the lead 1005 is positioned within one or more central veins, the device can monitor physiological variables including, but not limited to: central venous pressure, temperature, respiration rate, electrocardiogram, impedance, heart rate, flow, $CO_2$, nerve activity, EMG, ECG, mixed venous oxygen saturation, and other variables known in the art. It will be appreciated that one or more sensors discrete from the electrodes, such as one or more of the sensors 1020, may be used to monitor such physiological variables.

In some embodiments, the system may include a breath sensor 1009 for sensing parameters of the external respiratory support 1007 (e.g. mechanical ventilator). In that regard, the breath sensor 1009 may be configured to interface with any standard breathing circuit used in critical care ventilators, and therefore the pacing system is independent of the brand of ventilator used. The breath sensor 1009 as shown in FIG. 2, by virtue of its location in the breathing circuit, can monitor and/or measure several ventilation parameters and communicate such parameters to the control unit 1001. As will be described in more detail below, the breath sensor 1009 may be part of, or used solely as, a feedback control scheme for regulating stimulation administered to the patient. The sensed ventilation parameters may include, but are not limited to, airflow (inspired and/or expired), volume, and/or pressure (airway, esophageal, gastric, and/or some combination/derivative of the former). In some embodiments, the breath sensor 1009 may include, or be in communication with, an accelerometer, gyroscope, and/or motion sensor placed on the thoracic cavity of the patient (e.g., sensors 1020). In some embodiments, one or more other sensors may aid in the procurement of one or more ventilation parameters. The breath sensor 1009 may be connected, by wire or wirelessly, to the control unit 1001. In some embodiments, the signal from the external respiratory support 1007 may be used to control the respiratory muscle activator (e.g., phrenic nerve stimulator, etc.). The example parameters may be measured both to and from the ventilator. For example, in the embodiment shown in FIG. 2, the breath sensor 1009 is external to the external respiratory support 1007, so that the system is independent of external respiratory support 1007 type or model. However, the system may also be integrated to use internal sensors of the external respiratory support 1007, or signals externally supplied by the external respiratory support 1007 can provide the information to the system for proper operation so that an external breath sensor 1009 can be omitted. One or more other sensors may sense nerve or muscle activity and may be used to synchronize respiratory muscle energy stimulation with another event. In one example, a sensor of the system senses when a patient is attempting to breathe and delivers positive pressure ventilation and neuromuscular stimulation to the patient. In some embodiments, this delivery of positive pressure ventilation and neuromuscular stimulation may enhance the efficiency of the respiratory cycle.

The stimulator (e.g., controller, control unit 1001, or similar device) may include a signal generator for providing therapy to the diaphragm and for other respiratory muscles in response to information received from the one or more of the sensors and/or information programmed into the system by the user (e.g., patient or healthcare professional). In that regard, the stimulator may deliver pulses to the stimulation array in accordance with one or more protocols described herein. As will be described in more detail below, in some embodiments, the pulses are generated by the stimulator with characteristics suitable to deliver charge to the phrenic nerves in order to provide enough diaphragm recruitment to satisfy the selected diaphragm contribution (e.g., in volume, pressure, both, or derived parameters from volume and pressure) of the prescribed assist level described above.

Towards that end, the stimulator is configured to deliver fully programmable stimulation, including, but not limited to, the following: any number of pulses, any combination of the defined pulses, any order of delivery of the defined pulses, multiple instances of any defined pulse(s), any frequency of stimulation, and/or any delay between pulses (e.g., interpulse delay, varying interpulse delay, etc.). Each pulse can be independently programmable (e.g., frequency, amplitude, duration, etc.). The stimulation pulse(s) and/or train(s) may or may not generate a repeating pattern.

Each pulse may include a charge injection phase and a charge balance phase (i.e., each pulse may be biphasic). In some embodiments, the balance phase duration and amplitude is programmable as a ratio of the charge phase duration and amplitude so that zero net charge is maintained. The ratio of charge to balance, denominated as the Charge:Balance Ratio (C:B Ratio), is applied so that the product of amplitude and duration (charge) is equal in both the charge phase and the balance phase. In some embodiments, each pulse is programmable via the following parameters: ratio of charge phase duration to balance phase duration; pulse width range; stimulation amplitude (current level); and delay between the charge phase and the balance phase. Stimulation amplitude may be varied during the same phase (e.g., generating a gradually decreasing current for the charge pulse width). In some embodiments, zero net charge is preferred. In other embodiments, non-net-zero charges may be used. Charge densities greater than 30 µC/(cm phase) have been shown to cause nerve and tissue damage. Systems and methods described herein may include mechanisms to ensure a charge density limit is not exceeded.

Figure 3:
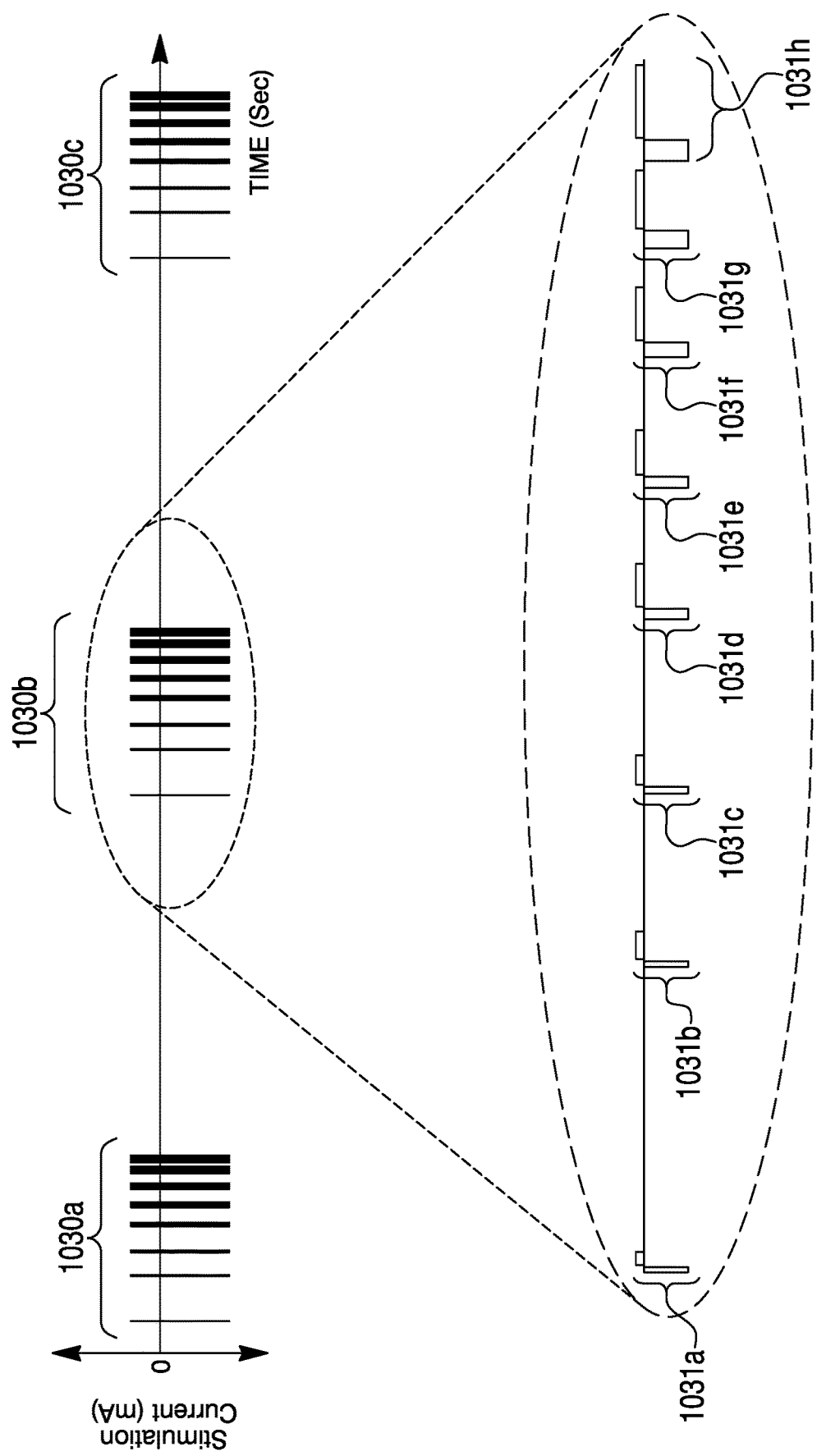
FIG. 3 is a graphical depiction of one or more exemplary stimulation trains including stimulation pulses, according to one or more embodiments.

FIG. 3 illustrates exemplary stimulation signals which may be delivered to the target nerve(s) or muscle(s). For example, referring to the diaphragm, a skeletal muscle, pacing may be accomplished by delivering one or more stimulation signals to a phrenic nerve to produce a mechanically effective contraction of the diaphragm. In that regard, the stimulation signals may include a plurality of pulses that are grouped in stimulation trains. As used herein, a stimulation train is defined as a collection of stimulation pulses. This definition does not imply a specific composition, order of delivery, and/or shape profile or envelope. FIG. 3 illustrates exemplary stimulation trains 1030a, 1030b, 1030c, including pulses 1031a-1031h, generated by the stimulator and delivered to the one or more lead(s) 1005 (e.g., energy sources 1006, electrodes, etc.) for stimulating the phrenic nerve(s). The stimulation trains 1030 may start with a doublet (pair of pulses 1031) or a triplet. In some embodiments, two or three pulses 1031 in quick succession at the beginning of recruitment may increase the overall force profile by shifting the baseline up during the initial onset of recruitment. Similarly, a doublet or triplet delivered partway through a train 1030 can cause a sustained force increase. The upward shift in early force production may correspond to fewer stimulation pulses 1031 being used to generate the same amount of force from the diaphragm in a comparable period of time. These profiles may be beneficial as over-activating a muscle, such as the diaphragm, with excessive stimulation may induce fatigue. Over stimulation of a muscle may also cause conversion of fibers from fast-twitch (powerful, but fatigued easily) to slow-twitch (fatigue-resistant but unable to produce large amounts of force).

Stimulation may be characterized by the rate, the duration, the pulse width, the frequency, and the amplitude of the signals. The stimulation rate may correspond to the number of stimulations trains 1030 delivered per minute. The stimulation rate may correlate with the patient's respiratory rate (e.g., a patient's innate respiratory rate) or mechanical ventilator rate. The duration of the stimulation train 1030 may refer to the length of time the stimulation train 1030 is delivered. The pulse width may indicate the duration of each individual pulse 1031 creating the stimulation train 1030. Similarly, the frequency may indicate the number of individual pulses 1031 delivered per second. Amplitude may refer to the voltage of each pulse 1031 delivered or an average voltage delivered per pulse 1031 of a stimulation train 1030. Without being limited by theory, it is believed the amplitude, frequency, and pulse width, may be factors determining the strength and other characteristics or parameters of the induced diaphragmatic pacing.

Figure 4:
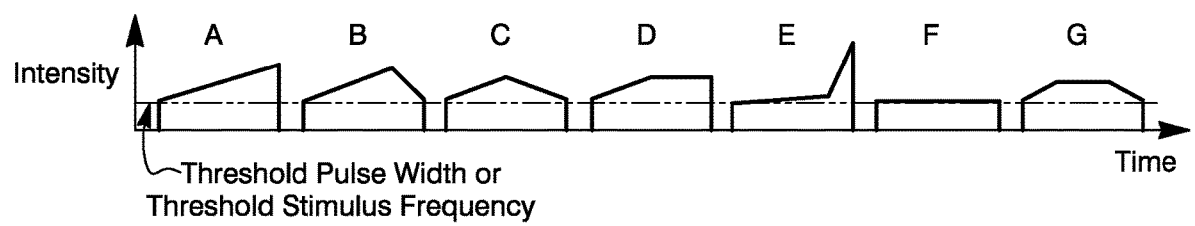
FIG. 4 illustrates examples of representative ramp envelopes where the ramp slopes represent the modulations in pulse width and/or pulse frequency within a train.

FIG. 4 illustrates examples of stimulation trains (e.g., ramp trains). In some embodiments, the stimulation trains form ramp trains. For example, ramp trains can be formed by linearly increasing (or decreasing) either the instantaneous frequency of consecutive pulses in a train, the durations (pulse widths) of consecutive pulses in a train, or both.

Ramp trains may indicate that a change in injected charge is induced by programmed stimulation parameters, user activation, or other applied modulation.

Figure 5:
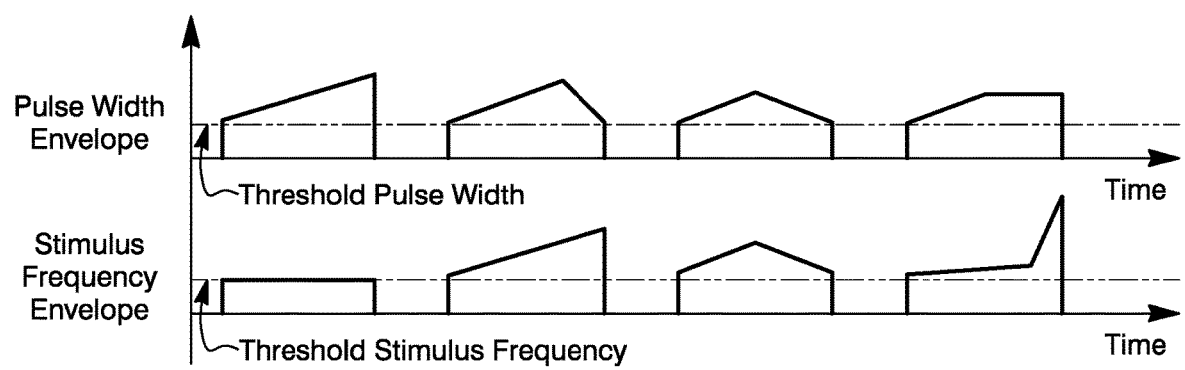
FIG. 5 illustrates examples of representative pulse width ramp envelopes and stimulus frequency envelopes, which can be combined together to form a single pacing ramp.

Variations in pulse width and frequency modulation allow different ramp train envelopes to be designed. Referring to FIGS. 4 and 5, ramp envelopes may be generated during a single pacing ramp in pulse width alone, frequency alone, or both in pulse width and frequency.

FIG. 5 shows examples where pulse width and stimulus frequency envelopes may be modulated together, or individually, during pacing to generate a desired ramp train. For example, still referring to FIG. 5, combination AF (leftmost) may cause a graded recruitment of the phrenic motoneurons at a constant frequency (no rate coding) and combination BA (second from the left) may gradually recruit and de-recruit the motoneurons, with a steadily increasing rate coding; although any combination is possible. It will also be possible to alter the rate of recruitment and de-recruitment (slope) of motoneurons, independent of the rate coding, by adjusting the relative percentage of pulse width increase and decrease duration within a single pacing ramp. Further, the present disclosure contemplates pulse width and frequency modulation defined mathematically as separate piecewise functions in time, thereby allowing any desired ramp envelope to be generated.

Although a large set of ramp trains may be generated, there will be some embodiments where a ramp train is configured to achieve one or more of the following: 1) mimic physiological contraction of the diaphragm by independently controlling recruitment and rate coding by means of pulse width and frequency modulation, respectively; 2) delay the onset of neuromuscular fatigue; 3) promote movement of fluid or other materials from or within the respiratory tract; 4) maintain or regain the native fiber composition of the healthy diaphragm; and/or 5) condition the diaphragm towards a specific fiber type (e.g., promoting growth of Type I, slow twitch, fatigue resistant fibers, etc.). Other exemplary stimulation profiles are described herein (e.g., those of FIG. 19) and may be used in combination with the portions of the stimulation profiles described in FIGS. 3-5.

Figure 6:
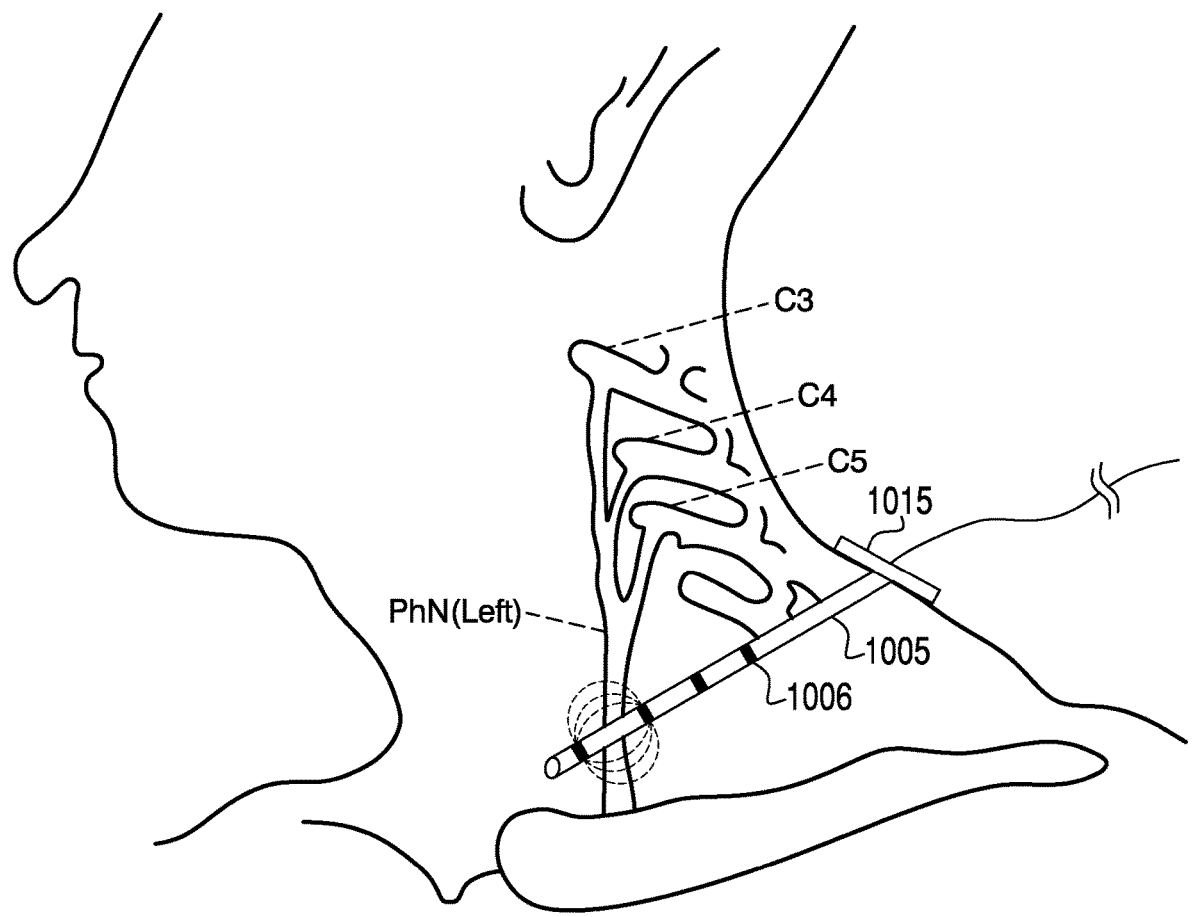
FIG. 6 illustrates the anatomy of selected tissues and nerves in a person's head, neck, and torso, along with an exemplary stimulation lead, according to one or more embodiments.

FIG. 6 shows some anatomical landmarks near the phrenic nerves. The phrenic nerve originates from cervical spinal roots C3, C4, and C5. Spinal root C4 provides the main contribution, with lesser contributions from C3 and C5 and some communicating fibers from the cervical plexus. The nerve arises at the lateral border of the anterior scalene muscle. It then passes inferiorly over the anterior surface of anterior scalene, deep to the prevertebral layer of cervical fascia. On both sides, the nerve runs posterior to the subclavian vein.

Still referring to FIG. 6, in one or more embodiments, a phrenic nerve stimulation device may stimulate the left PhN. Several energy sources 1006, which can also serve as sensors, may be distributed along a lead 1005 in an arrayed configuration. Energy emission may be focused in one axial direction from the array, or may radiate uniformly in multiple directions. The nerve stimulation device may be secured to the patient to mitigate or reduce the degree of movement of the stimulation array over time. Suitable fixation or anchoring mechanisms 1015 may include an adhesive patch or suture. The fixing or anchoring mechanism 1015 may also help in the orientation of the lead 1005 such that the energy sources are focused towards the target nerve(s) or muscle(s).

FIG. 7 shows a medical system 1000 including two percutaneous leads 1005, each with multiple energy sources 1006. One lead 1005 is placed near the left phrenic nerve, and the other lead 1005 is placed near the right phrenic nerve. Percutaneous leads 1005 may also be positioned to stimulate the vagus nerves, both phrenic nerve(s) and vagus nerve(s), or other nerves, as desired. The energy sources 1006 are electrically connected to a can 1025 which may contain logic circuits, a battery or other energy storage device, and/or other electronics. The can 1025 may be implanted in the patient. The electronics and the energy storage device may also be embedded into a skin patch which may be affixed to the patient's skin. The patch and/or can 1025 may interact with the programming unit, control system, control unit 1001, or other system, through wired or wireless connection.

Figure 8:
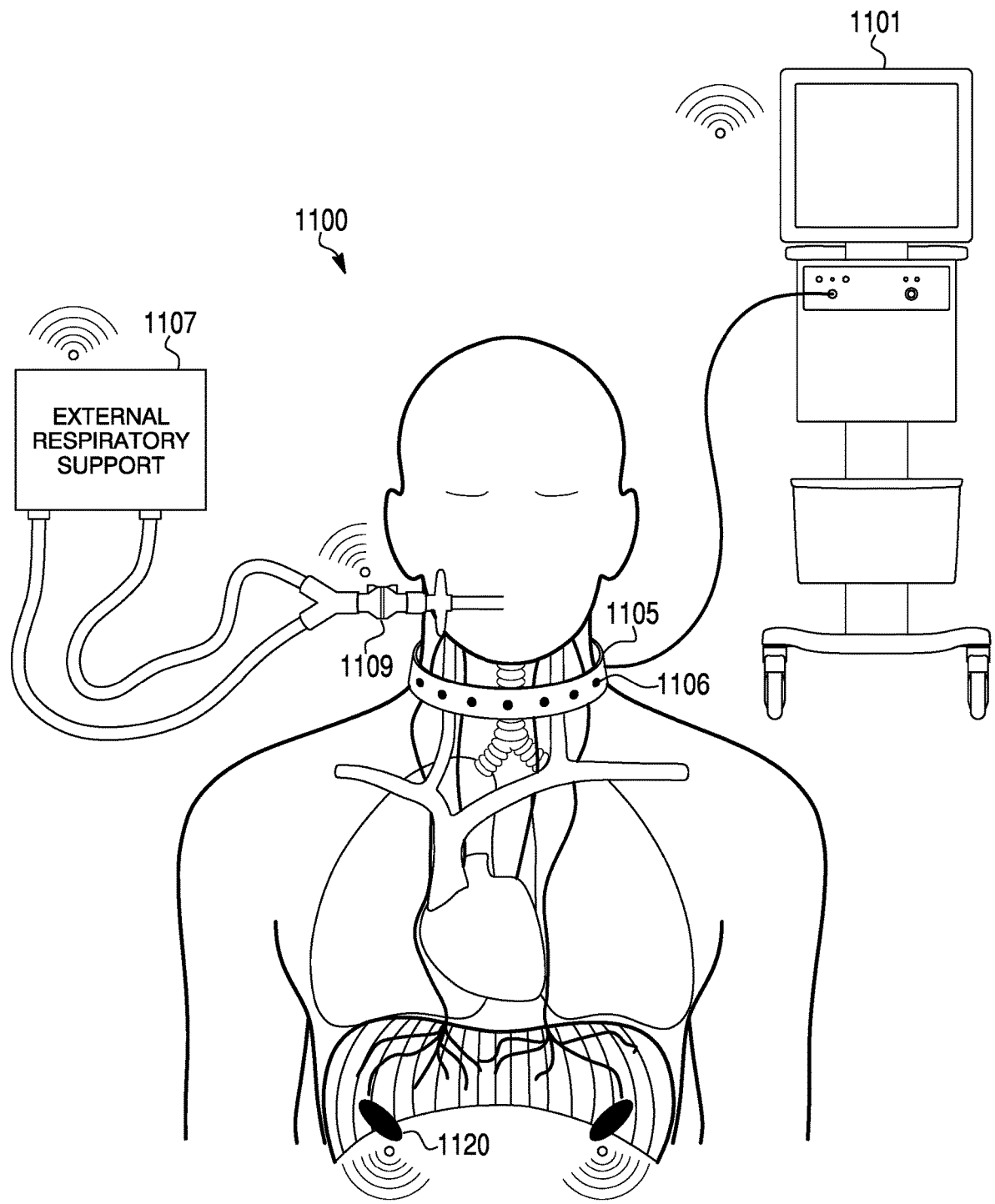

FIG. 8 shows a medical system 1100 including a neck collar 1105 with multiple energy sources 1106. The collar can be connected to the control unit 1101 wired or wireless. The neck stimulation device (neck collar 1105) can activate phrenic, vagus, or other nerves in the vicinity. A control unit 1101 may comprise a computer on a cart (e.g., including a touch screen or other graphical user interface). The control unit 1101 may communicate with various components of the system (e.g., wirelessly). Similar to other systems described herein, system 1100 may optionally include external respiratory support 1107 and/or a breath sensor 1109 or other sensor.

Sensors 1120 on the left and right torso of the patient can send physiological information to the control unit 1101. In some embodiments, motion sensors on the diaphragm can provide information related to diaphragm contraction/movement. Similar sensors may be used to detect contraction or movement of other muscles (e.g., the intercostals). In some embodiments, a sensor 1120 may deliver energy, causing activation of one or more respiratory muscles. In some embodiments, as described below, impedance sensors may help detect the distribution of gas in the patient's various lung regions and/or sense the condition of tissue in the body.

EIT may be used to monitor lung function. Lung tissue impedance may be up to approximately five times higher than most other soft tissues in the torso region. The impedance differential results in high contrast of the lungs. In addition, lung resistivity may increase and decrease severalfold during a breath (e.g., the time period between inspiration and expiration). Impedance measurements may help characterize and distinguish between lung conditions which result from regions with lower resistivity (e.g., hemothorax, pleural effusion, atelectasis, lung edema, etc.) and those with higher resistivity (e.g., pneumothorax, emphysema, etc.).

Electrical impedance of lung tissue may change as a function of air content over time. For example, the electrical impedance of the thorax changes during inhalation and exhalation. The thorax presents an electrical impedance that includes two components: a relatively constant value and a varying value. Changes in impedance may result from one or both of the following two effects during inspiration: 1) an increase in the gas volume of the chest, relative to the fluid volume, which may cause a decrease in conductivity, and 2) an increase in the length of the conductance path (e.g., between two electrodes) when the lungs expand. These effects may cause impedance to increase during inspiration. There is an approximately linear correlation between the impedance changes and the volume of air during a respiratory cycle. The varying component of impedance (e.g. respiration impedance) generates a varying voltage component when current is injected (e.g. by electrodes). This varying voltage component may be used to determine a subject's breathing rate.

Impedance information may be used to characterize the dynamic respiratory condition of a patient, such as, for example, the air distribution in various lung regions. The air distribution in various lung regions may be used to determine a need to maintain or adjust the parameters of a device or system described herein (e.g., respiratory muscle activator (RMA) parameters), such as, for example, stimulation energy, stimulation pulse amplitude, stimulation pulse width, stimulation pulse frequency, stimulation duration, stimulation rate, and/or the interval between stimulations/pulse trains.

One or more embodiments are designed to utilize real time monitoring of EIT to measure the changes in the distribution of lung volumes between left and right, anterior and posterior, lung regions. Further methods and systems described herein may compare the lung gas distribution against a targeted more optimal distribution, assess the need to adjust the air distribution towards a more optimal gas distribution, to determine the appropriate stimulation energy profile for the respiratory muscle activator (RMA) to achieve the desired lung gas distribution during the phases of breathing, and/or deliver the desired stimulation energy profile to the respiratory muscle (and/or associated nerves) in order to maintain or improve ideal air distribution. In some embodiments, the system may include external respiratory support (ERS) (e.g., CPAP, mechanical ventilator, high flow oxygen, ECMO, ECCO, etc.) and the settings of the ERS and the RMA may be adjusted to ensure appropriate gas exchange and mitigate the likelihood of patient injury (e.g., VILI, barotrauma, low tidal volume, high tidal volume, etc.). One or more sensors (e.g., heart rate, $CO_2$, $O_2$, breathing, temperature, motion, electromyography, electrocardiography, airflow, pressure, etc.) may also be used to assist in determining suitable ERS and RMA settings.

As described previously, impedance information may be used to characterize the respiratory condition of a patient, such as the air distribution in various lung regions, and thereby determine the need to maintain or adjust respiratory muscle activator (RMA) parameters (e.g., energy, stimulation pulse amplitude, stimulation pulse width, stimulation pulse frequency, stimulation duration, the interval between stimulations/pulse trains (e.g., stimulated breath rate), etc.).

As described above, lung gas distribution devices described herein may include a belt comprising impedance sensing electrodes. The impedance sensing electrodes, when placed in various locations on the torso of a patient, may determine the distribution of gas in various regions of a patient's lungs.

Tissue impedance sensing (TIS) is a type of tissue characterization in which the electrical conductivity, permittivity, and/or impedance of part of a body is inferred from electrode measurements which can be used to form a tomographic image or multi-dimensional analysis of tissue condition or composition. Electrical conductivity varies considerably between various biological tissues and as a function of the movement of fluids and gases within tissues. TIS systems can apply small alternating currents at a single frequency, or alternatively TIS systems can use multiple frequencies to better differentiate between tissue types.

Figure 9A:
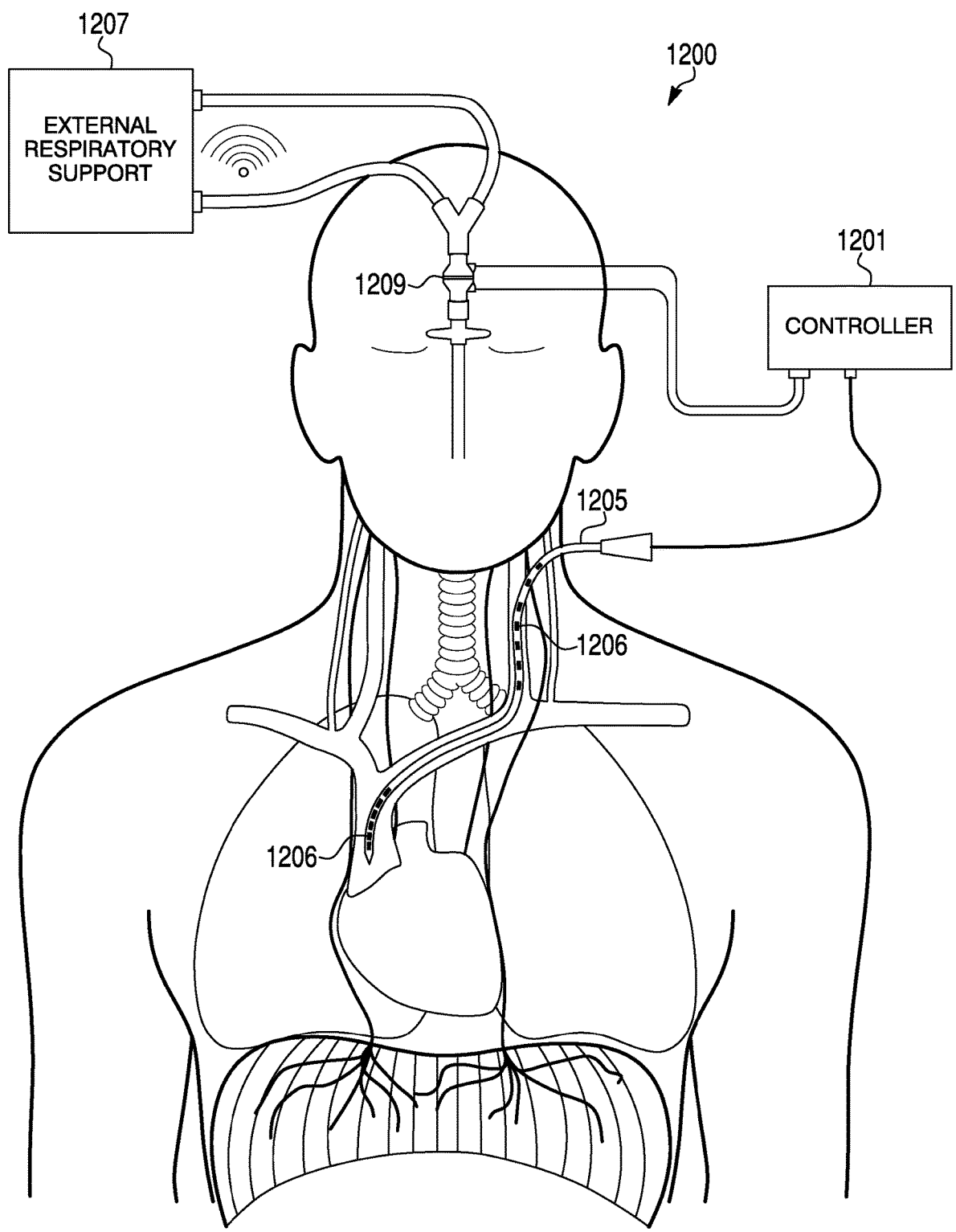
Figure 9B:
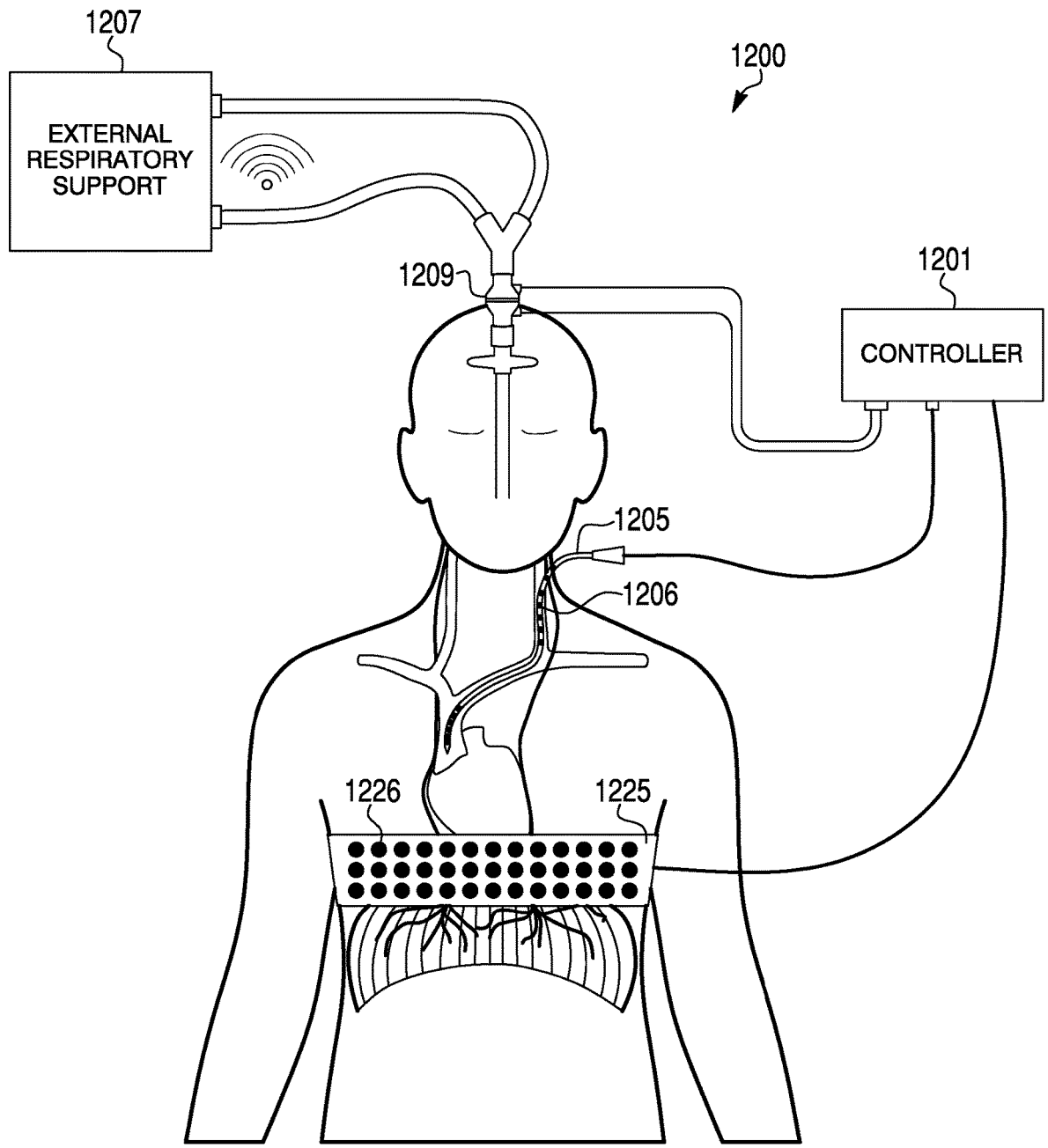

FIGS. 9A and 9B show exemplary systems 1200 including a respiratory muscle stimulation lead 1205, an external respiratory support device 1207, a breath sensor 1209, a lung gas distribution sensor (e.g., one or more electrodes or other energy sources 1206, such as, for example, internal sensors, external sensors, electrode array 1225, etc.), and a control unit 1201. The control unit 1201 may be configured to adjust the parameters of the stimulation and external respiratory support device 1207 to improve/maintain an optimal gas balance in various regions of the patient's lungs during one or more respiratory cycles.

In some embodiments, the respiratory muscle stimulation lead 1205 may include a lead body or cannula which passes through the skin of the patient into a blood vessel. The cannula may include one or more energy sources 1206 and/or sensors (e.g., electrodes). As shown in FIGS. 9A and 9B, at least one energy source 1206 may be positioned either on the skin or below skin of the patient. Further, one or more energy sources 1206 may be positioned to stimulate the left vagus nerve, one or more energy sources 1206 may be positioned in a blood vessel, one or more energy sources 1206 may be positioned to stimulate the left phrenic nerve, one or more energy sources 1206 may be positioned within a blood vessel to transvenously stimulate a nerve, and/or one or more energy sources 1206 may be positioned to stimulate the right phrenic nerve. The energy sources 1206 may be located on the skin, within the tissue, within a blood vessel, or any other location suitable for nerve and/or muscle activation.

In some embodiments, conducting surface electrodes 1226 and/or one or more other sensors (e.g., an impedance sensor) may be attached to the skin around the patient's torso. Alternatively, or in addition, internal electrodes may be used to assess impedance. Referring to FIGS. 9A and 9B, electrodes 1226 on the belt 1225, electrodes 1206 on the cannula/needle/catheter, or both may be used to assess tissue impedance and/or stimulate respiratory muscles.

Referring to FIG. 9B, one or more electrodes 1226 may be attached perpendicular to the midaxillary line at approximately the level of the sixth rib on either the front, the back, the sides of the patients, or any combination thereof. If desired, one or more electrodes 1226 may be placed at reference locations such as immediately below the clavicle or at the sternal notch, below the ribcage, and/or at the level of the xiphoid process at the midaxillary line. In other configurations, electrodes 1226 may be placed higher or lower on the patient to facilitate impedance detection and/or muscle stimulation. In some embodiments, one or more electrodes 1226 may be placed in other locations and configurations depending on the patient and other physiological conditions (e.g., presence of implants, such as a cardiac pacemaker, etc.).

One or more impedance electrodes 1226 may be positioned on one or more leads 1205 which may be readily affixed to, and easily removed, from the patient. For example, two or more electrodes 1226 may be arranged in a linear array, grid-like pattern, and/or in a configuration designed to conform to a patient's anatomy. In some embodiments, four or more electrodes 1226 are arranged in a linear array and/or grid-like array.

In some embodiments, multiple electrodes 1226 are arranged as a belt 1225, vest, and/or array. Preferably, one or more electrodes 1226, electrode leads, and/or sensors may be placed around the patient's torso, on the thorax, or on the abdomen of the subject. Systems and methods described herein may utilize single-use electrodes or multi-use electrodes. The impedance array may come configured with attachment means (e.g. tape, glue, elastic strap, adjustable belt 1225, or other affixing member, etc.) to secure the electrodes or array to the patient. The array may also incorporate soft cloth, foam, non-silicone materials, etc., to reduce the likelihood for skin irritation.

Different size electrodes and configurations can be utilized for different sized patients (e.g., adults, pediatrics, neonates, high BMI, low BMI, etc.). In some embodiments, the electrodes may have a surface area of approximately 2 mm² to approximately 6 mm².

In some embodiments, impedance electrodes may be enabled to both deliver electrical impulses to the body and sense impedance. In other embodiments, some of the electrodes may only delivery electrical impulse, and some electrodes may only sense impedance. In some embodiments, impedance electrodes may be used for sensing physiological information from a patient, such as nerve activity, ECG, temperature, or motion, as described herein. When being used for sensing, one or more of electrodes may be electronically coupled to a signal acquisition module. The signal acquisition module may receive signals from electrodes.

Electrodes and/or other sensors described herein may be electrically connected to a remote control unit 1201 (e.g., via a wired or wireless connection) and may be configured to transmit data to a remote sensor or control center/device/system/controller. Electrodes and sensors may include local power sources such as, for example, button-cell batteries. Electrodes and sensors may be electrically connected to an external or remote power source.

One or more impedance sensors may be configured to gather data over time. Signals may be recorded over several breaths (e.g., over a fixed time interval, such as, 15 seconds, 30 seconds, or other duration). Sensing may occur continuously or intermittently. Sensing may occur at pre-determined and variably selected intervals (e.g., for up to at least 5, 10, 20, or 50 of the patient's breaths, for up to at least 200 of the patient's breaths, for up to at least 2000 of the patient's breaths, or for another duration).

As previously mentioned, impedance electrodes may be positioned within the patient's body. As an example, electrodes may be located on a percutaneous lead body. As another example, electrodes may be positioned on a transvascular device such as a catheter, described herein and in the patents and publications incorporated by reference. Impedance may be measured between any two electrodes of the lead body (e.g., catheter), between catheter electrodes and skin electrodes, or both. In some embodiments, impedance may be measured between: a) either a proximal-most electrode or hub, and b) a distal electrode on the catheter.

The impedance presented to injected current (e.g., current transmitted from one or more electrodes) may be dependent on the conductivity of the fluid surrounding the electrode(s), or adjacent tissue, in the local area between a pair of sensing electrodes. The conductivity may also depend on the cross-sectional area of the blood vessel at the site of the electrode(s). The impedance of an electrode may vary depending on the medium in which it is resting. For example, an electrode placed in a relatively large body of conductive fluid may have a lower impedance than one resting against a vessel wall.

Signal filtering, processing, and analytical techniques described herein and known in the art may be used to assess impedance measurements in real time. Changes in impedance profiles, other physiological information, and/or warnings or alerts, may be displayed to a health professional, subject, or other user, on a graphical user interface.

A variety of sensors may be used to coordinate stimulation with a patient's breathing, coordinate stimulation with the delivery of a breath from the mechanical ventilator, or both. Sensors may detect heart rate, $CO_2$, $O_2$, breathing, temperature, motion, impedance, electromyography, electrocardiography, airflow, pressure, or any combination thereof.

Respiratory therapy systems 1200 described herein (e.g., those shown in FIGS. 9A and 9B) may be used to manage the flow of gas into and/or out of a patient's lungs. The system may comprise a control unit 1201 for managing the performance of the respiratory therapy system. The system may further comprise at least one energy emitter 1206 (e.g., stimulation array, electrode lead, stimulation catheter, etc.) for delivering energy to cause contraction of a respiratory muscle, wherein the energy emitter is functionally connected to the control unit 1201 (e.g., direct wire or wireless, etc.). As an example, a stimulation array may be positioned either internal to the patient, external to the patient, and/or may incorporate a combination of both internal and external components. The stimulation array may include catheters, cannulas, needles, lead bodies, transcutaneous emitters (e.g., TENS, etc.) or other devices described herein or known in the art.

The system may include one or more impedance sensors 1226 for acquiring a bioelectrical impedance signal from the patient, wherein the impedance sensors 1226 are functionally connected to the control unit 1201. As described herein, the impedance sensors 1226 can be located either inside the subject, outside the subject, or both.

The controller or control unit 1201 receives a bioelectrical impedance signal; analyzes the bioelectrical impedance signal to determine an approximate air distribution between lung regions (e.g., posterior, anterior, left, right, upper, lower, etc.) versus a desirable air distribution in the regions of the lungs (for example in the posterior and anterior regions on each the left and right side), and further whereby stimulation parameters are adjusted such that energy delivered by the stimulation array may cause the air distribution in the lungs to change.

The stimulation array may comprise an array configured to stimulate a respiratory muscle on the right side of the patient and an array configured to stimulate a respiratory muscle on the left side of the patient. The stimulation levels can be independently adjusted to balance the volume of air in the different regions of the patient's lungs. For example, increasing the stimulation energy directed to the right diaphragm muscle may help shift the air or gas distribution from an upper lung region to a lower lung region. This may allow ventilation of the patient at similar tidal volumes but with lower pressure in the upper/anterior lung lobes, thereby mitigating atelectasis in the lower/posterior right lung and/or reducing the potential for barotrauma in the upper right lung. In some embodiments, the reduction in upper lung pressure may reduce signaling from pulmonary stretch receptors and thereby also reduce VIBI.

Systems described herein may be operated in Autonomous Mode, or A-Mode. A-Mode is a life-sustaining mode that can operate independently of external respiratory support. In some embodiments, such as those depicted in FIGS. 2 and 7-9B, a routine may be executed by the system for carrying out one or more functions, including the Autonomous Mode. In that regard, the A-Mode operates in closed-loop control fashion using feedback from various sensors, such as one or more of the sensors (e.g., sensors 1020 and/or impedance electrodes 1226). These sensors may be used to monitor physiological variables that can include, but are not limited to: central venous pressure, mixed venous oxygen saturation, heart rate, and movement activity levels. A-Mode may provide adjustable diaphragmatic pacing to a patient retaining none, some, or all of the inherent spontaneous breathing ability and requiring assisted breathing. Systems may automatically adjust to the patient's physiological needs and changed activity levels, as needed.

In some embodiments, a system operating in A-mode may be interfaced with a backup external respiratory support 1007. For example, A-Mode may be applicable to patients who are permanently dependent on mechanical ventilators or otherwise in need of continuous pacing from the system.

In some embodiments, in contrast to some systems for carrying out Pacer-Initiated Ventilation Mode and Ventilator-Initiated Pacing Mode, the system carrying out the A-Mode may be totally implanted under the skin of the patient in the upper chest area. As described previously, the system may be powered by a power storage source, such as either primary or rechargeable, implantable batteries, and may be integrated with other implantable devices that support heart or other functions to a patient. Continuous data collection may be used to create near real-time images/video of the desired tissue and monitor lung function.

Small alternating currents may be applied via some or all of the electrodes, and resulting electrical potentials may be recorded from one or more other electrodes. The free ion content of a tissue or bodily fluid determines the conductivity of the tissue or fluid. For example, muscle and blood will conduct the applied currents with less impedance than, for example, fat, bone, or lung tissue. The variance in impedance may be used to reconstruct a characterization of the targeted tissue, such as, for example, by creating static image. The process may be repeated with numerous different electrode configurations to generate a characterization of the studied tissue. As one example, the characterizing data may be used to construct a multi-dimensional tomogram via image reconstruction algorithms (known as electrical impedance tomography/scanning, or EIT/EIS).

In one embodiment, the impedance electrodes may be configured to also serve as stimulators and be used to stimulate intercostal muscles to help with expiration, and, for example, in combination with an inspiratory stimulator array (e.g., needle or catheter stimulation of phrenic nerve/nerves), be used to manage portions of both inspiration and expiration for the patient.

Systems herein may further comprise an external respiratory support device, such as a positive pressure respiratory device for moving gas into the lungs of the patient. In such embodiments, the respiratory therapy system may detect the action of the positive pressure respiratory device with a sensor, or may be functionally connected with the positive pressure respiratory device. The controller may optimize the delivery of positive pressure from the positive pressure respiratory device and/or the stimulation energy from the respiratory muscle stimulator to balance the gas level and flow in the various regions of the patient's lungs during a respiratory cycle.

FIGS. 10A-10H show exemplary delivery devices, sheaths, cannulas, needles, flexible stimulation lead structures, energy sources, and anchoring mechanisms. Other cannula/needle/catheter designs may be implemented, such as those described in the U.S. patents and publications incorporated by reference. In examples, the lead 1005 initially could be embedded into a needle (e.g., comprising stainless steel, polymer, etc.) or an introducer sheath, as shown in FIGS. 10A-10D. The delivery device for placing the stimulation array (e.g., an array including energy sources 1006) may include an elongated cannula/needle/catheter 1050.

The cannula/needle/catheter 1050 may have a relatively smooth outer surface, small cross-sectional area, and a distal tip suitable for passage through skin and tissue, as compared to conventional cannulas. One or more embodiments including a cannula/needle/catheter 1050 may include a channel or lumen, defined by the body of the cannula/needle/catheter 1050, suitable for receipt of a guidewire, stylet, and/or stimulation lead 1005.

Figure 10A:
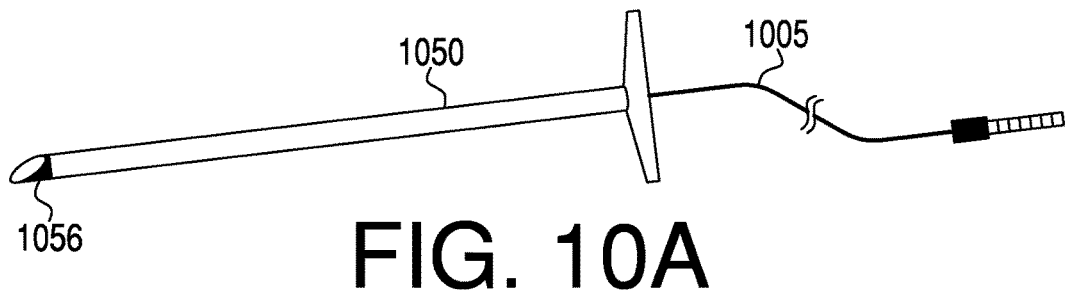
FIGS. 10A-10D illustrate perspective views of exemplary stimulation leads and delivery systems, according to some embodiments.
Figure 10B:
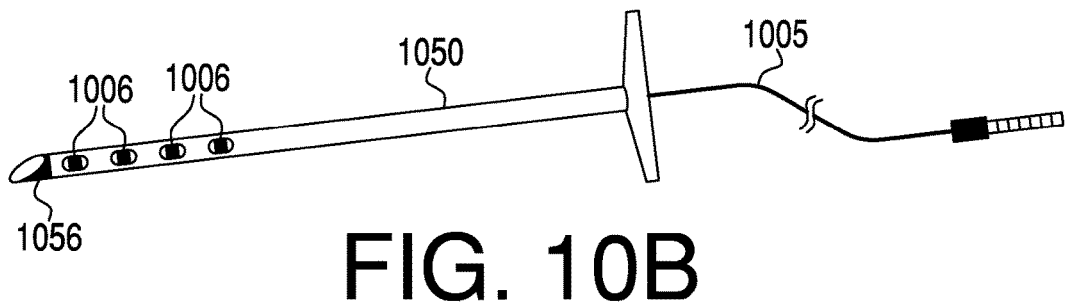

The cannula/needle/catheter 1050 may be electrically conductive and may be placed to allow for localized nerve stimulation. The cannula/needle/catheter 1050 may be rigid, flexible, or controllably flexible to help steer the stimulation lead 1005 to the desired site. As shown in FIGS. 10A and 10B, the cannula/needle/catheter 1050 may have an energy emitter 1056 (e.g., located at the distal tip) configured to assist with placement of the stimulation array. In this example, the cannula/needle/catheter 1050 may be connected to the stimulator and/or control unit to provide a signal directly to the distal tip energy emitter 1056, or other portion, of the cannula/needle/catheter 1050 (e.g., to aid in navigating the distal tip toward the desired location). In some embodiments, energy emitter 1056 may be mounted on the outer surface of the cannula/needle/catheter 1050 so that the at least one electrode (e.g., energy source 1006) may be advanced to close proximity of the target nerve (e.g., phrenic, vagus, etc.) for stimulation. A second electrode (not pictured) may be connected to the patient's skin to create a return path for the electrical stimulus.

The cannula/needle/catheter 1050 or lead 1005 may include a stylet or obturator that can be inserted through a passage to provide a desired level of rigidity to the cannula/needle/catheter 1050 or lead 1005. Upon removal, this passage, or another, may be used for fluid/drug delivery or for other purposes. Different shape stylets may be used (bent and/or beveled tips for example) to improve steerability during positioning of the cannula/needle/catheter 1050 or lead 1005. Once the stylet is removed, the lumen may be used for inserting the stimulation array into the patient.

In some embodiments, an elongated cannula/needle/catheter 1050 is linear, non-linear, flexible and suitable for being steered toward the target nerve, or a combination thereof. The cannula/needle/catheter 1050 may include visualization means such as ultrasound capability to allow optimal positioning of the stimulation electrode(s), such as, for example, energy sources 1006. In some cases, the cannula/needle/catheter 1050 is used to deliver an electrode array to the desired position after which the cannula/needle/catheter 1050 may be removed from the body. For example, a split or peel-away cannula may be employed.

In some embodiments, the stimulation array (e.g., an array including one or more leads 1005 and/or energy sources 1006) may be suitable for being steered toward the target nerve (e.g., flexible). The leads 1005 and/or energy sources 1006 for stimulation may be folded, curled, twisted, coiled, and/or wrapped to easily fit within a lumen or channel in the elongated cannula/needle/catheter 1050, where it may then be advanced and deployed to the desired location, at which time the energy sources 1006 and/or leads 1005 may recover to an alternate geometrical configuration. In some embodiments, the array may comprise a plurality of electrodes (e.g., energy sources 1006) positioned around a shaft. For example, a flexible circuit may be wrapped so that discrete energy sources 1006 will direct their energy in specific directions emanating radially in a field of excitation from the cannula/needle/catheter 1050. The cannula/needle/catheter 1050 may include an extruded polymer tube (e.g. catheter) or metal needle. The flexible cannula/needle/catheter 1050 may include orientation indicators on the external portion of the cannula/needle/catheter 1050 to provide a clinician with an indication of orientation. The cannula/needle/catheter 1050 may be oriented (longitudinal, axial, etc.) to achieve the desired location for optimal stimulation. Securement means as described herein help lock the stimulation array in position. The securement device may comprise an adjustment mechanism to make micro adjustments to the location of the stimulation array, providing small, potentially incremental, advancement or withdrawal of the array.

In one or more embodiments, the stimulation array may be delivered through a delivery cannula/needle/catheter 1050, which can consist of a needle or other guiding tool for placing the array. The delivery cannula/needle/catheter 1050 and/or stimulation array may contain markers (e.g., radiopaque markers) that are visible via ultrasound, x-ray, or other means to assist with placement. After placement of the array, other external markers may be placed upon the patient's skin, for example, by means of a temporary bandage, to provide future reference for the location of the stimulation array.

Identification and/or location of the phrenic nerve may be performed using anatomical landmarks, ultrasound, and/or 3D images generated from a CT scan or MRI. The insertion of a cannula/needle/catheter 1050, energy sources 1006, and/or leads 1005, may be at the level of the cricoid cartilage and lateral of border of the sternocleidomastoid muscle (SCM) approximately at the level of the C5 vertebra. The patient may be first assessed to determine suitability for stimulation lead 1005 insertion. Ultrasound or other imaging techniques may be used to determine if patient anatomy is suitable for insertion of a stimulation electrode and/or lead 1005. Anatomical landmarks (bones/veins using ultrasound, external landmarks, etc.) may be assessed and used to place the lead 1005. Once the insertion site is determined, the area around it may be cleaned and sterilized.

Typically, the skin of the subject may be prepared and/or cleaned for sterile device placement. A sterile drape may be applied. A local anesthetic may be administered. In some instances, the skin may be nicked or otherwise opened with a scalpel or blade to ease the insertion of the stimulation array and/or the delivery system (e.g., a system including cannula/needle/catheter 1050). Fluoroscopic, ultrasound, or other navigation means may be used to guide the placement of the cannula/needle/catheter 1050 and/or stimulation array. A surgical dressing may be placed over the insertion site. Antibiotics or other means may be used to mitigate the risk of infection at the skin access site.

In one embodiment, a cannula/needle/catheter 1050 is inserted through the skin, typically at an angle of 45 degrees or less and advanced parallel to the muscle fibers of the anterior scalene muscle (ASM), and under the sternocleidomastoid muscle (SCM) with the tip of the cannula/needle/catheter 1050 in the vicinity of the target nerve (e.g., phrenic nerve, vagus nerve, etc.), and more ideally with the tip of the cannula/needle/catheter 1050 advanced to a location past the target nerve such that when the stimulation array is deployed, at least one or more energy sources 1006 (e.g., electrodes) on the array may be in close proximity to the target nerve. Stimulation energy may then be delivered into the tissue adjacent the delivery device (e.g., cannula/needle/catheter 1050), during the placement of the delivery device, to help position the cannula/needle/catheter 1050 at the desired location with respect to the stimulation target (e.g., diaphragm, phrenic nerve, vagus nerve, etc.).

In one embodiment, such as the one shown in FIGS. 10A and 10B, the cannula/needle/catheter 1050 may include a separate stimulation array of one or more energy sources (e.g., distal tip energy emitter 1056). Once the cannula/needle/catheter 1050 s positioned and the diaphragm or other targeted nerve or muscle has responded to stimulation, a multi-electrode lead can be advanced through the cannula/needle/catheter 1050 (e.g., as shown in FIG. 10C-10D).

Figure 10C:
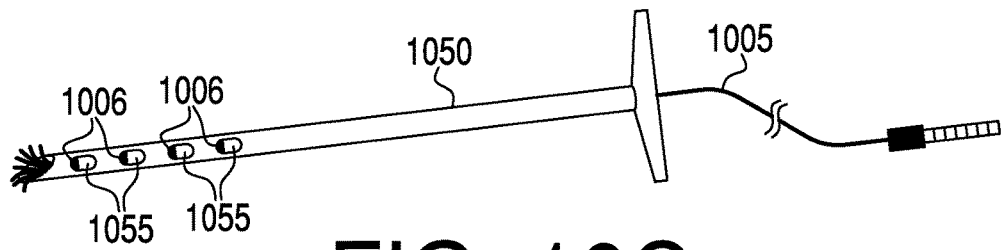
Figure 10D:
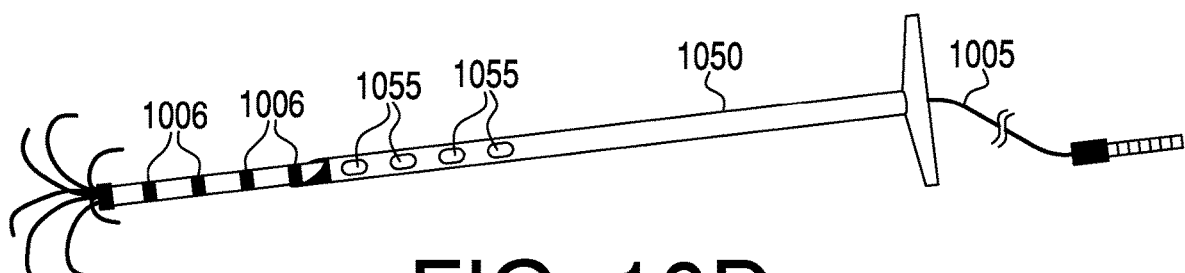

In some embodiments, the cannula/needle/catheter 1050 may include windows, openings, and/or apertures 1055, that align with energy sources 1006 of the stimulation array (as shown in FIGS. 10B-10D). The cannula/needle/catheter 1050 and/or the stimulation array may have an alignment feature (e.g., markings, mating connector, etc.) such that one or more electrodes are at least partially visible through one or more apertures 1055 when the stimulation array is suitably positioned within the cannula/needle/catheter 1050. As the cannula/needle/catheter 1050 is advanced into tissue, certain energy sources 1006 (e.g., electrodes) on the stimulation array may be activated, causing an electric field to penetrate the surrounding tissue. A respiratory muscle's response (e.g., diaphragm twitch or contraction) to the stimulation may be detected manually, visualized on external monitors such as a respiratory monitor, and/or measured through different types of sensors described herein.

The distal tip of the stimulation lead 1005 may have expandable features to anchor the lead 1005 in place, as shown in FIGS. 10C-10I. Anchoring features may include barbs, expandable portions, shape changing portions, expandable nitinol component, tines, inflatable balloon, shape deformation, mechanical system of flexible tines, mechanical system whereby tines are deployed upon removal of the stylet, and/or other anchoring features known in the art or described herein. Other anchoring features may be applied external to the patient such as, for example, sutures, adhesives, dressings, and other devices known in the art. Embodiments including anchoring features are shown in, for example, FIGS. 10C-10H.

In some embodiments, once the cannula/needle/catheter 1050 is in the desirable location, the cannula/needle/catheter 1050 may be withdrawn slightly to expose one or more anchoring features on the stimulation lead 1005. The stimulation lead 1005 may then be anchored in place. In other embodiments, the anchor features may be activated to extend past the cannula/needle/catheter 1050 to secure the stimulation lead 1005 after which the cannula/needle/catheter 1050 may be withdrawn.

Figure 10E:
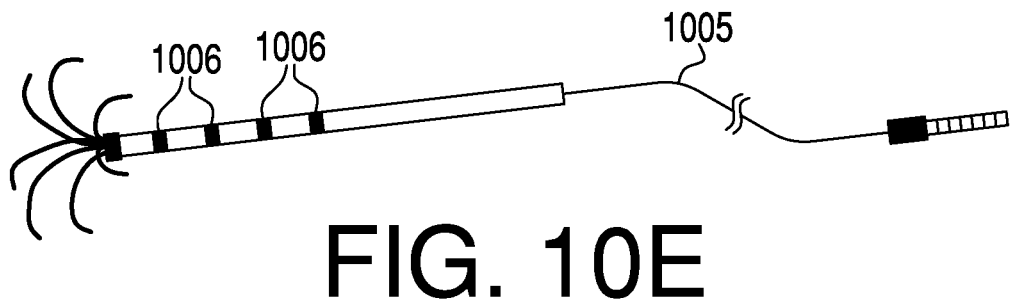
FIGS. 10E-10H illustrate perspective views of exemplary stimulation leads, according to some embodiments.
Figure 10F:
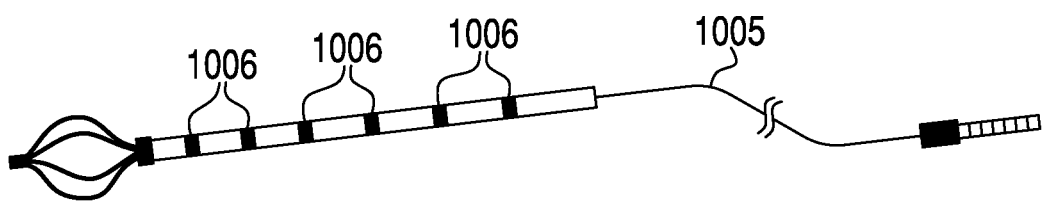
Figure 10G:
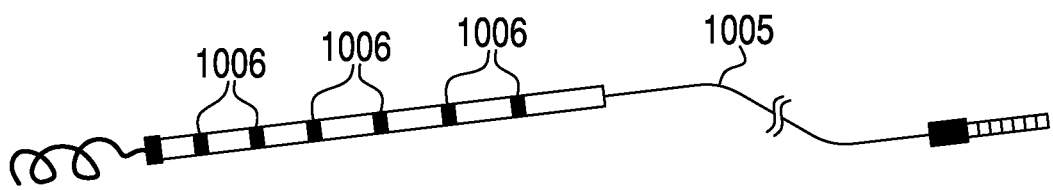
Figure 10H:
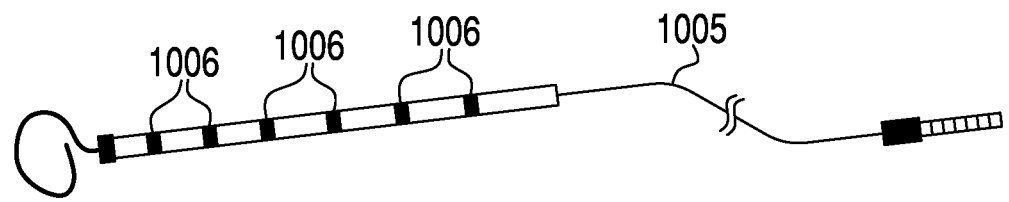

The position of the multi-electrode lead 1005 can be confirmed (e.g., by ultrasound, etc.). Once the lead 1005 is in a suitable position, the cannula/needle/catheter 1050 may be carefully removed from the patient as shown in FIGS. 10D and 10E. The cannula/needle/catheter 1050 may be split or slotted. In some cases, the cannula/needle/catheter 1050 may contain snap wings which are bent or manipulated to split or otherwise create a longitudinal channel in the cannula/needle/catheter 1050. As such, the cannula/needle/catheter 1050 may be split open to create a pathway by which it can be removed from the lead 1005 or stimulation array. In other embodiments, the cannula/needle/catheter 1050 may be removable over the distal end of the stimulation lead 1005.

Referring to FIGS. 10C-10E, in some embodiments, stimulation lead 1005 may include a plurality of expandable legs. The legs may be biased to expand while disposed within a lumen of the delivery device, and will extend outward once the legs are advanced sufficiently past a distal end of the cannula/needle/catheter 1050. There may be any suitable number of expandable legs, and the legs may be made out of any biocompatible material, such as, for example, plastics and/or shape-retaining metal alloys. The tips of the legs may be configured to attach to tissue, such as for example, tissue proximate one or more stimulation targets.

Figure 11:
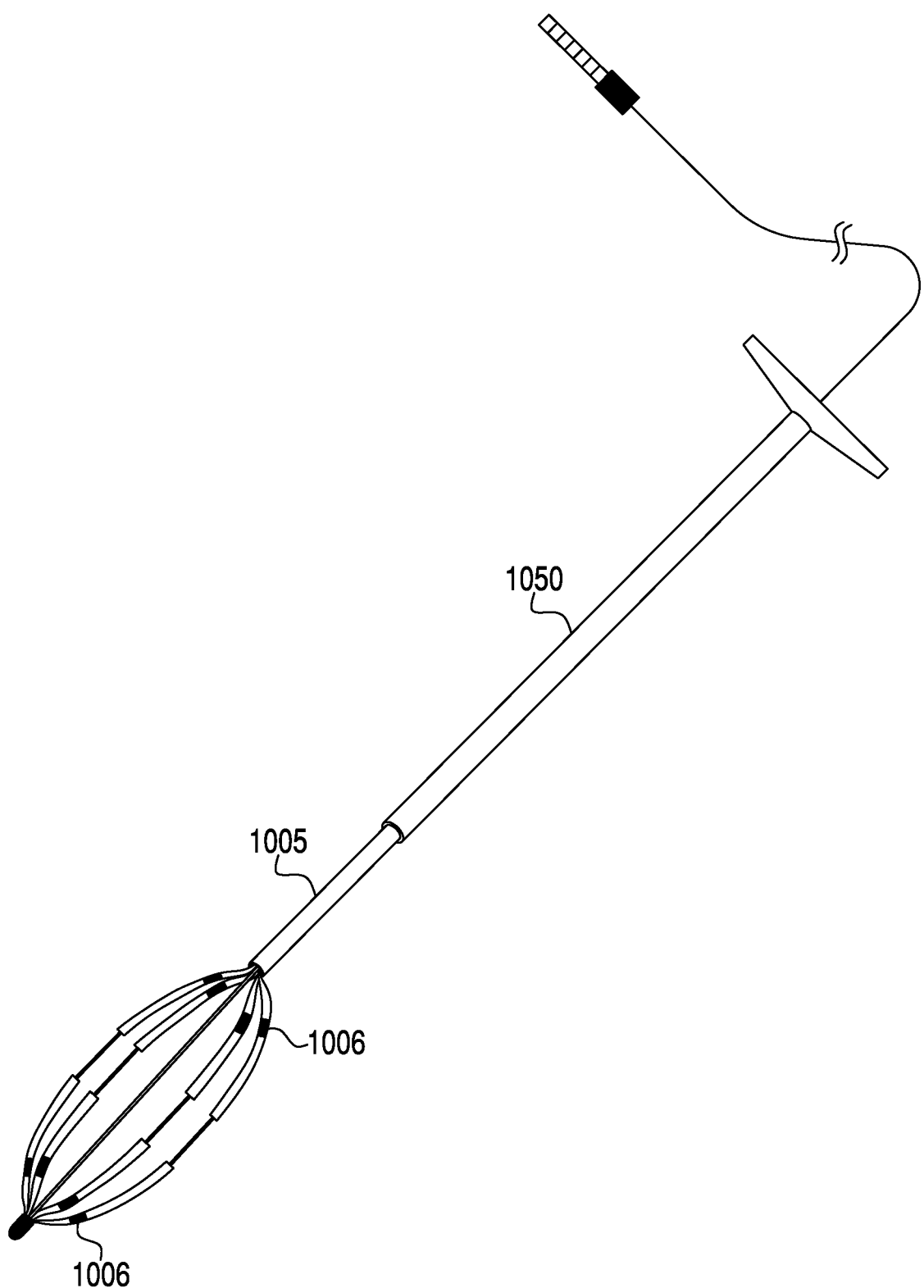
FIG. 11 illustrates a perspective view of an exemplary stimulation lead including an expandable member, according to one or more embodiments.

FIG. 11 shows a lead 1005 with expandable arms to form a basket. Each arm may have multiple energy sources 1006. In some embodiments, the basket may be in a collapsed state while disposed in cannula/needle/catheter 1050, and may be biased to expand, transitioning to an expanded state once the basket is advanced past a distal tip of cannula/needle/catheter 1050. The leads 1005 may be designed such that they can easily be removed by inserting a sheath over the lead 1005 that may collapse the anchoring mechanism. Each expandable arm may include an insulated electrical conductor, connected to lead 1005 and one or more electrodes (e.g., energy sources 1006). In some embodiments, lead 1005 may be inserted into an anatomical lumen (e.g., a blood vessel), the basket may expand to allow for multiple electrodes, at various radial positions, to contact the walls of the lumen.

Figure 12:
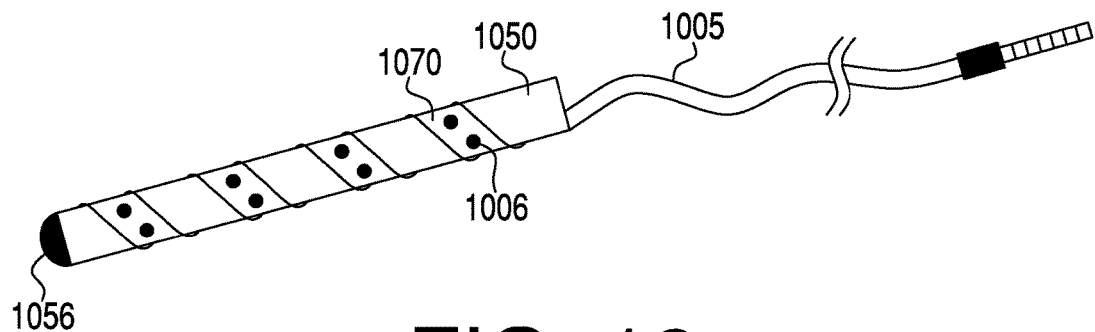
FIG. 12 illustrates a perspective view of an exemplary stimulation lead including a flexible circuit, according to one or more embodiments.

Referring to FIG. 12, a flexible circuit 1070 may include electrical traces, chips, sensors, energy sources 1006, and/or other electrodes wrapped around, or mounted upon, a polymeric or metal tube/cannula 1050, and/or one or more other lead body structures. Components of a flexible circuit 1070 may be bonded or otherwise secured in place. This type of construction may provide a very flexible lead 1005 that is easy to manufacture at low cost.

A control system may periodically deliver stimulation through various combinations of the energy emitters (e.g., electrodes, transducers, etc.) and using external feedback, such as, for example, sensors, may optimize the selection of the ideal emitters (e.g., leads or electrodes). In some embodiments, an impedance sensor may detect the volume of air in the various lung regions and the system may adjust the stimulation profile to reach the desired lung-air distribution. In one or more embodiments, an airflow sensor may measure the flow of air into the patient from an external respiratory support system and a control unit may adjust the stimulation profile to manage the amount of air moved by the patient's respiratory muscles and the amount of air moved by the external respiratory support.

When one or more stimulation arrays are placed in two different locations, for example to stimulate the left and right phrenic nerves, or as another example, the left and right intercostal muscles, the leads extending from, or attached to, the two or more sites may be secured together to provide a cleaner bundle of lead/wires leading to the external control unit/stimulator.

Figure 13:
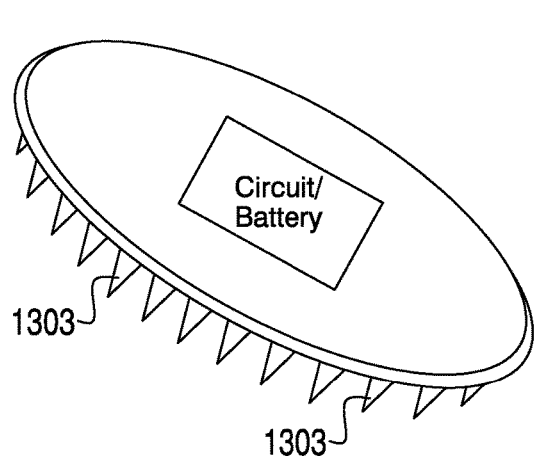
FIG. 13 illustrates a perspective view of subcutaneous electrode micro needles contained within an array, according to one or more embodiments.

FIG. 13 shows an embodiment for subcutaneous stimulation utilizing electrode micro needles 1303 contained within an array. The micro needle 1303 array has a connection means to the stimulation control unit (e.g., wireless, wired, etc.). A micro needle 1303 array may contain one more polarity electrode arrays (monopolar, bipolar, tripolar, or multipolar) that generate the electric field, or other energy source like ultrasound, for phrenic nerve excitation from a single or multiple micro needle 1303 array(s).

The distal portion of the micro needle array may be inserted into the subcutaneous layer proximal to the location of the target phrenic nerve or any other nerve of interest (e.g., the left side of the neck or the right side of the neck). Inserting a bipolar micro needle array in the subcutaneous layer of the left side of the neck may allow for excitation of the left phrenic nerve. Inserting a bipolar micro needle array in the subcutaneous layer of the right side of the neck may allow for excitation of the right phrenic nerve. Phrenic nerve excitation may result in left hemi-diaphragm recruitment, right hemi-diaphragm recruitment, or entire diaphragm recruitment.

The microneedle array may be mounted on a patch that is configured to be placed on a surface of skin. The patch may contain the energy source (e.g., battery, etc.), electronics, logic, circuitry, communication means, sensors, memory, and/or chips.

Figure 14:
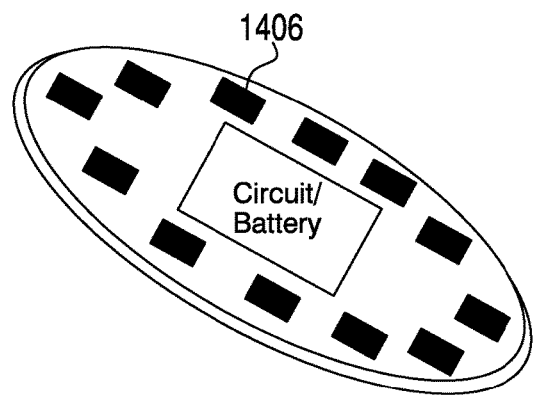
FIG. 14 illustrates a perspective view of an adhesive patch array, according to one or more embodiments.

Referring to FIG. 14, transdermal access may utilize electrodes 1406 embedded within adhesive contained within an adhesive patch array. The adhesive patch array may have a connection means to the stimulation control unit (wired or wireless). An adhesive patch array may contain one or two or multiple polarity electrode 1406 arrays (monopolar, bipolar, tripolar, or multipolar) that generate the electric field for phrenic nerve excitation from one or more adhesive patch array(s).

The distal portion of the adhesive patch may be fastened to the epidermis proximal to the location of the target phrenic nerve (e.g., the left side of the neck or the right side of the neck). Fixation of the adhesive patch array to the epidermis layer of the left side of the neck may allow for excitation of the left phrenic nerve. Fixation of the adhesive patch array to the epidermis layer of the right side of the neck may allow for excitation of the right phrenic nerve. The patch may contain the energy storage device (battery), electronics, logic, circuitry, communication device, sensors, memory, and/or chips.

In some embodiments, the energy emitter/source (e.g. leads or electrodes) extend no greater than 270° about the exterior of the stimulation lead and/or cannula/needle/catheter. The energy emitter/source (e.g. leads or electrodes) may extend anywhere in the range of 1°-270° about the exterior of the stimulation lead and/or cannula/needle/catheter. In one or more embodiments, the energy emitter/source (e.g. leads or electrodes) can extend up to 360° around the surface of the stimulation lead and/or cannula/needle/catheter. This structure may allow for the electrodes to have a more focused or localized stimulation.

The electrodes may extend no greater than 180° about the exterior of the lead, such as, for example, 30° to 120°, or 60° to 90°, about the exterior of the lead. For example, it may be desirable to avoid the stimulation of certain nerve or anatomic structures (e.g. brachial plexus) while desiring to stimulate another (e.g., phrenic nerve, etc.). In other embodiments, it may be desirable to stimulate one nerve such as the phrenic nerve with one set of stimulations parameters, for example, to provide a natural diaphragm respiratory contraction, while using another differentially directed emitter to stimulate a second nerve such as, for example, the vagus nerve to provide anti-inflammatory signaling to the brain and/or to treat sepsis.

Further, when the flexible lead/cannula/sheath comprises directional emitters, for example electrodes, the electrodes may create an electrical field which, at a given longitudinal location along the lead and axial distance from the surface of a stimulating electrode, the energy strength varies depending on the circumferential angular position in relation to the longitudinal axis of the flexible lead.

In some embodiments, three or more emitters/electrodes (e.g., sources and sinks) may be combined to create custom stimulation field shapes to optimize the stimulation of targeted nerves and to avoid/minimize the stimulation of non-targeted nerves or anatomical structures.

Where the energy source (emitters/electrodes) extends less than 360° about the exterior of the lead/cannula/sheath, the length of each emitter along the lead/sheath may be typically at least 0.5 millimeters, such as, for example, 0.5-6 millimeters. If the electrodes extends 360° about the sheath, the length of the electrodes along the sheath typically may be less than 6 millimeters, such as, for example 0.5-6 millimeters or 1-4 millimeters. Devices and systems are contemplated herein that include emitters that have different sizes and/or surface areas. For example, it may be desirable to have several large electrodes at a distance from the smaller electrodes to create a longer current path. In one example, the large electrodes may serve as a current sink.

The stimulation leads described herein may utilize flexible circuitry which may include an array of conductors bonded to a thin flexible dielectric substrate. The dielectric substrate may include liquid crystal polymer (LCP), polyimide, and/or polyvinyliden fluoride. The conductors may include graphene, gold, silver, platinum, platinum-iridium alloy, iridium oxide, titanium nitride, tungsten, or a combination thereof. A conductor may be deposited onto the dielectric substrate and then etched by chemical or laser ablative means to form an electrical circuit consisting of an electrode pad contact and a trace connecting the pad to a connector. Additional materials can be deposited (e.g., via sputtering or electroplating), upon the substrates to create discrete electrodes and/or insulative surfaces. In some embodiments, integrated circuits may be attached to the substrate, for example by soldering, to provide localized smart circuitry. Flexible circuits may have the advantage of low profile and flexibility allowing for great utility in medical applications. Multiple layers of flexible circuits, having several layers of conductive and insulative materials, may allow for the three-dimensional construction of more complex electrical networks.

Stimulation electrodes may be positioned at any location along the lead, and may have a variety of shapes, surface areas, and spacings. The stimulation lead may include at least one electrode, and may include two, three, four, five, or more electrodes. The electrodes may be spaced approximately 1 mm to approximately 2 mm apart, approximately 2 mm to approximately 4 mm apart, approximately 4 mm to approximately 8 mm apart, or greater than or equal to 8 mm apart. In some instances, a single electrode (or electrode pair) will stimulate the target tissue. In some embodiments, two or more electrodes may be used to stimulate the tissue. In some situations, a subset of electrodes may provide stimulation energy, such as, for example, one or more electrodes positioned closest to the target location. In such embodiments, the potential for stimulating non-targeted tissues, nerves, etc., may be reduced.

A relatively low level of energy may be used when electrodes are selected that are in close proximity to the targeted tissue or nerve. Peak charge output of the leads may range approximately 300 nC to approximately 6000 nC. The proximity specificity of the electrodes may help reduce the total amount of energy required to produce an action potential and thereby decreasing the power consumption for embodiments dependent on battery power.

A device may include two or more channels of energy stimulation delivered to a nerve by electrodes placed in proximity to the nerve and two channels of transvascular stimulation delivered to the nerve. The nerve may be partially or fully recruited from more than one energy source placed on the lead and/or more than one energy source placed on multiple leads. Partial nerve recruitment from more than one energy source may be useful to reduce muscle fatigue over time. This can be achieved by alternating energy delivery through multiple energy sources. Alternatively, two or more different leads can be placed at different locations, but both in the vicinity of the target nerve. Alternating stimulation between the energy emitters on the various leads may also provide options to minimize muscle fatigue as well as the avoidance of unwanted non-target nerve stimulation.

Figure 15:
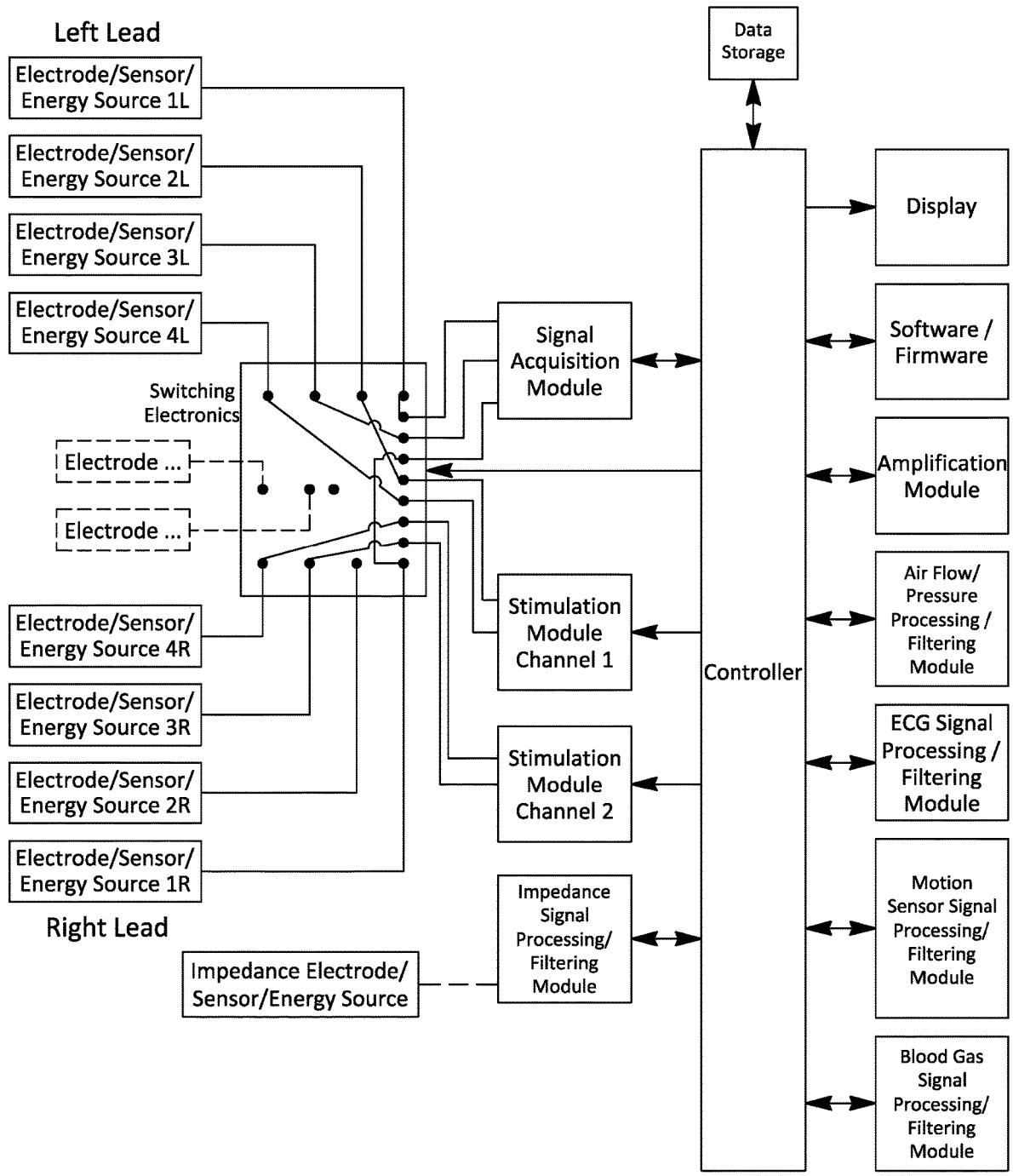
FIG. 15 illustrates a block diagram of various components of a respiratory muscle stimulation system, according to one or more embodiments.

FIG. 15 illustrates a block diagram of the various components of a system. A lead may have any number of energy sources or sensors.

The system may include a controller, which may be part of any of the control units described herein. Each of the components of the system may be operably coupled to the controller, and the controller may manage operation of each energy sources/sensors during nerve stimulation, and control the gathering of information by various sensors and electrodes.

It should be understood that the various modules described herein may be part of a computing system, and are drawn separately in FIG. 15 for explanatory purposes only; it is not necessary for the modules to be physically separate.

The systems described herein may include, for example, an external respiratory support system (i.e., ERS, "pressure support"), respiratory muscle stimulator (e.g., stimulator, stimulation lead, energy source, etc.), sensors (e.g., impedance, pressure, motion, flow, ultrasonic, electrical, thermal, chemical, optical, etc.), a control unit, a processor, a controller (e.g., a remote controller), cloud storage, peripheral interface devices, remote data storage, data analysis, data formatting, data aggregation, and/or a computer. The components and electronic devices may include one or more processors (e.g., Application Processors (AP)), a communication module, a Subscriber Identification Module (SIM), a memory module, a sensor module, an input device, a display, an interface, an audio module, a camera module, a power management module, a battery, an indicator, an alarm, a visual indicator, an optical indicator, and/or a motor.

The processor may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), and/or a Field-Programmable Gate Array (FPGA), etc. For example, the processor may include one or more of a Central Processing Unit (CPU), an Application Processor (AP), and a Communication Processor (CP). The processor may carry out, for example, calculation or data processing relating to control and/or communication of at least one other component of the system or associated electronic devices. The processor may control a plurality of hardware or software components connected to the processor by driving an operating system or an application program, and perform processing of various pieces of data and calculations. The processor may be embodied as, for example, a System on Chip (SoC). In one or more embodiments, the processor may further include a Graphic Processing Unit (GPU) and/or an image signal processor. The processor may load, into volatile memory, commands or data received from at least one (e.g., a non-volatile memory) of the other components and may process the loaded commands or data, and may store various data in a non-volatile memory.

The control unit and/or one or more other processors may serve as the communication module and serves as a communication interface to the other components of the system. An external respiratory support device, such as a mechanical ventilator, may also function as a communication module and/or processer. The communication module may include, for example, a cellular module, a Wi-Fi module, a BT module, a GNSS module (e.g., a GPS module, a Glonass module, a Beidou module, or a Galileo module, etc.), an EEPROM module, and RFID module, an NFC module, and/or a Radio Frequency (RF) module.

The system may include one or more data storage or memory components, which may include any suitable type of volatile or non-volatile memory, such as Random-access Memory (RAM), Read-Only Memory (ROM), Network Accessible Storage (NAS), cloud storage, and/or a Solid State Drive (SSD). For example, the memory may include a volatile memory and/or a non-volatile memory. The memory may store, for example, commands or data relevant to at least one other component of the system or electronic devices comprising the system. According to an embodiment of the present disclosure, the memory may store software and/or a program in the computer-like controller (e.g., control unit). The program may include, for example, a kernel, middleware, an Application Programming Interface (API), and/or application programs (or "applications"). At least some of the kernel, the middleware, and the API may be referred to as an Operating System (OS).

The system may include one or more sensors, as described herein. For example, sensors which measure a physical state of the subject or environment, and/or detect an operation state of the connected electronic devices. The sensors may convert the measured or detected information into an electrical signal. The sensor may, for example, measure/monitor impedance, respiration, airway pressure, gas distribution, air flow, $CO_2$, $O_2$, temperature, blood sugar, heart rate, blood pressure, color, sound, and/or motion. The system may also include an electronic-noise sensor, an electromyography (EMG) sensor, an electroencephalogram (EEG) sensor, an electrocardiogram (ECG) sensor, an Infrared (IR) sensor, an iris scan sensor, a finger scan sensor, and/or other sensors disclosed herein or known in the art. A sensor module may further include a control circuit for controlling one or more sensors included therein. Additionally, the sensors may include, for example, at least one of a gesture sensor, a gyro sensor, an atmospheric pressure sensor (barometer), a magnetic sensor, an acceleration sensor, a grip sensor, a proximity sensor, a color sensor (e.g., red, green, and blue (RGB) sensor), a biometric sensor (medical sensor), a temperature/humidity sensor, an illuminance sensor, and/or an Ultraviolet (UV) sensor. Any of the individual electronic devices may further include a processor configured to control one or more sensor modules, as a part of the processor or separately from the processor, and may control the sensor module while the processor is in a sleep state.

The system may include one or more input devices such as, for example, a touch panel/screen, a (digital) pen sensor, a remote control, a key, and/or other input devices. The touch panel may use, for example, at least one of a capacitive type, a resistive type, an infrared type, and an ultrasonic type. The touch panel may further include a control circuit. The touch panel or other elements of the input device may further include a tactile layer, and provide a tactile reaction to the user.

The system includes one or more input/output interfaces, which function as an interface that may transfer commands or data input from a user or another external device to the other element(s) of the system or individual devices comprising the system. Furthermore, the input/output interface may output the commands or data received from the other element(s) of the system or electronic devices to the user (e.g., healthcare practitioner, or patient, etc.) or another external device.

The system of the embodiments of this disclosure may include one or more displays. Examples of a display may include a Liquid Crystal Display (LCD), a Light-Emitting Diode (LED) display, an Organic Light-Emitting Diode (OLED) display, a micro-electro-mechanical Systems (MEMS) display, and an electronic paper display. The one or more displays may communicate, for example, various types of content (e.g., text, images, videos, icons, or symbols) to users. The display may include a touch screen, and may receive, for example, a touch, gesture, proximity, or hovering input using an electronic pen or a user's body part. The display may include a panel, a hologram device, or a projector. The panel may be implemented to be, for example, flexible, transparent, or wearable. The panel may be embodied as a single module with the touch panel.

The system may include one or more indicator/alarm/notification modules which may display a particular state (e.g., a booting state, a message state, a charging state, treatment stage, patient condition, warning, etc.) of the system or electronic devices within the system. A motor or other suitable device may convert an electrical signal into a mechanical vibration, and may generate a vibration, a haptic effect, or the like to alert a healthcare practitioner or patient of an event or situation. Although not illustrated, each electronic device/component may include a processing device (e.g., a GPU).

Energy sources may be electronically coupled to switching electronics, which may be communicably coupled to the controller. The switching electronics may include an application-specific integrated circuit, or other type of circuitry that enables the controller to independently control energy sources of a stimulation array. A hub also may be connected to switching electronics and may be used as an energy source or electrode or sensor.

In some embodiments, electrodes may be used for both electrically stimulating targets (e.g., nerves and/or muscles) and for gathering physiological information. When being used for nerve or muscle stimulation, a first combination of electrodes (e.g., one, two, three, or more electrodes) may be electrically coupled to a first stimulation module channel for stimulation of a first nerve (e.g., the right phrenic nerve), and a second combination of electrodes on another lead (e.g., one, two, three, or more electrodes) may be electrically coupled to a second stimulation module channel for stimulation of a second nerve (e.g., the left phrenic nerve). Electrical signals may be sent from the first and second stimulation module channels to the electrode combinations to cause the electrodes to stimulate the nerves. In other examples, more than two electrode combinations may be used to stimulate one or more target nerves, and the system may include more than two stimulation module channels. Some electrodes may also be dedicated to gathering physiological data (e.g., impedance, etc.). Some embodiments described herein may use energy sources and sensors that can be implanted in the patient, located on the outside of the patient, or a combination of both.

Electrodes may be further configured to sense physiological information from a patient, such as nerve activity, ECG, or electrical impedance, breathing, etc., as described throughout this disclosure. When being used for sensing, one or more of electrodes may be electronically coupled to a signal acquisition module. The signal acquisition module may receive signals from electrodes.

Switching electronics may selectively couple electrodes to a first stimulation module channel, a second stimulation module channel, or a signal acquisition module. In one example, any electrode can be used for nerve stimulation, and any electrode can be used for sensing functions described herein. In other words, each electrode may be configured to stimulate nerves, and each electrode may be configured to sense physiological information.

The signal acquisition module may further be coupled to one or more sensors configured to gather physiological information from a patient. For example, the system may include one or more of a blood gas sensor or a pressure sensor. These sensors may be located in lumens of a stimulation lead, outside of the patient in fluid communication with a lumen, on an outer surface of a catheter, or in any other suitable location. In one example, a blood gas sensor may be housed in or fluidly connected to the lumen, while a pressure sensor may be housed in or fluidly connected to the lumen. The blood gas sensor may measure the amount of $O_2$ or $CO_2$ in the patient's blood. A pressure sensor may measure the central venous pressure (CVP) of the patient.

A signal from a blood gas sensor may be transmitted to a blood gas signal processing/filtering module for processing and filtering to determine blood gas levels. Signals from electrodes, when they are used for sensing, may be sent to a nerve signal processing/filtering module, an ECG signal processing/filtering module, or an impedance signal processing/filtering module, as appropriate. Signals from electrodes or other sensors may be sent to an amplification module, if necessary, to amplify the signals prior to being sent to the appropriate processing/filtering module.

In one embodiment, sensors can detect information from nerve signals which can be used to help manage the delivery of the therapy for the patient. For example, the electrical activity of a respiratory muscle (e.g. diaphragm, intercostal, etc.) as well as vagal signals from pulmonary stretch receptors, may be used to optimize parameters related to the delivery of the external respiratory support system and/or the respiratory muscle stimulation system.

For patients with a moderate to high level of consciousness, the electrical activity of the diaphragm may provide an accurate reflection of the patient's neural respiratory drive. In addition to this neural signal, there are vagally-mediated reflexes which sense lung stretch to limit the volume of inspiration thereby preventing over-distension (Hering-Breuer inflation reflex) and to prevent the deflation of the diaphragm during exhalation (Hering-Breuer deflation reflex).

Positive pressure provided by the external respiratory support, negative pressure provided by the stimulated respiratory muscle system, or both, may be adjusted and coordinated to respond to the Hering-Breuer reflex neural signals. For example, increasing the work of breathing provided by electrically stimulated respiratory muscles (e.g., negative pressure respiration) may allow for a reduction in the positive pressure required from a ventilator. The reduction in positive pressure may reduce the likelihood of barotrauma or lung stretch injury.

Systems and devices described herein may comprise a blood oxygenation and/or $CO_2$ removal device which processes the blood of the patient to and adjusts blood gases to predetermined levels. Systems described herein may also comprise at least one physiological sensor, functionally connected to the control unit, configured to obtain patient physiological data relating to at least one of tidal volume, respiratory pressure, respiratory rate, work of breathing, $CO_2$ saturation, oxygen saturation, temperature, blood pressure, heart rate, blood oxygen levels, and/or brain activity. The physiological data may be used to manage the distribution of gas/air in a patient's lungs during a respiratory cycle.

A system operating in A-Mode may include a closed-loop operation to autonomously stimulate a respiratory muscle (e.g., the diaphragm, intercostals, etc.). This mode may make use of any patient response signal (feedback) that will help indicate that pacing is required. These signals include, but are not limited to, oxygen saturation, end-tidal $CO_2$ (EtCO$_2$), airflow, impedance, heart rate, movement-detecting accelerometer signals, or a combination thereof. Pacing may be administered continuously in A-mode. An algorithm may be used to detect and/or modify physiological response signals to determine whether a change in stimulation pattern, frequency, breath rate, intensity, type, and/or shape profile is required to elicit a desired response.

Figure 16:
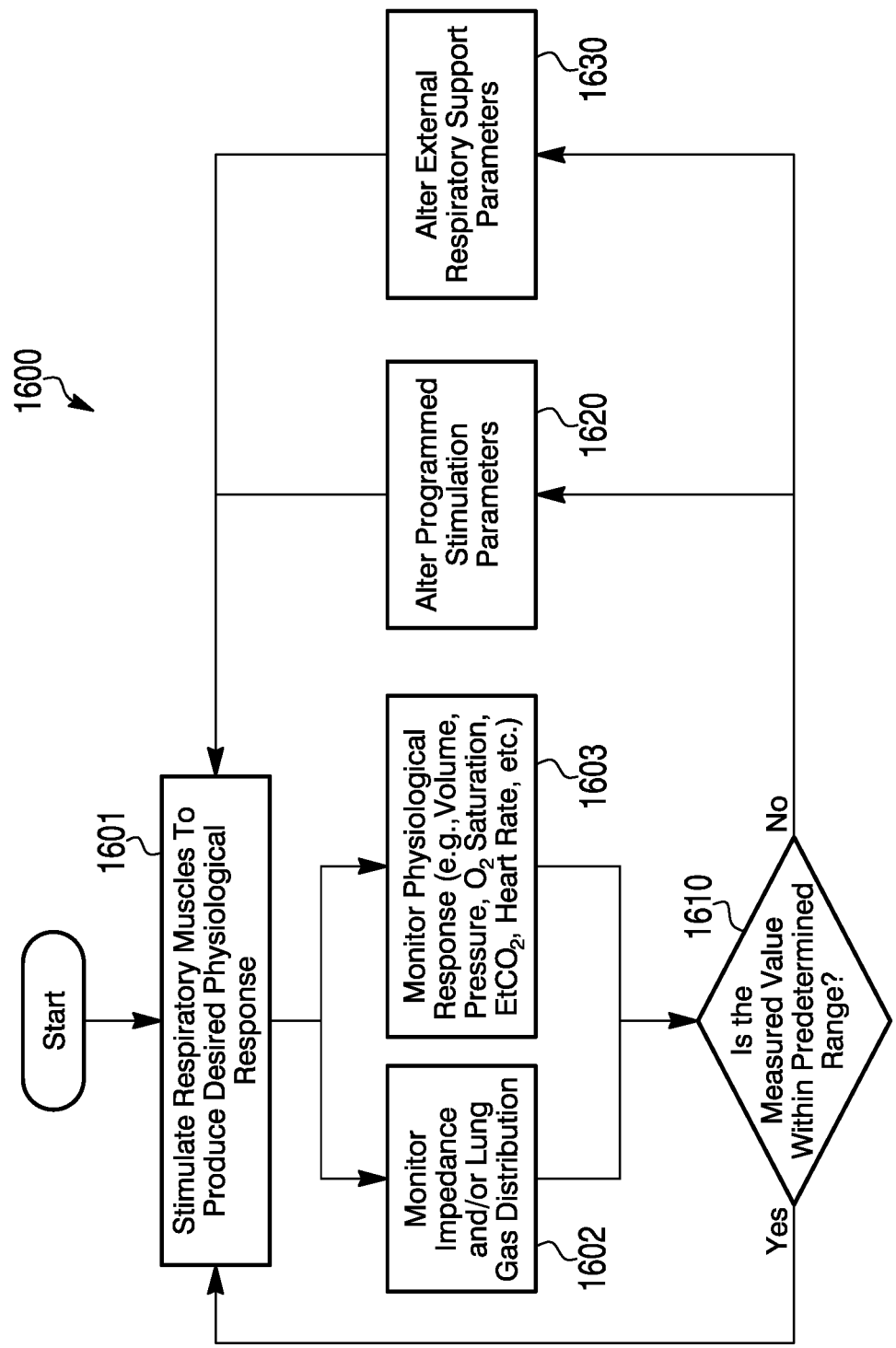
FIG. 16 is a flowchart of a method for operating a respiratory muscle stimulation system in autonomous mode, according to one or more embodiments.

FIG. 16 shows a flowchart of an exemplary process 1600 of a system operating in A-mode. When stimulation is started in A-mode, respiratory muscles may be stimulated to produce a desired physiological response (step 1601). The sensors may be used to monitor whether a desired physiological response occurred. During stimulation, the system may monitor one or more impedance measurements (step 1602) and/or monitor patient physiological responses (step 1603). The system may then determine if one or more impedance measurements and/or patient physiological responses is within a predetermined range (step 1610). The predetermined range may be programmed by a user, a selected setting programmed into the system, and/or determined based on one or more measured characteristics, properties, or parameters. If the system determines that one or more impedance measurements and/or patient physiological responses is within a predetermined range, it may continue stimulating respiratory muscles to produce a desired physiological response (step 1601). If the system determines that one or more impedance measurements and/or patient physiological responses is not within a predetermined range, it may alter programmed stimulation parameters (step 1620) and/or alter external respiratory support parameters (step 1630), before continuing to stimulate respiratory muscles to produce a desired physiological response (step 1601).

In some embodiments, a multi-electrode lead may be secured in place across the phrenic nerves. The controller/stimulation/system may be used to determine the best electrode set for each hemi-diaphragm. Determining the best electrode set may include finding the best electrode combination which can be completed by sending signals through different combinations of electrodes on the multi-electrode lead. The selection may be automated using feedback from the sensors and/or involve feedback from a healthcare professional or other user. Once an electrode set is selected, the stimulator may go through a process to select the proper signal by varying aspects of the signal such as current and determining the response. If this process is automated, the system may send a set of signals, and the response from the sensors will determine which signal triggered the highest response from the targeted respiratory muscle (e.g. diaphragm, etc.). This may also be done manually by having the healthcare professional or other user involved in determining the response from the muscle/nerve.

Figure 17A:
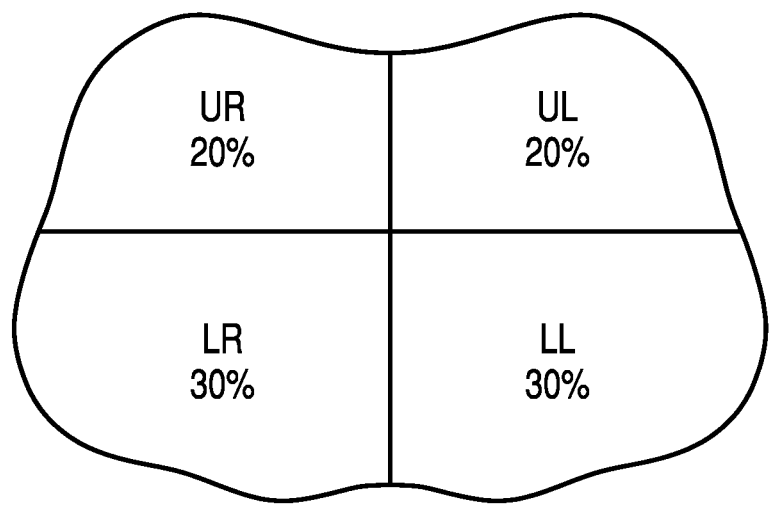
FIGS. 17A and 17B illustrate graphical depictions of lung gas volume distributions calculated by EIT, according to one or more embodiments.
Figure 17B:
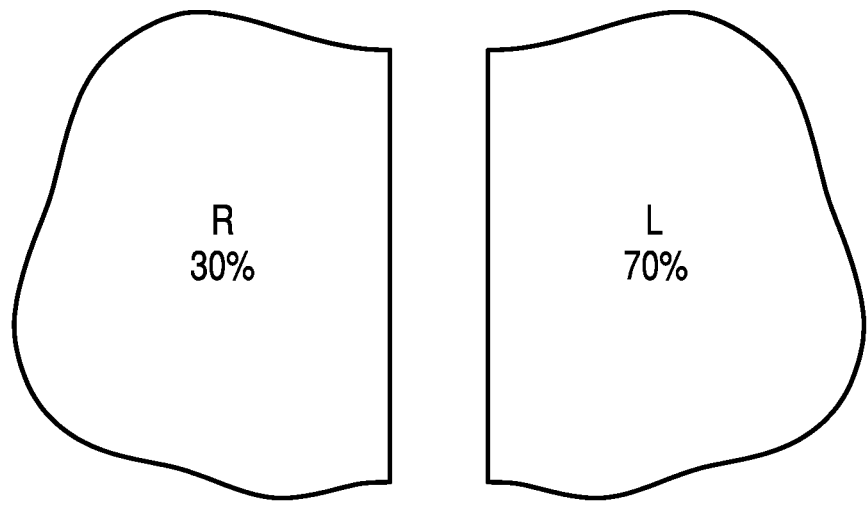

As described previously, tissue impedance sensing (TIS) may be used to form a tomographic image and/or analysis of tissue condition or composition. A system may be configured to adjust lung gas volume, pressure, and distribution between left and right, and anterior (upper) and posterior (lower) regions, of a patient's lungs. A baseline measurement of lung gas distribution by region including left anterior (LA), right anterior (RA), left posterior (LP), right posterior (RP) may be collected. A graphic display of one such example distribution in shown in FIG. 17A. The specific 20%-30%-20%-30% distribution shown in FIG. 17A, is one example, other distributions are contemplated. The display may be shown via an output device of the system or otherwise communicated to a user. Based on the measured distribution or generated display, one or more stimulation parameters, and/or external respiratory support parameters, may be varied to adjust the distribution of lung gas, as described herein. The example in FIG. 17A showing two regions of each of two lungs is one example. Other configurations include calculating and displaying the lung gas distribution between two lungs, as shown in FIG. 17B.

In addition, or alternatively, a volume of air moved during each respiratory cycle (e.g., tidal volume), a peak airway pressure, a plateau pressure, and/or a pressure-time product may be measured. Other characteristics of a breathing cycle can also be measured as described herein, as well as in some embodiments the external respiratory support parameters. Data regarding characteristics of a breathing cycle may assist with adjusting the stimulation energy for balancing lung gas distribution.

Referring to FIG. 18A, an exemplary subject had a higher level of lung gas in the upper regions of the lungs, and most lung gas was being moved in the upper right side. Tidal volume was lower than desired, and airway pressure was bordering on the higher side. Based on the impedance and other sensor data collected, the stimulation array was activated. Referring to FIG. 18B, after respiratory and stimulation parameters were adjusted, the tidal volume increased noticeably, and the peak airway pressure was lowered to a safer range. Better balance of air between upper and lower lung regions was achieved. Further adjustment of the respiratory muscle stimulator achieved better left-right lung gas balance, shown in FIG. 18C. The distribution of air in lung quadrants can be changed by delivering energy to the respiratory muscles or the nerve controlling the respiratory muscles. The distribution of air between left and right lungs can be altered by changing the energy delivery to left and or right side respiratory muscles. The distribution of air between the anterior or posterior lobes can be altered by stimulating different nerve axons in the nerve fibers by triggering alternate energy sources (electrodes) that control different respiratory muscle fibers. The distribution of air between the anterior or posterior lobes may also be accomplished by stimulating varying intensities to different intercostal or abdominal muscles. The total volume of air in the lungs may be adjusted by altering the energy delivered (e.g., total charge) to the respiratory muscles and/or the nerves that control the respiratory muscles. By balancing the work of the external respiratory support device with the work done by the respiratory muscles, the lung gases and lung volumes may be better distributed to reduce injury, improve patient comfort, rehabilitate, strengthen, or exercise respiratory muscles. Sensors may be used to determine or sense if respiratory muscles begin to fatigue, and in these circumstances the work contribution from the respiratory muscles may be lowered, and the work contribution from the external respiratory support device may be increased.

Figure 19:
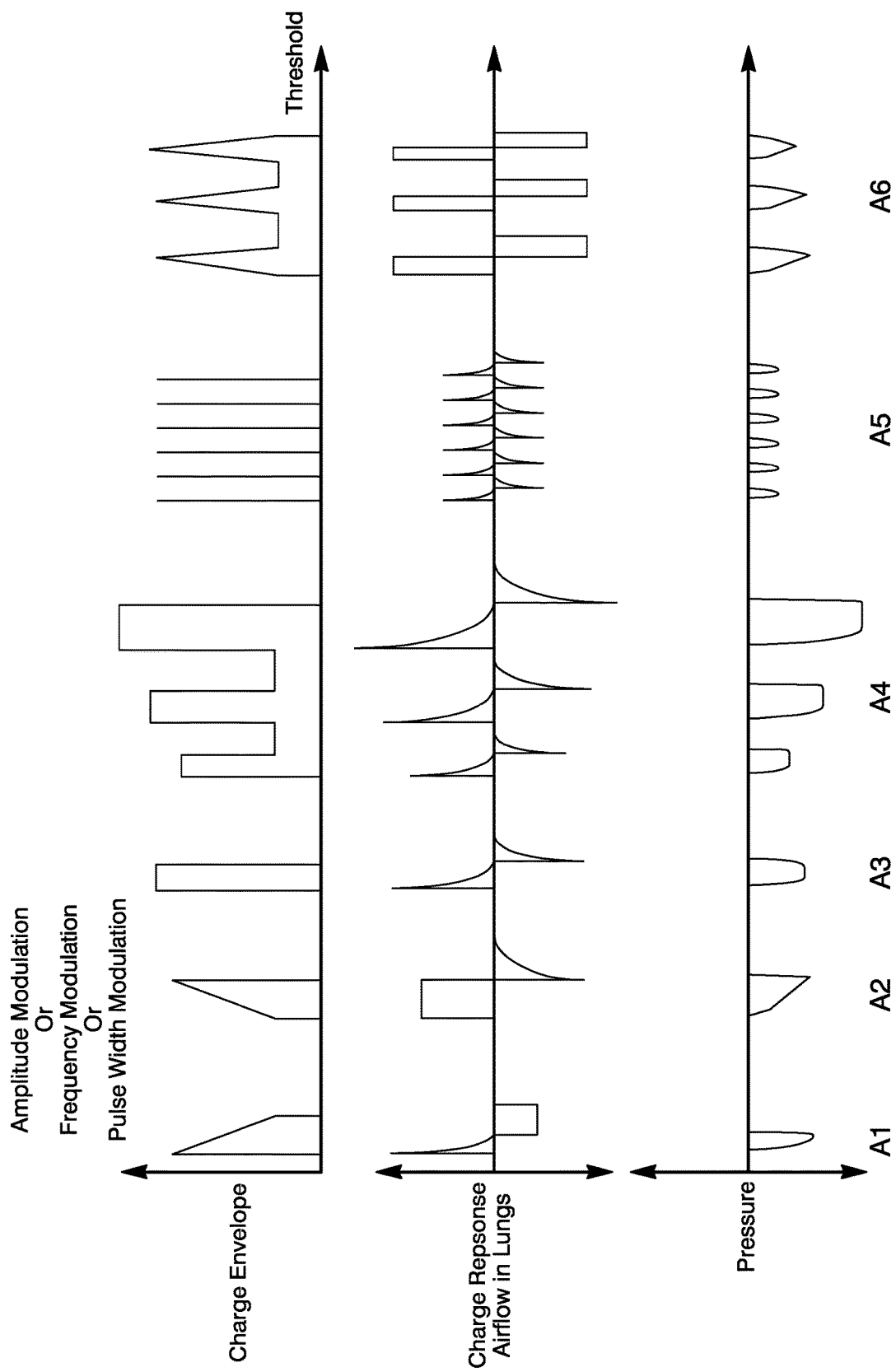
FIG. 19 illustrates examples of representative ramp envelopes where the ramp slopes represent the modulations in pulse width, pulse frequency, and/or amplitude within a train, according to some embodiments.

Referring to FIG. 19, multiple non-limiting, exemplary scenarios are described where delivery of energy to the respiratory muscles and/or the nerves controlling respiratory muscles, can lead to a body's normal mucociliary action, produce a cough, or otherwise assist in movement of fluid from the patient's respiratory tract. The waveforms described herein may induce coughing, and the active movement of fluid within an individual's lung through more physiological negative pressure ventilation, in some cases accelerated mobilization of the lung fluids (secretions, mucus, mucus plug, etc.). The respiratory muscles are stimulated with an energy charge envelop that generates cough like response by delivering energy that leads to sudden contraction of respiratory muscles and gradual release over short duration (in one embodiment 1-3 seconds) as shown in FIG. 19(A1). The cough response can also be generated by gradually contracting the respiratory muscles over a short duration (in one embodiment 1-3 seconds) and suddenly releasing the respiratory muscle contractions as shown in FIG. 19(A2) or suddenly contracting respiratory muscles and holding it for a short duration (in one embodiment 1-3 seconds) and suddenly relaxing the muscles as shown in FIG. 19(A3). In some embodiments, such as those shown in FIGS. 19(A4) to 19(A6), a series of cough responses can be induced with a small time-gap (e.g., 1-10 seconds) between them.

The respiratory muscles may be gradually contracted or suddenly contracted. The muscles may be kept contracted by fused contraction for a short duration or relaxed as soon as contracted. The muscles may be relaxed gradually or suddenly. The charge may be modulated in a stimulation train (multiple pulses) by modulating amplitude (e.g., current or voltage), by modulating pulse width, and/or by modulating frequency of pulses.

In some embodiments, a series of energy pulses may generate hiccup (twitches, unfused contraction) in the respiratory muscles. The series of energy pulses can be delivered at a vibratory frequency (e.g., 1-10 Hz) that helps to mobilize the fluid in the lungs. The series of energy pulses could be delivered for a small duration (e.g., 1-10 minutes) multiple (e.g., 1-24) times a day.

A health care practitioner, other user, or the computer controller (e.g., in automatic mode) may modify the stimulation energy, frequency, amplitude, and/or other parameters to achieve a desired effect (e.g., respiratory secretion, mucus, and/or body fluid migration). Sensors described herein, such as impedance, pressure, volume, and air flow, may be used to assess the progress of the secretion liberation therapy. In some embodiments, the RMS may be combined with external positive pressure therapy, or exterior torso vibratory therapy, to achieve a desired effect. Coordinated muscular contractions, amplified vibrations, and/or increased inspiratory/expiratory pressure can individually or collectively lead to the loosening and removal of respiratory secretions.

In some instances, suctioning devices can be used to assist with respiratory secretion removal. Devices and systems described herein, including suctioning devices, may be inserted into the patient's lungs to remove the dislodged materials during and/or after the stimulation is delivered.

Respiratory secretions, including mucus and other fluids, may be readily exposed, dislodged, disrupted, liberated and transported out of the patient using the methods and systems described herein. Removal of respiratory secretions may be associated with an increase in tidal volume, better lung region gas distribution, shortened rehabilitation times, and other therapeutic benefits.

Delivery of electrical stimulation may be triggered in multiple ways. In one or more embodiments, a healthcare professional or other user operates a handheld controller. The controller may allow for operator flexibility in interfacing with a stimulation system, possibly allowing a user to be closer to the subject. Such controllers may also allow for subjects to control delivery of stimulation. This controller could have unique controls or be an extension of controls available on another interface within the stimulation system.

For manually triggered electrical stimulation, a remote controller may trigger stimulation through a button press, or another form of manual triggering by the operator. For electrical stimulation triggered through a closed loop system, the remote controller may be used to initiate the closed loop process, or to interrupt this process.

In some embodiments, a closed loop control system for triggering electrical stimulation delivery may be employed. Such a closed-loop system automates the stimulation delivery process, removing operator-induced error. One or more sensors can be used to determine when to trigger stimulation delivery. Airflow can be measured to trigger stimulation at the end expiratory phase of a patient's breathing cycle, or another phase of the breathing cycle. Pressure sensors within the breathing circuit may be used to determine what phase of the breathing cycle a patient is in to trigger stimulation at the end expiratory phase of a patient's breathing cycle, or another phase of the breathing cycle. Accelerometers, gyroscopes, or other motion sensors may be used to detect a patient's breathing and trigger stimulation at the appropriate phase of the patient's breathing cycle. $CO_2$, $O_2$, and blood gas sensors may be used to detect a patient's breathing and trigger stimulation at the appropriate phase of the patient's breathing cycle. Central venous pressure may be used to determine a phase of the breathing cycle a patient is in to trigger stimulation at the end expiratory phase of a patient's breathing cycle, or other phase of the breathing cycle.

Impedance sensors may be used to measure lung function and determine what phase of the breathing cycle a patient is in to trigger stimulation at the end expiratory phase of a patient's breathing cycle, or another phase of the breathing cycle. Electrodes may be used to measure signals on the phrenic nerve to determine location of the phrenic nerve during electrode placement.

In a closed loop system, controls are needed as well as sensors. Multiple controls can be used to determine when the system needs to react. Stretch receptors may be used as a control for stimulation charge or stimulation frequency (within a pulse train and/or between pulse trains). Cognitive function sensors, such as devices to measure brainwaves, ECG, alertness, etc., may be used to monitor brain function. Work of breathing can be used as a control for stimulation charge or frequency (within a pulse train and/or between pulse trains). Airway or Central Venous Pressure may be used as a control for stimulation duration, stimulation intensity, or stimulation frequency (within a pulse train and/or between pulse trains). Volume may be used as a control for stimulation duration, stimulation intensity, or stimulation frequency (within a pulse train and/or between pulse trains). Blood gas may be used as a control for stimulation duration, stimulation intensity, stimulation frequency (within a pulse train and/or between pulse trains), or frequency of rep delivery.

Both inspiratory and expiratory muscles can be stimulated, each stimulation coordinated to provide the desired respiratory outcome. Higher stimulation levels at predetermined frequencies of stimulation may be used to induce a cough response to help mobilize secretions in a patient's lungs, as described herein.

Respiratory muscles, such as the diaphragm, may be exercised by initiating several contractions of the muscle (reps). The reps can be initiated through patient participation, electrical stimulation, other means, or a combination thereof. Each rep may have a contraction strength, and based on the strength of contraction produced by a rep, a rep can range from weak to strong. A desired number of reps performed in series is called a set. There can also be a waiting period (rest) between sets. The determination of reps, sets, and rest in an exercise regime is considered the dosage. Different dosages are necessary for different patient parameters, conditions, and/or circumstances. Examples of dosages disclosed herein are exemplary and may address the need of defining dosages for exercising of the diaphragm.

External respiratory support may be utilized during surgery or intensive care environments. The condition and strength of the diaphragm deteriorates rapidly under external respiratory support. Phrenic nerve stimulation or diaphragmatic pacing may be used to prevent said deterioration. Stimulating the diaphragm approximately 60 to approximately 120 times a day may improve respiratory muscle strength. Without being limited by theory, such stimulation may assist in maintaining strength of an already strong diaphragm.

Stimulating respiratory muscles more frequently (e.g., for several minutes each hour, every few seconds for approximately 5 minutes to approximately 10 minutes each hour, every few seconds for approximately 10 minutes to approximately 20 minutes each hour, or every few seconds for approximately 20 minutes to approximately 50 minutes each hour) may also be beneficial. Stimulating one or more respiratory muscles as frequently as every other breath or with every breath may improve and/or maintain diaphragm muscle strength and for reducing lung injury from positive pressure ventilation.

Stimulating the diaphragm with approximately 5 stimulation trains to approximately 60 stimulation trains, approximately every 15 minutes, every 20 minutes, every 30 minutes, or every hour, during surgery (e.g, intermittently) may preserve diaphragm strength and also help reduce atelectasis and other lung injury. When using electrical stimulation, the reps may be triggered manually by an operator, through a direct trigger from the Mechanical Ventilator, via feedback from sensors of the stimulation system, via direction from the Controller, or a combination thereof. In some embodiments, muscle fatigue can be measured to mitigate muscle overuse.

Various therapy and exercise dosages and regimens are described in U.S. Patent Application Publication No. 2019/0175908, incorporated by reference herein in its entirety.

Diaphragm exercise may prevent diaphragm deterioration and may be used in any scenario in which a patient is on respiratory support. Respiratory support may include, but is not limited to, PPMV, ECMO, ECCO2R, CPAP, and BiPAP. In order to prevent diaphragm deterioration, the diaphragm exercise dosage is ideally applied as soon as the patient is put on respiratory support. Stimulating the diaphragm often (e.g., every breath to every third breath, every minute to every ten minutes, or less frequently, for example, approximately 60 contractions every 3-8 hours) may keep the diaphragm from deteriorating due to disuse. When using electrical stimulation, the stimulation trains may be triggered manually by an operator, through a direct trigger from the Mechanical Ventilator, via feedback from sensors of the stimulation system, or a combination thereof.

Diaphragm exercise may recondition the diaphragm after deterioration and may be used in any scenario in which a patient is on respiratory support. In some embodiments, the diaphragm has already deteriorated, and stimulation is used to strengthen and rehabilitate the diaphragm. Such stimulation can be delivered in sets, in which multiple stimulation trains (e.g., approximately 10 to approximately 30 stimulation trains) are delivered in a set. Multiple sets can be delivered in a session, such as, for example, approximately 2 to approximately 8 sets per session, with a rest period in between sets of approximately 1 minute to approximately 10 minutes. Multiple sessions (e.g., 2-4) can be delivered in a 24-hour period. Other dosages described herein may also be used to re-condition the diaphragm. When using electrical stimulation, the reps may be triggered manually by an operator, through a direct trigger from the Mechanical Ventilator, via feedback from sensors of the stimulation system, or a combination thereof.

EXAMPLES

The following examples are intended to illustrate the present disclosure without being limiting in nature. It is understood that the present disclosure encompasses additional embodiments consistent with the foregoing description and following examples.

Example 1

Eleven subjects were selected for a trial with a respiratory muscle stimulation system. Each selected subject was a human adult who had been receiving positive pressure, external respiratory support from a mechanical ventilator for at least seven days. A summary of the trial subject group is shown below in Table 1.

TABLE 1

| Summary of Subject Group | |
|---|---|
| Age | 62.4 ± 10.2 years |
| Body Mass Index | 27.2 ± 5.5 |
| Baseline Maximal Inspiratory Pressure (MIP) | 24.1 ± 15.4 cm H$_2$O |
| Time on mechanical ventilator prior to trial | 19.7 ± 17.9 days |

Nine of the eleven subjects were treated with the respiratory muscle stimulation device. A 9.5 French catheter including a stimulation lead connected to at least two electrode arrays was inserted into the left subclavian vein of each subject, such that at least one electrode array was proximate to the left phrenic nerve and at least one electrode array was proximate to the right phrenic nerve.

Each subject was scheduled to receive three sessions of therapeutic respiratory muscle stimulation via the stimulation lead, every day. Each session included four sets, with a five minute rest period between sets. Each set included ten stimulation trains. The stimulation was delivered simultaneously to the left phrenic nerve and the right phrenic nerve, by quad-polar and bipolar electrode combinations at approximately a 15 Hz frequency. The amplitude of the stimulation ranged from 0.1 mA to 13.5 mA and was delivered at pulse widths of approximately 200 μsec to approximately 300 μsec.

All nine of the trial subjects successfully received the catheter including the stimulation lead, and the catheter was successfully removed from each subject. Additionally, all subjects demonstrated successful capture of at least one phrenic nerve and exhibited respiratory muscle contractions in response to the stimulation. Most patients received a majority of the scheduled therapy, with each subject receiving an average of 10.2 days of stimulation sets. Finally, seven of the subjects successfully weaned from the mechanical ventilator. Of those who did not wean, one left the trial to receive a lung transplant and the other chose to discontinue mechanical ventilation four days into the trial due to a previously existing undiagnosed illness.

The subjects showed improved maximal inspiratory pressure (MIP) and improved rapid shallow breathing index (RSBI). This resulted in shortened mechanical ventilator weaning time, and reduced length of stay in ICU and hospital environments. The MIP and RSBI data is summarized in Tables 2 and 3, MIP and RSBI measurements from the beginning of the study (baseline) were compared to MIP and RSBI measurements at a follow-up appointment.

TABLE 2

| Summarized Changes in Maximum Inspiratory Pressure | | | | |
|---|---|---|---|---|
| Mean ± Standard Deviation; [Range] in cm H$_2$O | | | | |
| MIP | MIP Baseline | MIP Follow-up | Change in MIP | Days Between Measurements |
| All Nine Subjects | 21.9 ± 12.6; [11-45] | 35.9 ± 14.1; [18-61.5] | 13.9 ± 20.6; [−21-45.6] | 13 ± 6.1; [6-24] |
| Seven Successfully Weaned Subjects | 18.7 ± 10.5; [11-41.3] | 38.4 ± 15.1; [18-61.5] | 19.7 ± 17.9; [−3.1-45.6] | 14.9 ± 5.6; [8-24] |

TABLE 3

| Summarized Changes in Rapid Shallow Breathing Index | | | | |
|---|---|---|---|---|
| Mean ± Standard Deviation; [Range] | | | | |
| RSBI | RSBI Baseline | RSBI Follow-up | Change in RSBI | Days Between Measurements |
| All Nine Subjects | 142.6 ± 49.6; [53-229] | 79.9 ± 50.2; [35-172] | −62.7 ± 60.4; [−172-0] | 7.2 ± 4.5; [1-13] |
| Seven Successfully Weaned Subjects | 143 ± 57.3; [53-229] | 79.5 ± 51.4; [39-172] | −63.5 ± 64.4; [−172-0] | 7.7 ± 4.9; [1-13] |

The results above suggest that the systems and methods described herein are safe for use in patients requiring mechanical ventilation. They appeared to improve inspiratory muscle strength, as evidenced by increased MIP, and respiratory function, as indicated by changes in RSBI score, in patients who were previously dependent on mechanical ventilation. Further, the systems described herein appeared to facilitate successful weaning in patients who required prolonged mechanical ventilation.

Figure 20:
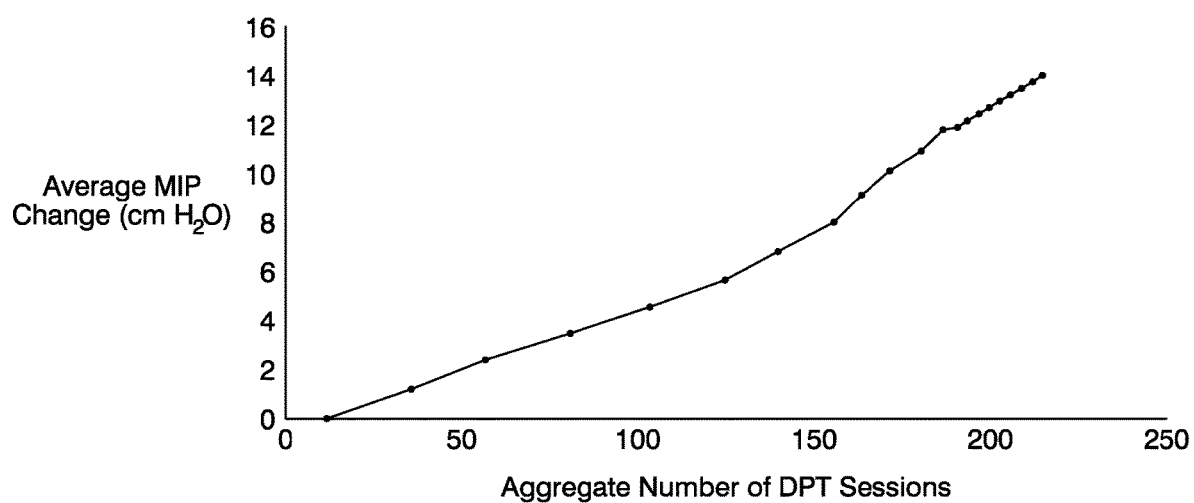
FIG. 20 is a plot of average change in maximum inspiratory pressure versus aggregate number of respiratory muscle stimulation sessions, according to one or more embodiments.

In addition, the average change in MIP was plotted against the aggregate number of respiratory muscle stimulation sessions. This plot is shown in FIG. 20. As can be seen from FIG. 20, the average change in MIP improved as more stimulation sessions were performed.

These data indicate the systems are methods described herein (including those described in the patents incorporated by reference), are safe and feasible for use as a respiratory muscle stimulation system in patients on prolonged mechanical ventilation. Additionally, the systems and methods described herein have the potential to improve weaning outcomes in patients who require prolonged mechanical ventilation.

Example 2

Surprisingly, the stimulation therapy induced mobilization of mucus and fluid in the respiratory tract of the subjects. The subjects reported feeling "pulling," "tugging," and "hiccup" sensations without pain, indicating that respiratory muscle stimulation therapy may assist in the removal of fluid from the respiratory tract of patients receiving external respiratory support.

In at least one subject from the trial described in Example 1, mobilization of a mucus plug from atelectatic lung bases was observed. The mucus plug was removed from an endotracheal tube via bronchoscopy.

The subject, a 75-year-old Caucasian female, was admitted to the hospital with a 5-day history of altered mentation and generalized weakness. She was intubated for acute respiratory failure and started on broad-spectrum antibiotics. Her past medical history was significant for extrinsic restrictive lung disease with use of CPAP at home, hypertension, chronic kidney disease, anemia, obesity, depression, and hyperthyroidism. In addition, she had a prolonged history of non-specific, chronic asthenia following multiple unsuccessful work-ups at outside facilities.

Antibodies for myasthenia gravis were negative and following repeated failures of spontaneous breathing trials, she was enrolled in the trial. Catheter insertion was completed without difficulty. Catheter placement was confirmed by chest x-ray. At the beginning of the study, the subject's MIP was −14.3 cm $H_2O$. After up to three daily sessions of respiratory muscle stimulation therapy, she sustained two separate acute hypoxic episodes due to mucus plug mobilization.

During the first hypoxic episode, the subject experienced respiratory distress due to a large dislodged mucus plug, which was expelled. After removal of the dislodged mucus, the subject's respiratory status recovered. Positive pressure mechanical ventilation was increased overnight to assist the subject's recovery.

Two days later, the subject exhibited a second episode of acute hypoxia and respiratory distress. She underwent a bedside fiberoptic bronchoscopy to remove a large, thick mucus plug located at the lower portion of her endotracheal tube, which was cleared with suctioning. Evaluation of both lungs revealed thin lower lobe secretions which were gently suctioned. No obvious bleeding or endobronchial lesions were noted.

After mucus plug clearance, the subject had a daily reduction in external respiratory support and the patient was weaned from mechanical ventilation on day 9. The subject's MIP improved to −18 cm $H_2O$. The subject was successfully weaned from mechanical ventilation after 18 sessions of respiratory muscle stimulation, and was extubated nine days after enrollment in the study. A summary of the patient's respiratory status during the nine day period is shown below in Table 4.

TABLE 4

Exemplary Lung Secretion Mobilization Treatment

| Day | SBT(min) | ERS Pre-set Pressure (cm $H_2O$) | ERS PEEV (cm $H_2O$) | Respiration Rate (breaths/minute) | MIP (cm $H_2O$) | Tidal Volume (mL) | Number of Stimulation Sessions |
|---|---|---|---|---|---|---|---|
| 1 |  | 15 | 5 |  | 14.3 |  | 1 |
| 2 | 16 | 15 | 5 | 18 |  | 420 | 3 |
| 3 | 11 | 15 | 5 | 21 |  | 420 | 2 |
| 4 | 16 | 12 | 5 | 20 |  | 305 | 3 |
| 5 | 6 | 10 | 5 | 23 |  | 350 | 2 |
| 6 | 22 | 15 | 5 | 21 |  | 374 | 3 |
| 7 | 4 | 7 | 5 | 24 |  | 271 | 3 |
| 8 |  | 7 | 5 | 22 |  | 265 | 1 |
| 9 |  |  |  |  | 18 |  |  |

SBT refers to duration in minutes of a spontaneous breathing trial to assess a subject's ability to breathe with minimal or no external respiratory support (ERS). The ERS parameter columns refer to the positive pre-set pressure and the positive-end-expiratory pressure (PEEP) delivered by the ERS.

The results shown in Table 4 suggest that the systems and methods described herein are safe for use in patients requiring mechanical ventilation and may promote mobilization and removal of fluid from the respiratory tract. The mucus plug mobilization in this case is attributed to the increased diaphragmatic strength and forceful contractions with pacing therapy allowing the break up and clearance of distal mucus plugs in atelectatic lower lobes. This is demonstrated by the modest improvement in MIP and the reduction in pressure support. Specifically, use of respiratory muscle stimulation therapy may assist patients with achieving respiratory clearance by mobilizing lower airway secretions. Large mucus plug clearance may be facilitated by the systems and methods described herein, at least partially due to expansion of atelectatic lung bases. Close monitoring is obviously indicated in these patients as many will require assistance (e.g., suctioning, etc.) if secretion mobilization results in temporary airway obstruction.

Example 3

As described above, atelectasis is a significant cause of ventilator-induced lung injury in sedated, critically ill patients. Reducing atelectasis is a lung-protective strategy that can be difficult to achieve in a sedated, passively-breathing patient. Respiratory muscle stimulation therapy, in combination with mechanical ventilation, may offer a solution to this problem by preserving end-expiratory lung volume (EELV).

The progression of atelectasis can be measured in real time by observing the change in EELV using electrical impedance tomography (EIT), a non-invasive technique. Changes in regional air content modify electrical impedance of lung tissue, which can be reconstructed and displayed in a series of images.

A study was conducted using a 50 kilogram pig model in a mock-ICU environment. An MV-only control group (n=8) was subjected to usual standard of care, positive-pressure ventilation with volume control at 6-8 mL/kg. A MV+stimulation group (n=8) underwent respiratory muscle stimulation, resulting in a diaphragm contraction, on every second breath, during the inspiratory phase of ventilator-triggered breaths. For each subject, the change in EELV was recorded using EIT, and initial and final images of un-paced breaths were compared to calculate the change in EELV.

Figure 21A:
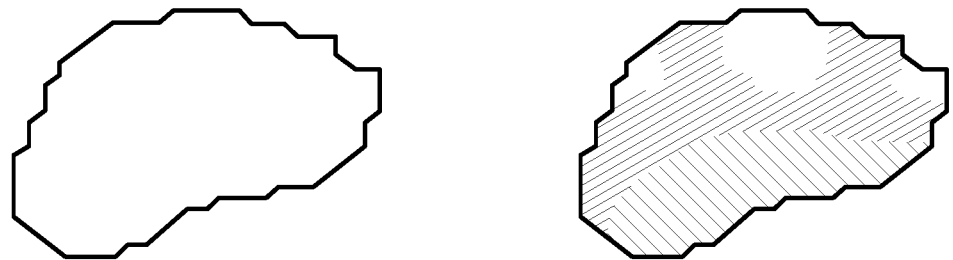
FIGS. 21A and 21B include EIT images taken of lungs undergoing mechanical ventilation and mechanical ventilation in combination with respiratory muscle stimulation, according to one or more embodiments.

Exemplary EIT images from the MV-only group are shown in FIG. 21A. The first image is before MV is applied, and the second image is after 50 hours of MV. These EIT images show a 1841 mL loss in EELV.

Figure 21B:
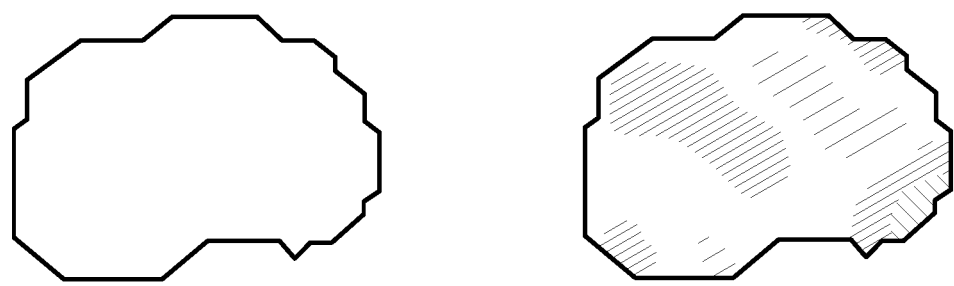

Comparatively, EIT images from the MV+stimulation group are shown in FIG. 21B. The first image is before MV and stimulation is applied, and the second image is after 50 hours of MV and stimulation. These EIT images show a 271 mL loss in EELV.

Figure 22:
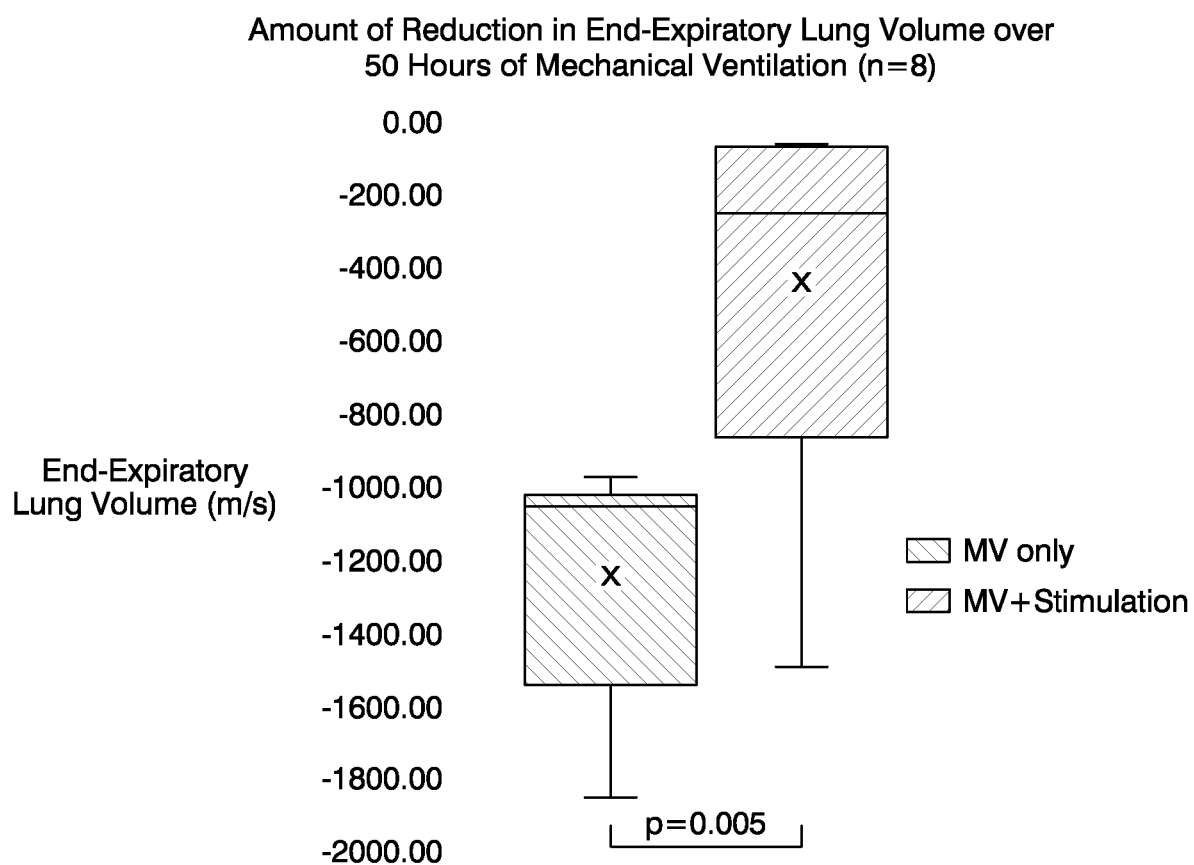
FIG. 22 illustrates a box plot of measured end expiratory lung volume losses, according to one or more embodiments.

Un-paced breaths from the experimental group were compared to control group breaths to ensure identical passive ventilation in both groups and to remove the effect of pacing. Means were compared by a two-tailed t-test with a significance level of alpha of 0.5 and beta of 0.80. Comparison of initial and final un-paced breaths in the MV+stimulation group showed a mean reduction in EELV of 430 ml compared to 1230 ml in the MV-only group over 50 hours of ventilation (p=0.005). This EIT analysis shows 286% more atelectasis is present in the MV-only group. A box plot summarizing these results is shown in FIG. 22.

Respiratory muscle stimulation therapy used in combination with MV significantly decreased loss of EELV over 50 hours. EELV is an accepted measure of atelectasis, and the smaller amount in the MV+stimulation group reflects more alveoli available to participate in ventilation. Reducing atelectasis encourages the preservation of a more homogenous distribution of ventilation, as there is a larger and more uniformly shaped area for tidal volume to be distributed. This is significant, as a reduction in atelectasis has many benefits, such as a reduction in atelectrauma, lower required ventilator driving pressures and, potentially, earlier weaning from mechanical ventilation.

Example 4

As described above, increased stress and strain due to atelectasis formation and barotrauma activate the inflammatory pathways and increase the levels of inflammatory cytokines, augmenting and perpetuating the lung injury process. Referring to the 50-kilogram pig study described in Example 3, a brocheoalveolar lavage (BAL) was performed in the right upper lobe of each subject both before and after the 50-hour treatment time. The samples from the BAL were analyzed for levels of IL-1β, IL-6 and IL-8. IL-1β is a biologically active cytokine and elevated serum levels are often an indication of early acute lung injury, as well as a predictor of poor clinical outcomes and a potent inducer of lung fibrosis. IL-10 causes the release of pro-inflammatory cytokines IL-6 and IL-8. IL-6 and IL-8 levels are often higher in serum of acute lung injury patients. Further, elevated levels of these cytokines are often associated with poor clinical outcomes. Means were compared by a two-tailed t-test with a significance level of alpha of 0.5 and beta of 0.80. The results from the IL-6 and IL-8 assays are summarized in box plots shown in FIGS. 23A, 23B, and 23C.

Figure 23A:
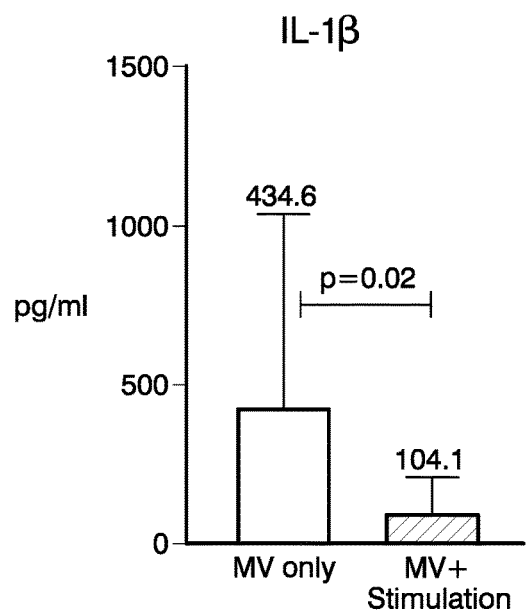
FIGS. 23A-23C illustrate box plots of measured blood concentrations of inflammatory markers, according to one or more embodiments.
Figure 23B:
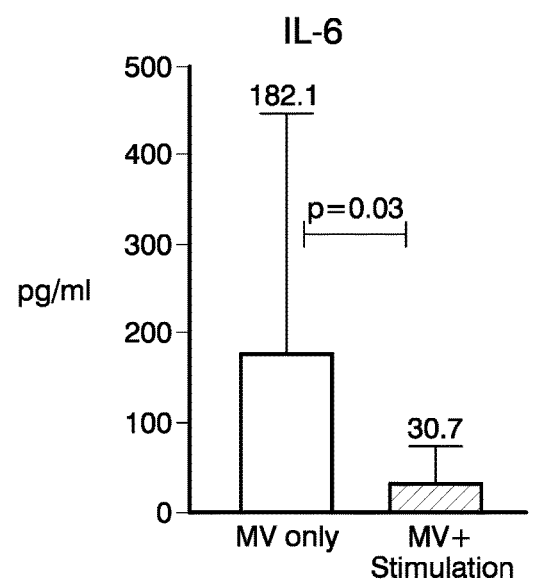
Figure 23C:
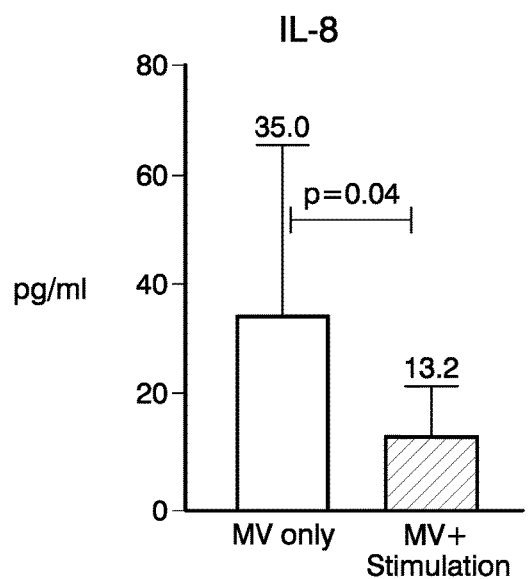

As seen in FIGS. 23A-23C, respiratory muscle stimulation therapy reduces the increase of inflammatory cytokines in broncheoalveolar lavage fluid in the right upper lobe over the course of 50 hours, compared to mechanical ventilation only. Overall IL-1β, IL-6 and IL-8 serum levels were significantly lower in the MV+stimulation group (n=8) than MV-Only group (n=8), indicating less systemic inflammation and less potential for secondary organ injury due to ventilator-induced lung injury. Lower systemic levels of inflammatory cytokines in the MV+stimulation group indicate that the pulmonary compartment was preserved in this group, thus the level of injury was lower. Without being limited by theory, the reduction of atelectasis and barotrauma may result in a more homogenous distribution of ventilation and less ventilator-induced lung injury. The significant difference in inflammatory markers between treatment and controlled groups indicates that synchronous diaphragm contractions during controlled ventilation helps to reduce lung inflammation in normal, healthy subjects.

In addition to the measured cytokine levels described herein, the peak inspiratory pressure, plateau pressure, and dynamic compliance were measured for subjects during breaths assisted by ERS (MV-only) and breaths assisted by ERS and stimulation (MV+stimulation). In other words, pressures and compliances were measured for each subject, both during stimulation assisted breaths and during breaths without stimulation assistance.

Figure 24A:
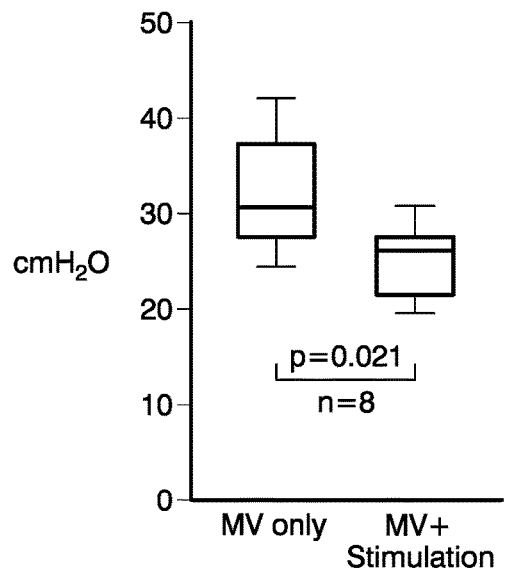
FIGS. 24A-24C illustrate a box plot and bar graphs of measured peak inspiratory pressures and plateau pressures, according to one or more embodiments.
Figure 24B:
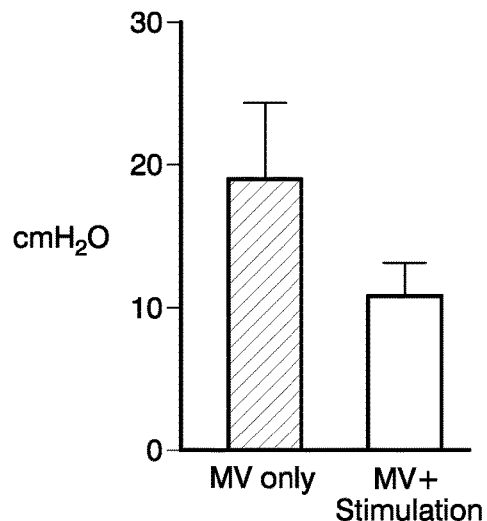
Figure 24C:
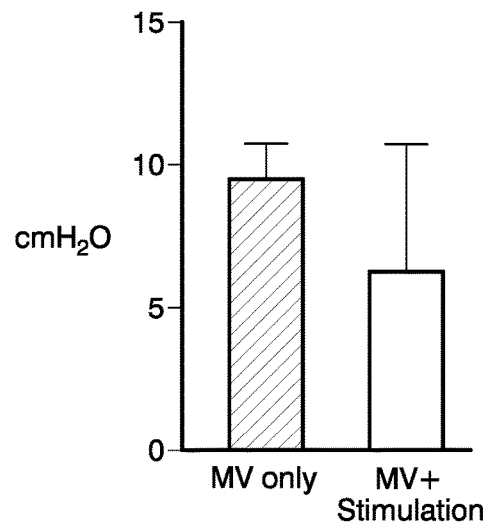
Figure 25A:
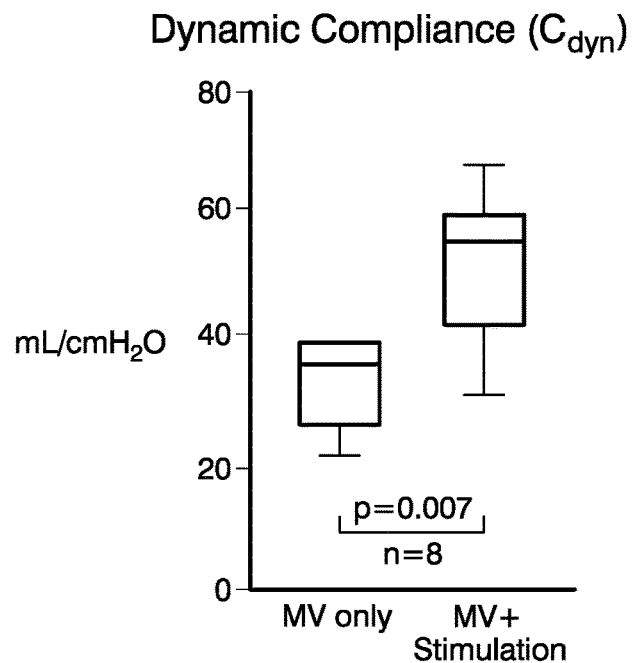
FIGS. 25A and 25B illustrate a box plot and a bar graph of measured dynamic compliances, according to one or more embodiments.
Figure 25B:
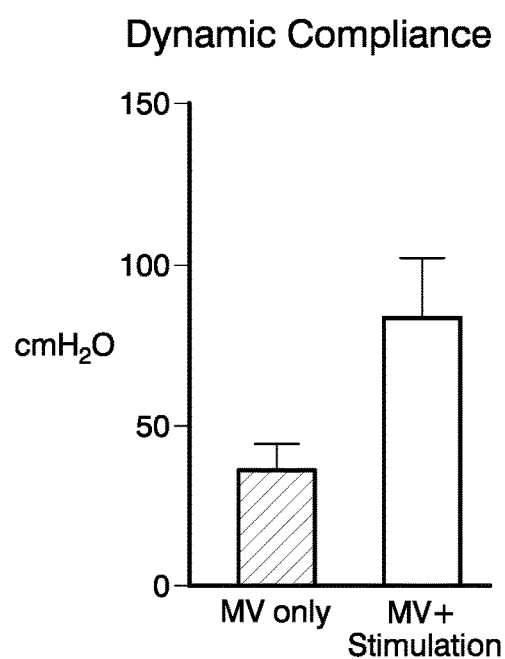

The peak inspiratory pressure and plateau pressure data shown in FIGS. 24A-24C show that stimulation assisted breaths included a lower average peak inspiratory pressure and a lower average plateau pressure, compared to breaths without stimulation assistance. Dynamic compliance is a measure of the ability of a respiratory system (e.g., lungs and associated airways) to stretch, expand, or receive volume. Dynamic compliance may be measured as the change in pressure of a respiratory system during air movement, divided by the change in volume over that timeframe. The compliance data shown in FIGS. 25A and 25B demonstrate that breaths assisted by stimulation resulted in greater dynamic compliance than breaths assisted by ERS only.

Example 5

A study was conducted using a 50-kilogram pig model to investigate how different types of diaphragm muscle fibers adapt to increased work demand caused by respiratory muscle stimulation. An MV-only control group (n=4) was subjected to positive-pressure ventilation. Ventilation parameters were set to achieve lung-protective volumes, with tidal volume at 8 mL/kg, positive end-expiratory pressure at 5 cm $H_2O$, and $FiO_2$ set at the minimum necessary to achieve adequate oxygenation. The pigs were deeply sedated with infusions of propofol, fentanyl, and midazolam, and were given boluses of ketamine to achieve an adequate sedation level guided by bi-spectral analysis (BIS). A MV+stimulation group (n=4) underwent respiratory muscle stimulation, resulting in a diaphragm contraction, on every second breath, during the inspiratory phase of ventilator-triggered breaths. The cross-sectional area of various types of muscle fibers between the two groups were compared. Specifically, samples were excised from the left costal diaphragm of each subject, posteuthanasia, clamped at its resting state prior to excision, and immediately preserved for analysis.

The relative abundances of each myofiber type, by cross-sectional area, for each treatment group, are shown below in Table 5.

TABLE 5

Relative Abundance of Myofiber Types by Cross-Sectional Area

| Treatment Group | Myofiber Type | | |
|---|---|---|---|
| | Type I | Type IIA | Type IIX |
| MV-Only | 39.39% | 32.66% | 33.26% |
| MV + Stimulation | 42.87% | 32.15% | 28.35% |

Type I myofibers are slow-twitch fibers, and may be referred to as slow-oxidative fibers. They have a slow contraction time following electrical stimulation, and generate less force than type 2 myofibers. Slow myofibers may be recruited at lower stimulation thresholds than other myofiber types. Type I myofibers are used for sustained, low-level activity, and are equipped with numerous large mitochondria and relatively abundant intracellular lipid for oxidative metabolism.

Type II myofibers are fast-twitch fibers, and may be referred to as fast-glycolytic fibers. They have a rapid contraction time following stimulation. Type II myofibers are recruited at higher threshold stimulation than type I myofibers and are used for brief-duration intense activity and for carrying heavy loads. Some type II myofibers are specialized for anaerobic metabolism and may contain smaller and fewer mitochondria, store less lipids, and have larger glycogen stores than type I fibers.

Type II fibers are divided into type IIA and type IIX fibers. Both of these fibers have high contraction speed, thus generating greater force compared to type I fibers. Type IIA fibers have moderately high contraction speed and are anaerobic in nature. Type IIA fibers also have high density of mitochondria with increased oxidative potential, and type IIb fibers have very high contraction speed and are anaerobic in nature. Type IIA fibers predominantly contain myosin isoform Myh2 in mammals, while type IIb fibers have low mitochondrial density and predominantly contain myosin isoform Myh4.

A gain in type I myofibers at the expense of type IIX myofibers, for example, during respiratory muscle stimulation may contribute to increased endurance of the respiratory muscle.

Figure 26A:
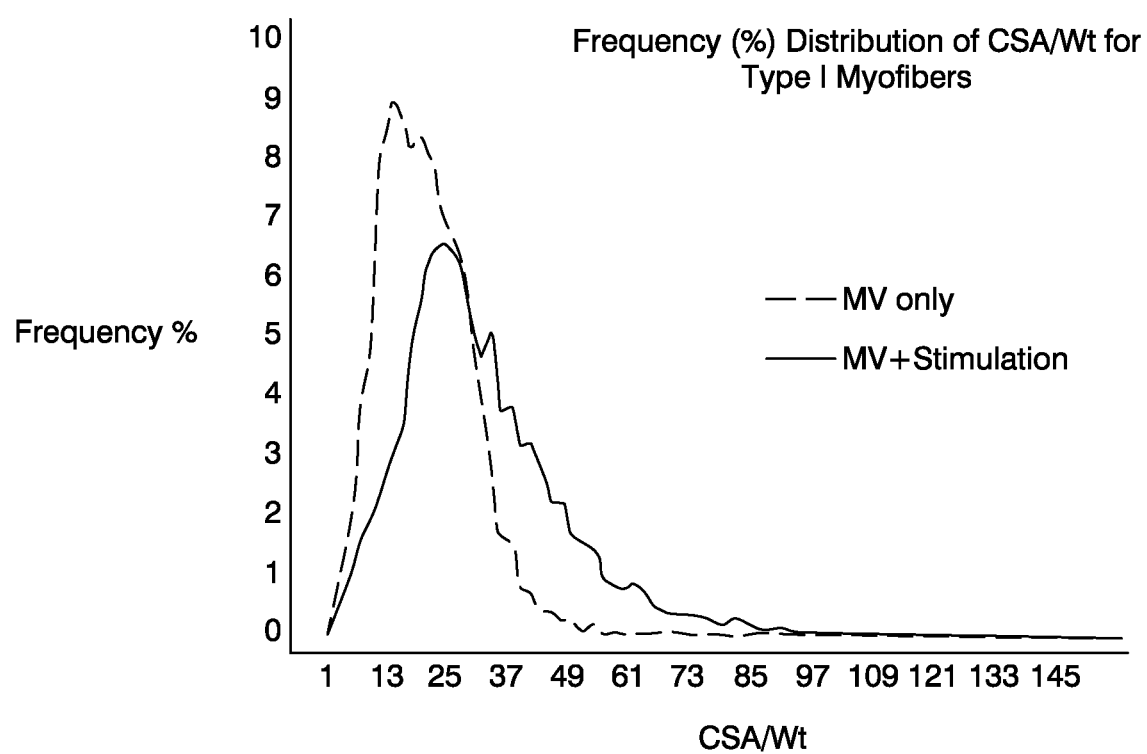
FIGS. 26A-26C illustrate frequency distributions of cross-sectional areas of different myofibers types, normalized by sample weight, according to one or more embodiments.
Figure 26B:
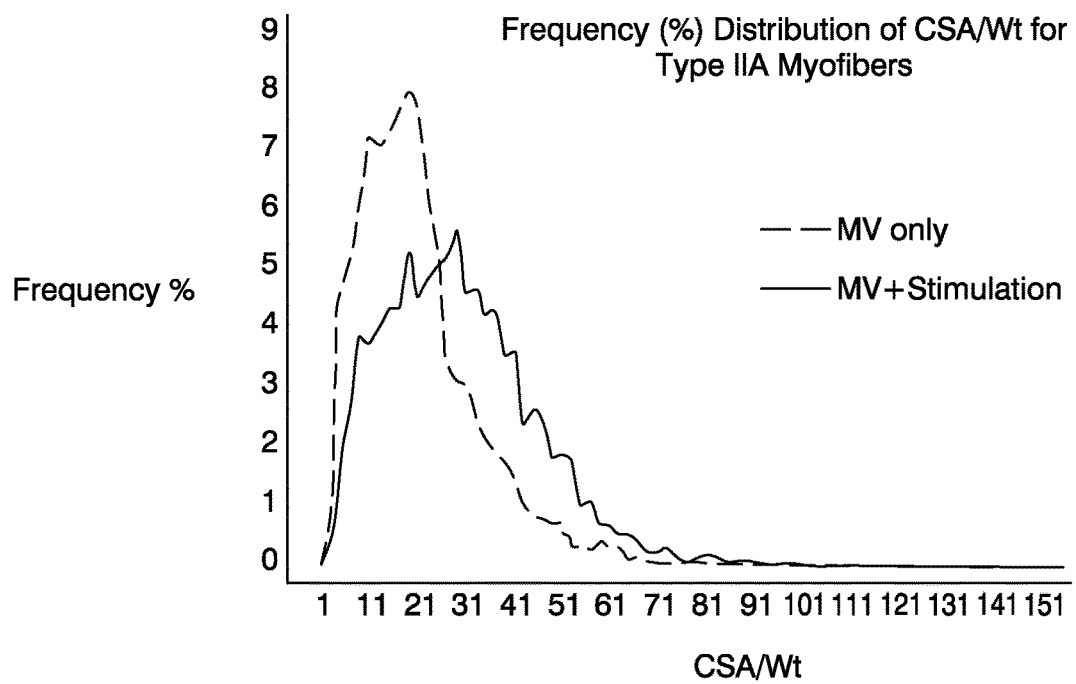
Figure 26C:
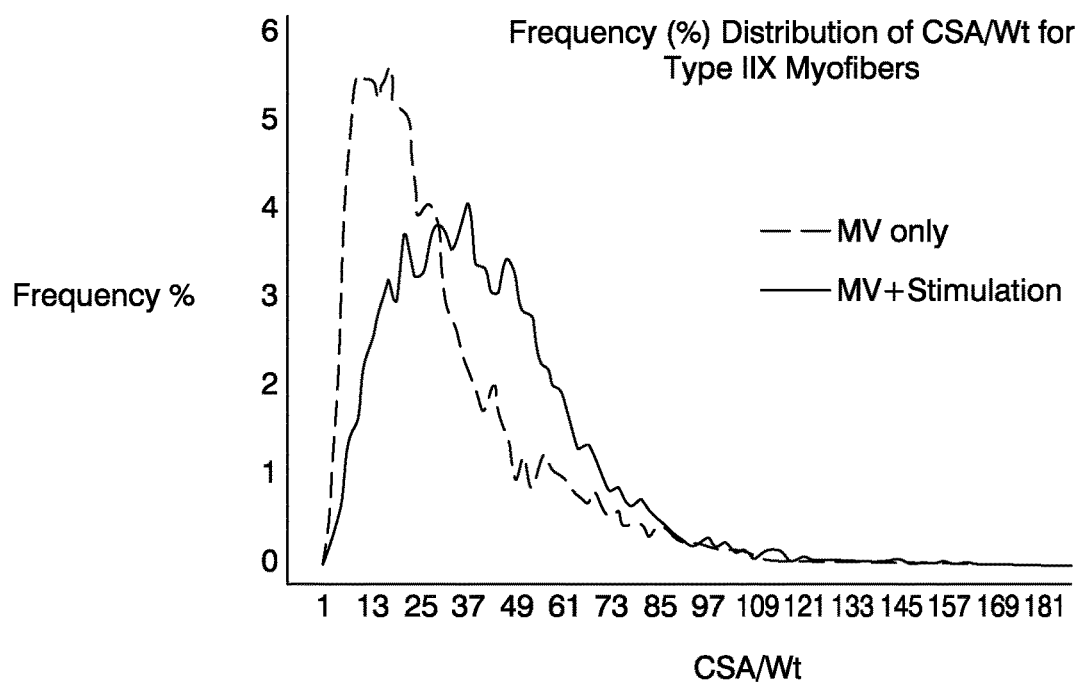

The cross-sectional areas for the identified myofibers were measured for each left costal diaphragm sample. The areas were normalized to the weight of the sample, and plotted in FIGS. 26A-26C. A Mann-Whitney U test statistic was used to determine levels of significance in the differences between both groups. The normalized pooled mean cross-sectional areas are summarized below in Table 6, along with the p-value from the Mann-Whitney U test.

TABLE 6

Pooled Mean Cross-Sectional Areas

| Treatment Group | Myofiber Type | | |
|---|---|---|---|
| | Type I | Type IIA | Type IIX |
| MV-Only | 19.35 ± 9.71 m$^2$/kg | 20.12 ± 12.47 m$^2$/kg | 29.26 ± 22.82 m$^2$/kg |
| MV + Stimulation | 30.84 ± 17.42 m$^2$/kg | 28.91 ± 16.28 m$^2$/kg | 40.33 ± 23.39 m$^2$/kg |
| p-value | <0.001 | | |

Therefore, growth of at least type I myofibers is promoted during respiratory muscle stimulation. Further, respirator muscle stimulation in synchrony with mechanical ventilation protects all diaphragm myofiber types from atrophy due to VIDD.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

What is claimed is:

1. A method of stimulating tissue comprising:
   delivering a first stimulation to tissue via a stimulation device, wherein the first stimulation comprises a first value of a stimulation parameter;
   measuring an impedance of lung tissue;
   calculating a lung gas parameter based on the impedance, wherein the lung gas parameter corresponds to an air distribution between the posterior and anterior regions of the lungs, an air distribution between the superior and inferior regions of the lungs, an air distribution between the right and left lungs, and/or one or more lung volumes;
   based on the lung gas parameter, determining a second value of the stimulation parameter of a second stimulation, wherein the second value is different than the first value; and
   delivering the second stimulation to tissue via the stimulation device.

2. The method of claim 1, further comprising comparing the lung gas parameter to a pre-determined lung gas parameter.

3. The method of claim 2, wherein the second value of the stimulation parameter of the second stimulation is determined based on the comparison of the lung gas parameter to the pre-determined lung gas parameter.

4. The method of claim 1, wherein delivering the first stimulation, delivering the second stimulation, or both, includes delivering electrical stimulation.

5. The method of claim 1, wherein delivering the second stimulation includes delivering stimulation to a phrenic nerve, and/or wherein delivering the second stimulation includes delivering stimulation that causes contraction of a respiratory muscle.

6. The method of claim 1, wherein the stimulation device includes at least one electrode, and the method further comprises positioning the stimulation device within a patient such that the at least one electrode is proximate a phrenic nerve.

7. The method of claim 6, wherein the impedance is measured via one or more sensors placed on or in the patient.

8. The method of claim 1, wherein the impedance of lung tissue is measured by an array of impedance sensors.

9. The method of claim 1, wherein the lung gas parameter corresponds to one or more lung volumes, and the one or more lung volumes include a volume of an inferior region or an anterior region of a lung.

10. A method of stimulating tissue comprising:
measuring a first bioelectrical impedance;
determining a first value of a lung gas parameter based on the first bioelectrical impedance, the lung gas parameter corresponding to a distribution of air between portions of lungs;
comparing the first value to a pre-determined value of the lung gas parameter;
determining one or more first stimulation parameters based on the comparison of the first value to the pre-determined value;
delivering a first stimulation signal, including the one or more stimulation parameters, to tissue;
measuring a second bioelectrical impedance;
determining a second value of the lung gas parameter based on the second bioelectrical impedance;
comparing the second value to the first value or the pre-determined value;
based on the comparison of the second value to the first value or the pre-determined value, determining one or more second stimulation parameters; and
delivering a second stimulation including the one or more second stimulation parameters.

11. The method of claim 10, wherein the one or more first stimulation parameters or the one or more second stimulation parameters includes a duration, a pulse width, a frequency, an amplitude, or a combination thereof.

12. The method of claim 10, wherein the first stimulation signal is delivered via at least one electrode, and the first bioelectrical impedance is measured via the at least one electrode.

13. The method of claim 10, wherein comparing the first value to the pre-determined value of the lung gas parameter includes comparing the first value to a pre-determined range of values.

14. The method of claim 10, wherein delivering the first or second stimulation signal causes a contraction of a respiratory muscle.

15. The method of claim 10, further comprising:
determining a first lung volume, prior to delivering the first stimulation signal; and
determining a second lung volume, after delivering the first stimulation signal.

16. The method of claim 15, wherein each of the first lung volume and the second lung volume is a volume of an inferior region or an anterior region of a lung.

17. A system for stimulating tissue comprising:
a stimulation device;
an impedance sensor; and
a control unit configured to:
receive an impedance signal from the impedance sensor;
determine a first value of a lung gas parameter based on the impedance signal, the lung gas parameter corresponding to a distribution of air between portions of lungs;
compare the first value to a pre-determined value of the lung gas parameter;
determine one or more stimulation parameters based on the comparison of the first value to the pre-determined value; and
deliver a stimulation signal, including the one or more stimulation parameters, to tissue, via the stimulation device.

18. The system of claim 17, further comprising an external respiratory support device.

19. The system of claim 17, wherein the impedance sensor is part of an array of impedance sensors, and the array is configured to be affixed to an exterior of the patient.

20. The system of claim 17, wherein the control unit is further configured to generate an image corresponding to the distribution of air between portions of lungs.

* * * * *